(12) United States Patent
Maisano et al.

(10) Patent No.: US 12,402,885 B2
(45) Date of Patent: Sep. 2, 2025

(54) MEDICAL OCCLUSION DEVICE

(71) Applicant: UNIVERSITÄT ZÜRICH, Zürich (CH)

(72) Inventors: Francesco Maisano, Küsnacht (CH); Andrea Guidotti, Zollikon (CH); Idan Tobis, Beth Hashmonai (IL); David Zarbatany, Laguna Niguel, CA (US)

(73) Assignee: UNIVERSITÄT ZÜRICH, Zurich (CH)

( * ) Notice: Subject to any disclaimer, the term of this patent is extended or adjusted under 35 U.S.C. 154(b) by 648 days.

(21) Appl. No.: 17/207,074

(22) Filed: Mar. 19, 2021

(65) Prior Publication Data
US 2021/0204961 A1 Jul. 8, 2021

Related U.S. Application Data

(63) Continuation of application No. PCT/US2019/024065, filed on Mar. 26, 2019, which
(Continued)

(30) Foreign Application Priority Data

Sep. 23, 2017 (EP) .................................. 17192792

(51) Int. Cl.
*A61B 17/12* (2006.01)
*A61B 17/00* (2006.01)
*A61M 25/10* (2013.01)

(52) U.S. Cl.
CPC .. *A61B 17/12122* (2013.01); *A61B 17/12136* (2013.01); *A61B 2017/00632* (2013.01);
(Continued)

(58) Field of Classification Search
CPC .......... A61B 17/0057; A61B 17/12109; A61B 17/12122; A61B 17/12136;
(Continued)

(56) References Cited

U.S. PATENT DOCUMENTS 3,834,394 A 9/1974 Hunter et al.
4,686,962 A 8/1987 Haber
(Continued)

FOREIGN PATENT DOCUMENTS

CN 104905890 A 9/2015
CN 204971415 U 1/2016
(Continued)

OTHER PUBLICATIONS

An International Search Report and a Written Opinion both dated Dec. 4, 2018, which issued during the prosecution of Applicant's PCT/EP2018/075716.
(Continued)

*Primary Examiner* — Mohamed G Gabr
(74) *Attorney, Agent, or Firm* — Sughrue Mion, PLLC

(57) ABSTRACT

An occlusion device (20) includes a compliant balloon (5) including an inflation port (3) for filling and unfilling a fluid into and from a balloon chamber (26). A distal tip element (10) and a proximal base element (4) are disposed at distal and proximal sides (28B, 28A) of the balloon (5), respectively. An elongate actuating element (9) is disposed longitudinally slidable in a balloon lumen (6) forming a longitudinal passage (27) from the proximal side (28A) to the distal side (28B) of the balloon (5), connected to the distal tip element (10), and longitudinally moveable with respect to the proximal base element (4) so as to set a distance between the distal tip element (100 and the proximal base element (4). A locking mechanism (2) is configured to maintain, between the distal tip element (10) and the proximal base element (4), the distance set using the elongate actuating element (9).

35 Claims, 24 Drawing Sheets

Related U.S. Application Data is a continuation-in-part of application No. PCT/EP2018/075716, filed on Sep. 23, 2018, application No. 17/207,074 is a continuation-in-part of application No. 16/649,777, filed as application No. PCT/EP2018/075716 on Sep. 23, 2018, now Pat. No. 11,517,319.

(52) U.S. Cl.
CPC ............... *A61B 2017/00862* (2013.01); *A61B 2017/12095* (2013.01); *A61M 25/1002* (2013.01); *A61M 2025/1079* (2013.01); *A61M 2025/1084* (2013.01)

(58) Field of Classification Search
CPC ........ A61B 17/12172; A61B 17/12177; A61B 2017/00243; A61B 2017/00557; A61B 2017/00575; A61B 2017/00592; A61B 2017/00597; A61B 2017/00606; A61B 2017/00619; A61B 2017/00623; A61B 2017/00632; A61B 2017/00783; A61B 2017/00862; A61B 2017/1205; A61B 2017/12054; A61B 2017/12095; A61F 2/2412; A61M 2025/1079; A61M 2025/1084; A61M 25/1002
See application file for complete search history.

(56) References Cited

U.S. PATENT DOCUMENTS

| | | | |
|---|---|---|---|
| 4,802,479 | A | 2/1989 | Haber et al. |
| 5,181,921 | A * | 1/1993 | Makita ............. A61B 17/12109 604/247 |
| 5,411,475 | A | 5/1995 | Atala et al. |
| 5,499,995 | A | 3/1996 | Teirstein |
| 5,795,325 | A | 8/1998 | Valley et al. |
| 5,830,228 | A | 11/1998 | Knapp et al. |
| 5,853,422 | A | 12/1998 | Huebsch et al. |
| 6,117,159 | A | 9/2000 | Huebsch et al. |
| 6,174,322 | B1 | 1/2001 | Schneidt |
| 6,231,561 | B1 | 5/2001 | Frazier et al. |
| 6,267,747 | B1 | 7/2001 | Samson et al. |
| 6,273,907 | B1 | 8/2001 | Laufer |
| 6,290,674 | B1 | 9/2001 | Roue et al. |
| 6,328,727 | B1 | 12/2001 | Frazier et al. |
| 6,334,864 | B1 | 1/2002 | Amplatz et al. |
| 6,419,669 | B1 | 7/2002 | Frazier et al. |
| 6,440,097 | B1 | 8/2002 | Kupiecki |
| 6,468,301 | B1 | 10/2002 | Amplatz et al. |
| 6,468,303 | B1 | 10/2002 | Amplatz et al. |
| 6,488,689 | B1 | 12/2002 | Kaplan et al. |
| 6,537,300 | B2 | 3/2003 | Girton |
| 6,544,268 | B1 | 4/2003 | Lazarus |
| 6,551,303 | B1 | 4/2003 | Van Tassel et al. |
| 6,638,257 | B2 | 10/2003 | Amplatz |
| 6,652,555 | B1 | 11/2003 | VanTassel et al. |
| 6,652,556 | B1 | 11/2003 | VanTassel et al. |
| 6,656,488 | B2 | 12/2003 | Yi et al. |
| 6,692,491 | B1 | 2/2004 | Phan |
| 6,926,712 | B2 | 8/2005 | Phan |
| 6,932,816 | B2 | 8/2005 | Phan |
| 6,941,169 | B2 | 9/2005 | Pappu |
| 6,942,661 | B2 | 9/2005 | Swanson |
| 6,942,681 | B2 | 9/2005 | Johnson |
| 6,964,669 | B1 | 11/2005 | Knapp et al. |
| 6,970,742 | B2 | 11/2005 | Mann et al. |
| 6,994,092 | B2 | 2/2006 | Van Der et al. |
| 7,011,671 | B2 | 3/2006 | Welch |
| 7,044,134 | B2 | 5/2006 | Khairkhahan et al. |
| 7,056,294 | B2 | 6/2006 | Khairkhahan et al. |
| 7,169,164 | B2 | 1/2007 | Borillo et al. |
| 7,211,048 | B1 | 5/2007 | Najafi et al. |
| 7,293,562 | B2 | 11/2007 | Malecki et al. |
| 7,338,514 | B2 | 3/2008 | Wahr et al. |
| 7,374,560 | B2 | 5/2008 | Ressemann et al. |
| 7,470,282 | B2 | 12/2008 | Shelso |
| 7,473,271 | B2 | 1/2009 | Gunderson |
| 7,483,743 | B2 | 1/2009 | Mann et al. |
| 7,549,988 | B2 | 6/2009 | Eberl et al. |
| 7,597,704 | B2 | 10/2009 | Frazier et al. |
| 7,604,612 | B2 | 10/2009 | Ressemann et al. |
| 7,615,010 | B1 | 11/2009 | Najafi et al. |
| 7,654,978 | B2 | 2/2010 | Wahr et al. |
| 7,713,282 | B2 | 5/2010 | Frazier et al. |
| 7,722,641 | B2 | 5/2010 | Van Der Burg et al. |
| 7,735,493 | B2 | 6/2010 | Van Der Burg et al. |
| 7,740,627 | B2 | 6/2010 | Gammie et al. |
| 7,749,157 | B2 | 7/2010 | Bertolero |
| 7,824,341 | B2 | 11/2010 | Krishnan |
| 7,828,818 | B2 | 11/2010 | Zang et al. |
| 7,837,619 | B2 | 11/2010 | Sogard et al. |
| 7,846,168 | B2 | 12/2010 | Liddicoat et al. |
| 7,846,175 | B2 | 12/2010 | Bonnette et al. |
| 7,857,811 | B2 | 12/2010 | Vaska et al. |
| 7,892,228 | B2 | 2/2011 | Landis et al. |
| 7,918,865 | B2 | 4/2011 | Liddicoat et al. |
| 7,972,359 | B2 | 7/2011 | Kreidler |
| 7,976,564 | B2 | 7/2011 | Blaeser et al. |
| 7,998,095 | B2 | 8/2011 | McAuley |
| 7,998,138 | B2 | 8/2011 | McAuley |
| 8,002,771 | B2 | 8/2011 | Cox et al. |
| 8,034,061 | B2 | 10/2011 | Amplatz et al. |
| 8,043,258 | B2 | 10/2011 | Ostroot |
| 8,048,147 | B2 | 11/2011 | Adams |
| 8,052,715 | B2 | 11/2011 | Quinn et al. |
| 8,057,530 | B2 | 11/2011 | Kusleika et al. |
| 8,080,032 | B2 | 12/2011 | Van Der Burg et al. |
| 8,097,015 | B2 | 1/2012 | Devellian |
| 8,100,938 | B2 | 1/2012 | Figulla et al. |
| 8,108,069 | B2 | 1/2012 | Stahler et al. |
| 8,114,123 | B2 | 2/2012 | Brenzel et al. |
| 8,133,221 | B2 | 3/2012 | Malecki et al. |
| 8,142,470 | B2 | 3/2012 | Quinn et al. |
| 8,148,470 | B1 | 4/2012 | Holtcamp et al. |
| 8,162,974 | B2 | 4/2012 | Eskuri et al. |
| 8,163,004 | B2 | 4/2012 | Amplatz et al. |
| 8,167,894 | B2 | 5/2012 | Miles et al. |
| 8,167,905 | B2 | 5/2012 | Michler et al. |
| 8,197,527 | B2 | 6/2012 | Borillo et al. |
| 8,204,605 | B2 | 6/2012 | Hastings et al. |
| 8,211,096 | B2 | 7/2012 | Pless et al. |
| 8,221,348 | B2 | 7/2012 | Hackett et al. |
| 8,221,405 | B2 | 7/2012 | Whisenant et al. |
| 8,235,885 | B2 | 8/2012 | Whisenant et al. |
| 8,235,988 | B2 | 8/2012 | Davis et al. |
| 8,252,051 | B2 | 8/2012 | Chau et al. |
| 8,257,724 | B2 | 9/2012 | Cromack et al. |
| 8,257,725 | B2 | 9/2012 | Cromack et al. |
| 8,308,798 | B2 | 11/2012 | Pintor et al. |
| 8,313,505 | B2 | 11/2012 | Amplatz et al. |
| 8,361,138 | B2 | 1/2013 | Adams |
| 8,366,743 | B2 | 2/2013 | Zeng et al. |
| 8,372,112 | B2 | 2/2013 | Christianson et al. |
| 8,398,670 | B2 | 3/2013 | Amplatz et al. |
| 8,402,974 | B2 | 3/2013 | Davis et al. |
| 8,408,214 | B2 | 4/2013 | Spenser |
| 8,409,219 | B2 | 4/2013 | Kelley et al. |
| 8,463,359 | B2 | 6/2013 | Saadat et al. |
| 8,480,708 | B2 | 7/2013 | Kassab et al. |
| 8,491,649 | B2 | 7/2013 | Mach |
| 8,511,214 | B2 | 8/2013 | Gries |
| 8,523,897 | B2 | 9/2013 | Van Der Burg et al. |
| 8,523,940 | B2 | 9/2013 | Richardson et al. |
| 8,529,597 | B2 | 9/2013 | Linder et al. |
| 8,540,616 | B2 | 9/2013 | Whisenant et al. |
| 8,545,491 | B2 | 10/2013 | Abboud et al. |
| 8,550,982 | B2 | 10/2013 | Eby |
| 8,568,474 | B2 | 10/2013 | Yeung et al. |
| 8,574,264 | B2 | 11/2013 | Blaeser et al. |
| 8,613,765 | B2 | 12/2013 | Bonhoeffer et al. |
| 8,617,145 | B2 | 12/2013 | Longoria |
| 8,621,975 | B2 | 1/2014 | Russo et al. |

(56) References Cited

U.S. PATENT DOCUMENTS

| | | |
|---|---|---|
| 8,636,764 B2 | 1/2014 | Miles et al. |
| 8,647,361 B2 | 2/2014 | Borillo et al. |
| 8,647,367 B2 | 2/2014 | Kassab et al. |
| 8,652,201 B2 | 2/2014 | Oberti et al. |
| 8,663,245 B2 | 3/2014 | Francischelli et al. |
| 8,673,001 B2 | 3/2014 | Cartledge et al. |
| 8,690,911 B2 | 4/2014 | Miles et al. |
| 8,696,742 B2 | 4/2014 | Pintor et al. |
| 8,709,007 B2 | 4/2014 | Vaska |
| 8,715,270 B2 | 5/2014 | Weitzner et al. |
| 8,721,636 B2 | 5/2014 | Vaska et al. |
| 8,740,934 B2 | 6/2014 | McGuckin, Jr. |
| 8,747,297 B2 | 6/2014 | Miyoshi et al. |
| 8,747,453 B2 | 6/2014 | Amplatz et al. |
| 8,747,462 B2 | 6/2014 | Hill et al. |
| 8,758,294 B2 | 6/2014 | Kim et al. |
| 8,758,372 B2 | 6/2014 | Cartledge et al. |
| 8,758,389 B2 | 6/2014 | Glimsdale |
| 8,764,787 B2 | 7/2014 | Ren |
| 8,764,793 B2 | 7/2014 | Lee |
| 8,771,297 B2 | 7/2014 | Miller et al. |
| 8,777,974 B2 | 7/2014 | Amplatz et al. |
| 8,778,008 B2 | 7/2014 | Amplatz et al. |
| 8,784,469 B2 | 7/2014 | Kassab |
| 8,795,310 B2 | 8/2014 | Fung et al. |
| 8,795,328 B2 | 8/2014 | Miles et al. |
| 8,801,706 B2 | 8/2014 | Rothstein et al. |
| 8,801,746 B1 | 8/2014 | Kreidler et al. |
| 8,808,371 B2 | 8/2014 | Cartledge |
| 8,814,778 B2 | 8/2014 | Kiser et al. |
| D713,527 S | 9/2014 | Heipl |
| 8,821,529 B2 | 9/2014 | Kariniemi et al. |
| 8,834,519 B2 | 9/2014 | Van Der Burg et al. |
| 8,840,641 B2 | 9/2014 | Miles et al. |
| 8,840,655 B2 | 9/2014 | Edmiston et al. |
| 8,845,711 B2 | 9/2014 | Miles et al. |
| 8,864,809 B2 | 10/2014 | Miles et al. |
| 8,864,823 B2 | 10/2014 | Cartledge et al. |
| 8,876,776 B2 | 11/2014 | Kassab et al. |
| 8,880,185 B2 | 11/2014 | Hastings et al. |
| 8,882,830 B2 | 11/2014 | Cartledge et al. |
| 8,900,287 B2 | 12/2014 | Amplatz et al. |
| 8,915,958 B2 | 12/2014 | Braido |
| 8,940,015 B2 | 1/2015 | Kariniemi |
| 8,951,251 B2 | 2/2015 | Willard |
| 8,956,304 B2 | 2/2015 | Schecter |
| 8,974,451 B2 | 3/2015 | Smith |
| 8,979,941 B2 | 3/2015 | Davis et al. |
| 8,986,375 B2 | 3/2015 | Garde et al. |
| D727,500 S | 4/2015 | Heipl |
| D727,501 S | 4/2015 | Heipl |
| D728,102 S | 4/2015 | Heipl |
| 9,011,551 B2 | 4/2015 | Oral et al. |
| 9,017,375 B2 | 4/2015 | Thommen |
| 9,023,034 B2 | 5/2015 | Jenson et al. |
| 9,028,485 B2 | 5/2015 | Edmunds et al. |
| 9,034,006 B2 | 5/2015 | Quinn et al. |
| 9,039,724 B2 | 5/2015 | Amplatz et al. |
| 9,039,752 B2 | 5/2015 | Russo et al. |
| 9,050,106 B2 | 6/2015 | Hill et al. |
| 9,055,933 B2 | 6/2015 | Escobar et al. |
| 9,055,959 B2 | 6/2015 | Vaska et al. |
| 9,060,761 B2 | 6/2015 | Hastings et al. |
| 9,066,710 B2 | 6/2015 | Dale et al. |
| 9,066,826 B2 | 6/2015 | Heidner et al. |
| 9,072,602 B2 | 7/2015 | Glozman et al. |
| 9,072,604 B1 | 7/2015 | Melnick et al. |
| 9,079,000 B2 | 7/2015 | Hanson et al. |
| 9,084,589 B2 | 7/2015 | Moszner |
| 9,084,609 B2 | 7/2015 | Smith |
| 9,084,621 B2 | 7/2015 | Weitzner et al. |
| 9,089,350 B2 | 7/2015 | Willard |
| 9,089,414 B2 | 7/2015 | Zimmerman et al. |
| 9,107,750 B2 | 8/2015 | Cartledge et al. |
| 9,113,890 B2 | 8/2015 | Dasnurkar et al. |
| 9,119,600 B2 | 9/2015 | Richardson et al. |
| 9,119,632 B2 | 9/2015 | Jenson et al. |
| 9,125,653 B2 | 9/2015 | Kovach |
| 9,131,932 B2 | 9/2015 | Tegels |
| 9,132,007 B2 | 9/2015 | Menk et al. |
| 9,138,208 B2 | 9/2015 | Linder et al. |
| 9,144,431 B2 | 9/2015 | Friedman et al. |
| 9,144,663 B2 | 9/2015 | Ahlberg et al. |
| 9,155,589 B2 | 10/2015 | Jenson |
| 9,161,758 B2 | 10/2015 | Figulla et al. |
| 9,162,046 B2 | 10/2015 | Hill et al. |
| 9,173,696 B2 | 11/2015 | Schauer et al. |
| 9,186,174 B2 | 11/2015 | Krishnan |
| 9,186,209 B2 | 11/2015 | Weber et al. |
| 9,186,210 B2 | 11/2015 | Jenson |
| 9,186,211 B2 | 11/2015 | Mathur |
| 9,192,435 B2 | 11/2015 | Jenson |
| 9,192,790 B2 | 11/2015 | Hastings et al. |
| 9,198,683 B2 | 12/2015 | Friedman et al. |
| 9,216,014 B2 | 12/2015 | Devellian et al. |
| 9,220,402 B2 | 12/2015 | Rothe et al. |
| 9,220,487 B2 | 12/2015 | Davis et al. |
| 9,220,558 B2 | 12/2015 | Willard |
| 9,220,561 B2 | 12/2015 | Crow et al. |
| 9,226,838 B2 | 1/2016 | Wang et al. |
| 9,232,992 B2 | 1/2016 | Heidner et al. |
| 9,241,792 B2 | 1/2016 | Benichou et al. |
| 9,254,141 B2 | 2/2016 | Morris et al. |
| 9,254,192 B2 | 2/2016 | Lutter et al. |
| 9,271,736 B2 | 3/2016 | Heipl |
| 9,277,905 B2 | 3/2016 | Cully et al. |
| 9,277,915 B2 | 3/2016 | Belson et al. |
| 9,289,266 B2 | 3/2016 | Weitzner et al. |
| 9,290,612 B2 | 3/2016 | Martin et al. |
| 9,295,472 B2 | 3/2016 | Ottma |
| 9,295,484 B2 | 3/2016 | Solem |
| 9,297,845 B2 | 3/2016 | Mathur |
| 9,301,838 B2 | 4/2016 | Kapadia |
| 9,307,999 B2 | 4/2016 | Li et al. |
| 9,320,525 B2 | 4/2016 | Khieu et al. |
| 9,326,751 B2 | 5/2016 | Hastings |
| 9,326,852 B2 | 5/2016 | Spenser |
| 9,333,073 B2 | 5/2016 | Quadri et al. |
| 9,339,274 B2 | 5/2016 | Dakin |
| 9,345,462 B2 | 5/2016 | Weitzner et al. |
| 9,351,716 B2 | 5/2016 | Miles et al. |
| 9,358,365 B2 | 6/2016 | Smith et al. |
| 9,364,284 B2 | 6/2016 | Groff et al. |
| 9,370,418 B2 | 6/2016 | Pintor et al. |
| 9,375,209 B2 | 6/2016 | Akpinar |
| 9,375,218 B2 | 6/2016 | Wheeler et al. |
| 9,398,951 B2 | 7/2016 | Alkhatib et al. |
| 9,408,608 B2 | 8/2016 | Clark, III et al. |
| 9,408,661 B2 | 8/2016 | Haverkost |
| 9,408,951 B2 | 8/2016 | Larsen et al. |
| 9,414,842 B2 | 8/2016 | Glimsdale et al. |
| 9,420,955 B2 | 8/2016 | Weber |
| 9,421,071 B2 | 8/2016 | Smith et al. |
| 9,427,215 B2 | 8/2016 | Cartledge et al. |
| 9,427,235 B2 | 8/2016 | Krishnan |
| 9,427,550 B2 | 8/2016 | Dakin et al. |
| 9,433,760 B2 | 9/2016 | Subramaniam et al. |
| 9,445,798 B2 | 9/2016 | Amplatz et al. |
| 9,445,799 B2 | 9/2016 | Amplatz et al. |
| 9,456,877 B2 | 10/2016 | Weitzner et al. |
| 9,456,897 B2 | 10/2016 | Krivoruchko et al. |
| 9,463,024 B2 | 10/2016 | Kiser et al. |
| 9,463,062 B2 | 10/2016 | Smith et al. |
| 9,468,437 B2 | 10/2016 | Michler et al. |
| 9,474,516 B2 | 10/2016 | Clark et al. |
| 9,474,598 B2 | 10/2016 | Gregg et al. |
| 9,474,599 B2 | 10/2016 | Keränen |
| 9,492,156 B2 | 11/2016 | Tegels |
| 9,492,276 B2 | 11/2016 | Lee et al. |
| 9,492,623 B2 | 11/2016 | Kapadia et al. |
| 9,498,206 B2 | 11/2016 | Fung et al. |
| 9,498,228 B2 | 11/2016 | Dale et al. |
| 9,510,811 B2 | 12/2016 | Akpinar |
| 9,532,772 B2 | 1/2017 | Moszner et al. |

(56) References Cited

U.S. PATENT DOCUMENTS

| | | | |
|---|---|---|---|
| 9,545,306 B2 | 1/2017 | Tabor |
| 9,572,583 B2 | 2/2017 | Kauphusman et al. |
| 9,579,030 B2 | 2/2017 | Scheuermann et al. |
| 9,579,194 B2 | 2/2017 | Elizondo et al. |
| 9,585,643 B2 | 3/2017 | Terwey |
| 9,585,644 B2 | 3/2017 | Linder et al. |
| 9,610,082 B2 | 4/2017 | Morris et al. |
| 9,622,133 B1 | 4/2017 | Guvenc |
| 9,636,222 B2 | 5/2017 | Oslund |
| 9,642,706 B2 | 5/2017 | Eidenschink |
| 9,649,115 B2 | 5/2017 | Edmiston et al. |
| 9,649,156 B2 | 5/2017 | Jenson et al. |
| 9,650,730 B2 | 5/2017 | Heipl et al. |
| 9,655,606 B2 | 5/2017 | Le |
| 9,662,205 B2 | 5/2017 | Eidenschink |
| 9,668,811 B2 | 6/2017 | Sogard et al. |
| 9,668,856 B2 | 6/2017 | Para |
| 9,668,857 B2 | 6/2017 | Braido et al. |
| 9,668,858 B2 | 6/2017 | Morin et al. |
| 9,675,451 B2 | 6/2017 | Garde et al. |
| 9,681,861 B2 | 6/2017 | Heisel et al. |
| 9,687,166 B2 | 6/2017 | Subramaniam et al. |
| 9,687,341 B2 | 6/2017 | Alkhatib et al. |
| 9,687,585 B2 | 6/2017 | Bernasconi et al. |
| 9,693,781 B2 | 7/2017 | Miles et al. |
| 9,693,821 B2 | 7/2017 | Hanson et al. |
| 9,694,115 B2 | 7/2017 | Zhang et al. |
| 9,700,323 B2 | 7/2017 | Clark |
| 9,707,036 B2 | 7/2017 | Anderson et al. |
| 9,713,730 B2 | 7/2017 | Mathur et al. |
| 9,717,501 B2 | 8/2017 | Kauphusman et al. |
| 9,730,701 B2 | 8/2017 | Tischler et al. |
| 9,737,309 B1 | 8/2017 | Ad |
| 9,750,605 B2 | 9/2017 | Ganesan et al. |
| 9,757,230 B2 | 9/2017 | Fahim et al. |
| 9,770,606 B2 | 9/2017 | Pikus et al. |
| 9,775,533 B2 | 10/2017 | Ong et al. |
| 9,789,232 B2 | 10/2017 | Liu et al. |
| 9,795,387 B2 | 10/2017 | Miles et al. |
| 9,795,481 B2 | 10/2017 | Callas et al. |
| 9,795,765 B2 | 10/2017 | Romoscanu |
| 9,808,253 B2 | 11/2017 | Li et al. |
| 9,808,300 B2 | 11/2017 | Hastings et al. |
| 9,808,311 B2 | 11/2017 | Wang et al. |
| 9,820,851 B2 | 11/2017 | Braido |
| 9,820,852 B2 | 11/2017 | Braido et al. |
| 9,827,039 B2 | 11/2017 | Dandler et al. |
| 9,833,283 B2 | 12/2017 | Hanson et al. |
| 9,839,430 B2 | 12/2017 | Willems et al. |
| 9,839,431 B2 | 12/2017 | Meyer et al. |
| 9,844,453 B2 | 12/2017 | Stack et al. |
| 9,848,898 B2 | 12/2017 | Friedman et al. |
| 9,848,976 B2 | 12/2017 | Angel et al. |
| 9,848,981 B2 | 12/2017 | Suri et al. |
| 9,863,031 B2 | 1/2018 | Zhang et al. |
| 9,867,697 B2 | 1/2018 | Alkhatib et al. |
| 9,877,710 B2 | 1/2018 | Amplatz et al. |
| 9,877,726 B2 | 1/2018 | Liu et al. |
| 9,878,072 B2 | 1/2018 | Zhang et al. |
| 9,883,855 B2 | 2/2018 | Tegels et al. |
| 9,883,936 B2 | 2/2018 | Sutton et al. |
| 9,888,926 B2 | 2/2018 | Phan et al. |
| 9,889,004 B2 | 2/2018 | Braido |
| 9,895,194 B2 | 2/2018 | Anderson et al. |
| 9,901,443 B2 | 2/2018 | Morriss et al. |
| 9,907,609 B2 | 3/2018 | Cao et al. |
| 9,913,652 B2 | 3/2018 | Bridgeman et al. |
| 9,913,715 B2 | 3/2018 | Braido et al. |
| 9,918,707 B2 | 3/2018 | Zhuang |
| 9,919,080 B1 | 3/2018 | Chen et al. |
| 9,925,001 B2 | 3/2018 | Willard et al. |
| 9,931,204 B2 | 4/2018 | Rothstein et al. |
| 9,936,956 B2 | 4/2018 | Fung et al. |
| 9,943,315 B2 | 4/2018 | Kaplan et al. |
| 9,943,365 B2 | 4/2018 | Haverkost et al. |
| 9,949,825 B2 | 4/2018 | Braido et al. |
| 9,955,971 B2 | 5/2018 | Xu et al. |
| 9,956,033 B2 | 5/2018 | Squire et al. |
| 9,962,223 B2 | 5/2018 | Lindquist et al. |
| 9,974,649 B2 | 5/2018 | Racchini et al. |
| 9,980,818 B2 | 5/2018 | Chau et al. |
| 9,993,234 B2 | 6/2018 | Maslanka et al. |
| 10,010,402 B2 | 7/2018 | Wang et al. |
| 10,013,082 B2 | 7/2018 | Schecter |
| 10,016,200 B2 | 7/2018 | Tegels |
| 10,022,182 B2 | 7/2018 | Willard et al. |
| 10,028,746 B2 | 7/2018 | Prom |
| 10,034,748 B2 | 7/2018 | Tseng et al. |
| 10,045,784 B2 | 8/2018 | Friedman et al. |
| 10,052,168 B2 | 8/2018 | Krishnan |
| 10,058,348 B2 | 8/2018 | Morris et al. |
| 10,058,636 B2 | 8/2018 | Xie et al. |
| 10,058,639 B2 | 8/2018 | Zhang et al. |
| 10,064,612 B2 | 9/2018 | Malakan Rad et al. |
| 10,064,628 B2 | 9/2018 | Edmiston et al. |
| 10,076,330 B2 | 9/2018 | Sander et al. |
| 10,076,335 B2 | 9/2018 | Zaver et al. |
| 10,085,799 B2 | 10/2018 | Smith |
| 10,098,640 B2 | 10/2018 | Bertolero et al. |
| 10,105,219 B2 | 10/2018 | Kovach |
| 10,117,743 B2 | 11/2018 | Kumar et al. |
| 10,130,369 B2 | 11/2018 | Fung et al. |
| 10,130,467 B2 | 11/2018 | Braido et al. |
| 10,143,478 B2 | 12/2018 | Forbes |
| 10,143,551 B2 | 12/2018 | Braido et al. |
| 10,271,949 B2 | 4/2019 | Dakin et al. |
| 2003/0139819 A1* | 7/2003 | Beer ............... A61B 17/0057 623/23.71 |
| 2003/0191516 A1 | 10/2003 | Weldon et al. |
| 2003/0220667 A1 | 11/2003 | Van Der Burg et al. |
| 2004/0044361 A1 | 3/2004 | Frazier et al. |
| 2004/0098017 A1 | 5/2004 | Saab et al. |
| 2004/0254594 A1 | 12/2004 | Alfaro |
| 2005/0043759 A1* | 2/2005 | Chanduszko ...... A61B 17/0057 606/213 |
| 2005/0288706 A1 | 12/2005 | Widomski et al. |
| 2006/0004442 A1 | 1/2006 | Spenser et al. |
| 2006/0200191 A1 | 9/2006 | Zadno-azizi et al. |
| 2007/0066993 A1* | 3/2007 | Kreidler ........... A61B 17/12122 606/213 |
| 2007/0135831 A1 | 6/2007 | Burnett |
| 2007/0225756 A1 | 9/2007 | Preinitz et al. |
| 2008/0071310 A1 | 3/2008 | Hoffman et al. |
| 2008/0103479 A1 | 5/2008 | Cheng et al. |
| 2010/0100107 A1 | 4/2010 | Duggal et al. |
| 2010/0125244 A1 | 5/2010 | Mcandrew |
| 2010/0185233 A1* | 7/2010 | Thommen ......... A61B 17/0057 606/213 |
| 2011/0172697 A1 | 7/2011 | Jönsson |
| 2012/0078295 A1* | 3/2012 | Steiner ............. A61B 17/0057 606/213 |
| 2012/0323270 A1 | 12/2012 | Lee |
| 2013/0030519 A1 | 1/2013 | Tran et al. |
| 2013/0211495 A1 | 8/2013 | Halden et al. |
| 2014/0100596 A1 | 4/2014 | Rudman et al. |
| 2014/0257457 A1 | 9/2014 | Glazier et al. |
| 2014/0277426 A1 | 9/2014 | Dakin et al. |
| 2016/0045165 A1 | 2/2016 | Braido et al. |
| 2018/0008248 A1 | 1/2018 | Rafiee et al. |
| 2018/0161039 A1 | 6/2018 | Harks |
| 2018/0193027 A1 | 7/2018 | Wang et al. |
| 2018/0206850 A1 | 7/2018 | Wang et al. |
| 2019/0223883 A1 | 7/2019 | Anderson et al. |
| 2020/0054343 A1 | 2/2020 | Min et al. |
| 2020/0085445 A1 | 3/2020 | Wang et al. |
| 2020/0100797 A1 | 4/2020 | Wang et al. |
| 2020/0107836 A1 | 4/2020 | O'halloran et al. |
| 2020/0121891 A1 | 4/2020 | Zhang et al. |
| 2020/0275935 A1 | 9/2020 | Maisano et al. |

(56) References Cited

U.S. PATENT DOCUMENTS

| | | | |
|---|---|---|---|
| 2020/0305887 A1 | 10/2020 | Lashinski et al. | |
| 2021/0386429 A1 | 12/2021 | Franano et al. | |

FOREIGN PATENT DOCUMENTS

| | | |
|---|---|---|
| CN | 106344082 A | 1/2017 |
| CN | 207928350 U | 10/2018 |
| CN | 207928351 U | 10/2018 |
| CN | 109199468 A | 1/2019 |
| CN | 208709959 U | 4/2019 |
| CN | 208958225 U | 6/2019 |
| CN | 209107426 U | 7/2019 |
| CN | 209107470 U | 7/2019 |
| CN | 209611296 U | 11/2019 |
| CN | 209611297 U | 11/2019 |
| CN | 110720958 A | 1/2020 |
| CN | 209884221 U | 1/2020 |
| CN | 210408510 U | 4/2020 |
| CN | 210408511 U | 4/2020 |
| CN | 111166461 A | 5/2020 |
| CN | 111166462 A | 5/2020 |
| CN | 111166463 A | 5/2020 |
| CN | 111803169 A | 10/2020 |
| CN | 212346702 U | 1/2021 |
| CN | 106473791 B | 10/2023 |
| CN | 106466196 B | 11/2023 |
| CN | 108926371 B | 4/2024 |
| EP | 1651117 | 1/2007 |
| EP | 1113751 | 3/2007 |
| EP | 1154723 | 12/2007 |
| EP | 1891902 | 2/2008 |
| EP | 1788957 | 3/2008 |
| EP | 1 974 685 A1 | 10/2008 |
| EP | 1881804 | 9/2009 |
| EP | 1313406 | 6/2010 |
| EP | 1123130 | 7/2010 |
| EP | 1948030 | 7/2010 |
| EP | 1441649 | 8/2011 |
| EP | 1993621 | 8/2011 |
| EP | 1842490 | 9/2011 |
| EP | 2074953 | 6/2012 |
| EP | 2019633 | 8/2012 |
| EP | 2248471 | 10/2012 |
| EP | 1575421 | 10/2013 |
| EP | 2327429 | 9/2014 |
| EP | 1761296 | 11/2014 |
| EP | 1765225 | 9/2015 |
| EP | 2630919 | 9/2015 |
| EP | 2822656 | 10/2016 |
| EP | 2872051 | 3/2017 |
| EP | 2970572 | 4/2017 |
| EP | 2779910 | 5/2017 |
| EP | 2967852 | 6/2017 |
| EP | 3037043 | 9/2017 |
| EP | 2617386 | 10/2017 |
| EP | 2819585 | 11/2017 |
| EP | 3043746 | 11/2017 |
| EP | 3183012 | 12/2017 |
| EP | 1768604 | 1/2018 |
| EP | 2967869 | 1/2018 |
| EP | 3125780 | 1/2018 |
| EP | 3044221 | 2/2018 |
| EP | 2575678 | 5/2018 |
| EP | 2833836 | 5/2018 |
| EP | 2908744 | 8/2018 |
| EP | 2918251 | 8/2018 |
| EP | 3193791 | 8/2018 |
| EP | 2753246 | 11/2018 |
| EP | 3010446 | 12/2018 |
| EP | 3459469 | 3/2019 |
| EP | 3 620 134 A1 | 3/2020 |
| WO | 95/032018 | 11/1995 |
| WO | 1999/018886 | 4/1999 |
| WO | 2000/012169 | 3/2000 |
| WO | 03/039624 A2 | 5/2003 |
| WO | 2005/092204 A2 | 10/2005 |
| WO | 2011/011765 A2 | 1/2011 |
| WO | 2013/068466 | 5/2013 |
| WO | 2014/085590 A1 | 6/2014 |
| WO | 2016/149653 A2 | 9/2016 |
| WO | 2017/079234 | 5/2017 |
| WO | 2017/161283 | 9/2017 |

OTHER PUBLICATIONS

An International Search Report and a Written Opinion both dated Jun. 18, 2019, which issued during the prosecution of Applicant's PCT/US2019/024065.

An International Search Report and a Written Opinion both dated Jul. 6, 2021, which issued during the prosecution of Applicant's PCT/IB2021/052474.

An International Search Report and a Written Opinion both dated Mar. 29, 2021, which issued during the prosecution of Applicant's PCT/IL2020/051041.

European Search Report dated Mar. 12, 2018 which issued during the prosecution of Applicant's European App No. 17192792.4.

An Office Action dated Mar. 7, 2022, which issued during the prosecution of Indian Patent Application No. 202017015683.

An Office Action dated Dec. 22, 2021, which issued during the prosecution of U.S. Appl. No. 16/649,777.

Notice of Allowance issued in U.S. Appl. No. 16/649,777, dated Jun. 24, 2022.

Office Action issued in Japanese Appl. No. 516870/2020, dated Sep. 27, 2022.

Extended European search report in counterpart European Appl. No. 19862977.6, dated Dec. 15, 2022.

First Examination Report in counterpart Indian Appl. No. 202117016867, dated Feb. 3, 2023.

Office Action in counterpart Japanese Appl. No. 516654/2021, dated Feb. 14, 2023.

Office Action in Chinese Appl. No. 201880061656.0, dated Feb. 23, 2023.

Non-Final Office Action in U.S. Appl. No. 17/763,485, dated May 22, 2023.

Decision of Refusal in Japanese Appl. No. 516870/2020, dated Jul. 11, 2023.

Office Action in Chinese Appl. No. 201880061656.0, dated Oct. 18, 2023.

Notice of Allowance in U.S. Appl. No. 17/763,485, dated Dec. 5, 2023.

Office Action in counterpart Chinese Appl. No. 201980072797.7, dated Jan. 31, 2024.

Office Action in Japanese Appl. No. 2022-519406, dated Mar. 12, 2024.

Translation of communication dated Oct. 2, 2024 issued by the State Intellectual Property Office of the P.R.China in application No. 201980072797.7.

Translation of Office Action issued in Chinese Appl. No. CN 202080076880.4, dated Oct. 8, 2024.

United States Office Action dated Dec. 27, 2024 in U.S. Appl. No. 18/619,777.

* cited by examiner

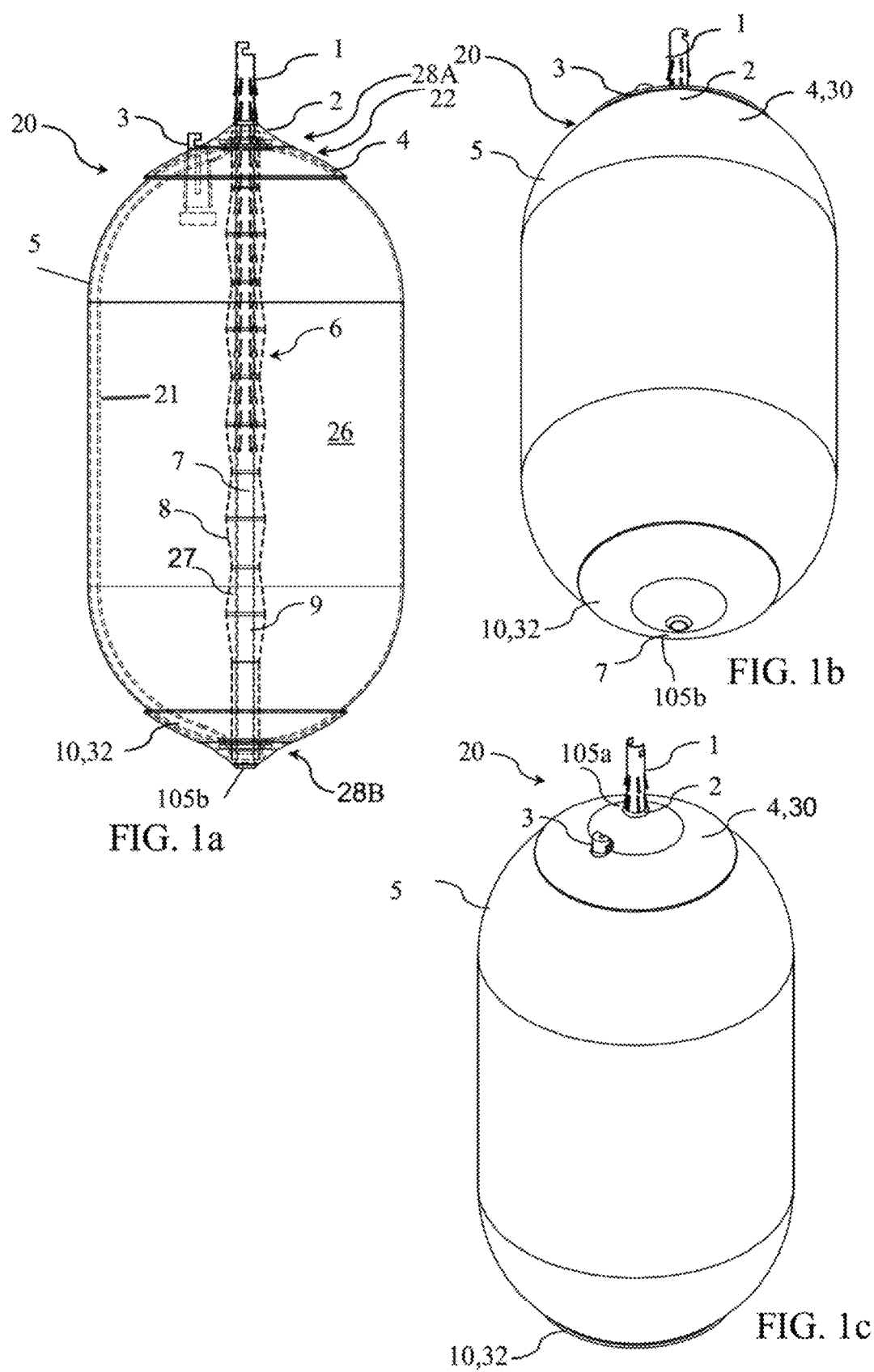

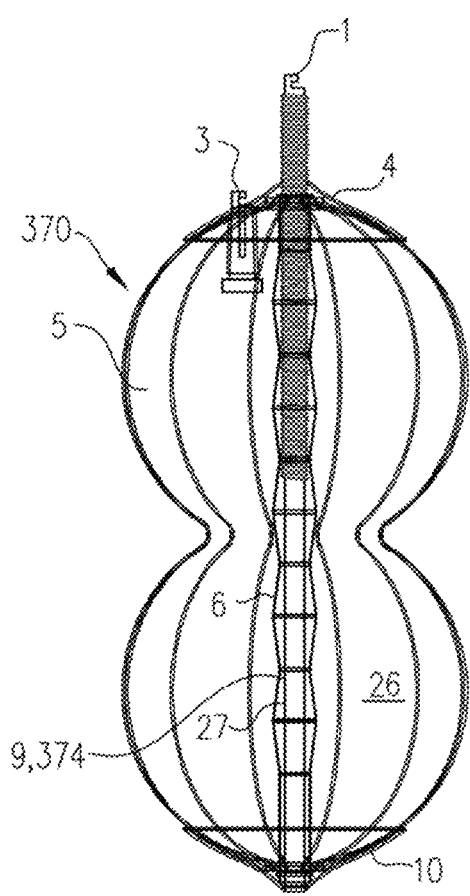
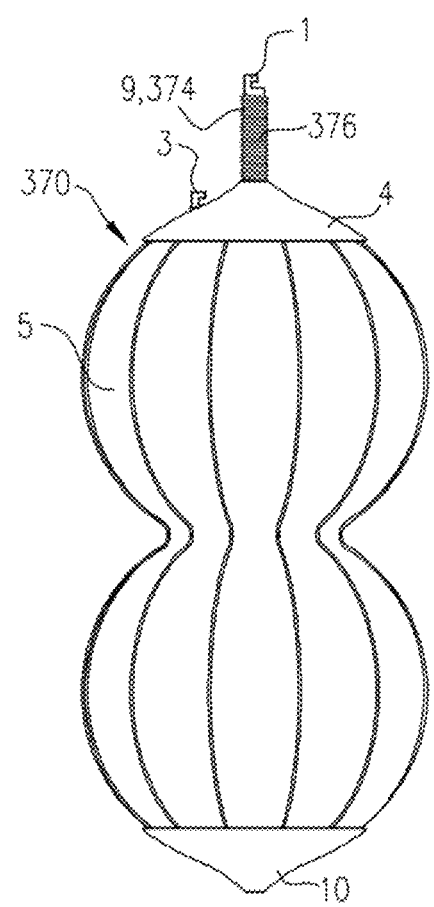
FIG. 6A
FIG. 6B

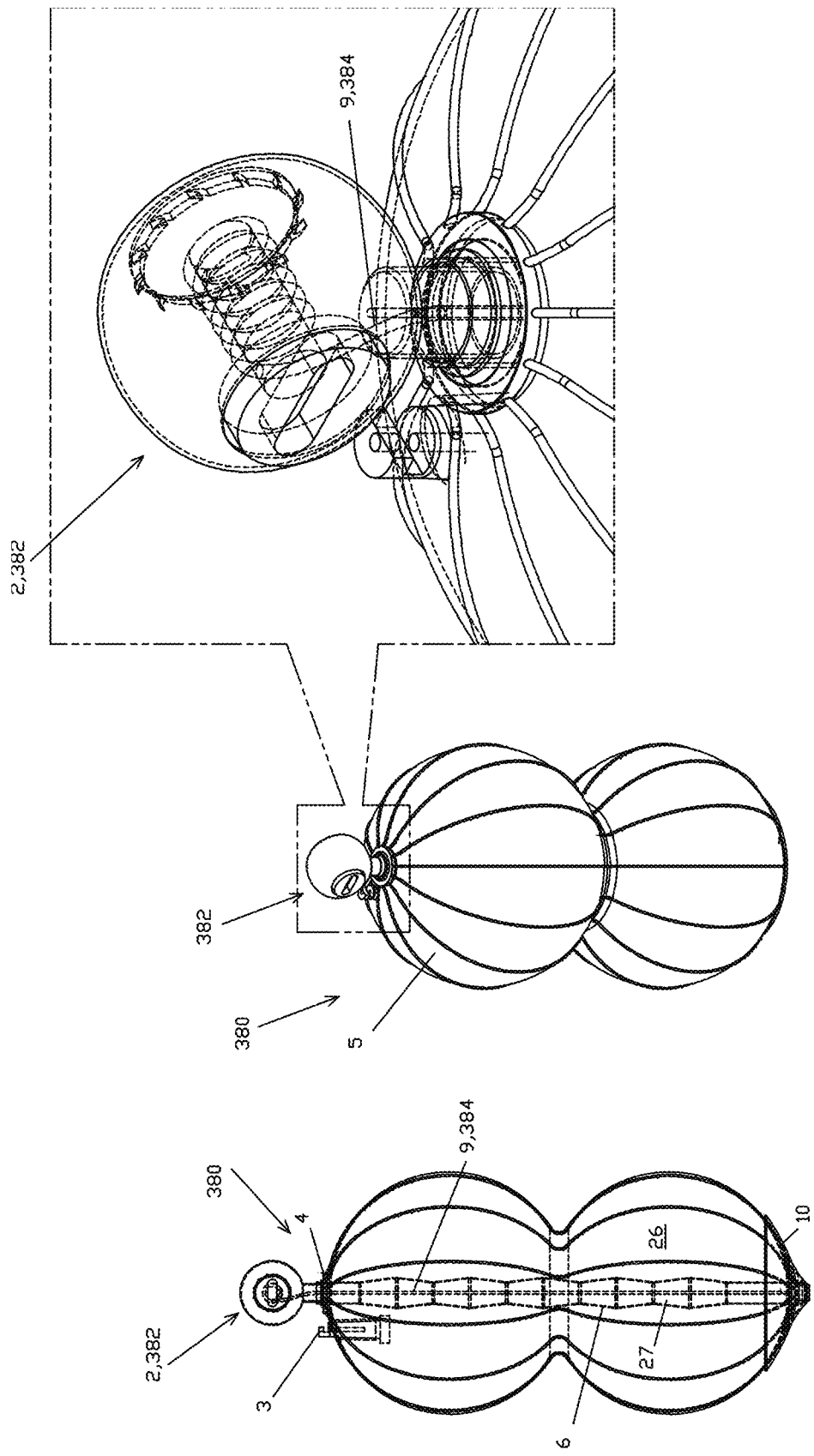

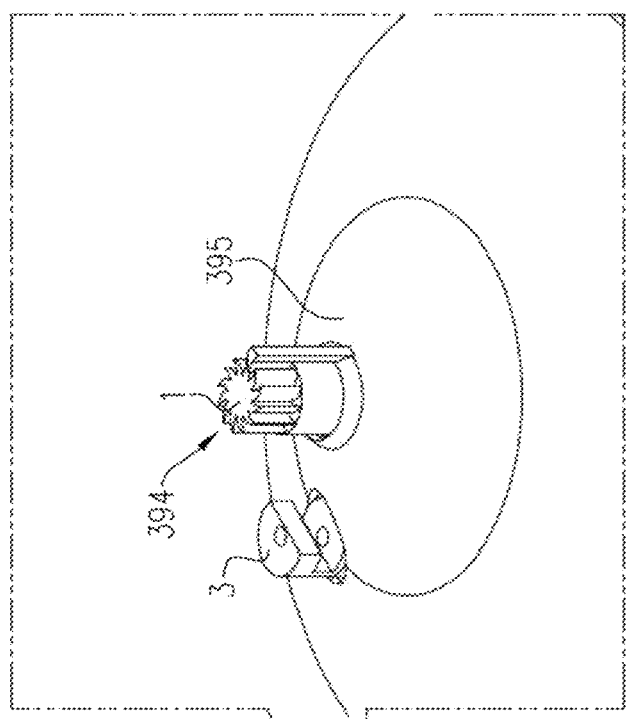
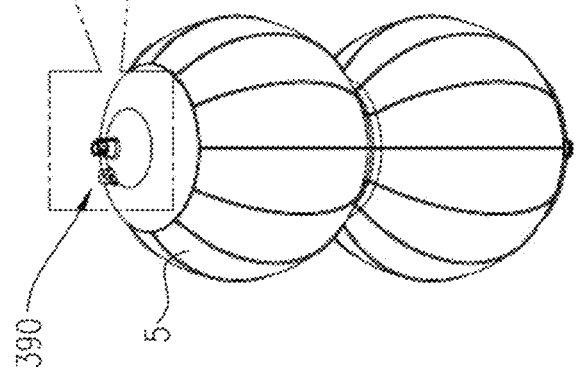
FIG. 6F
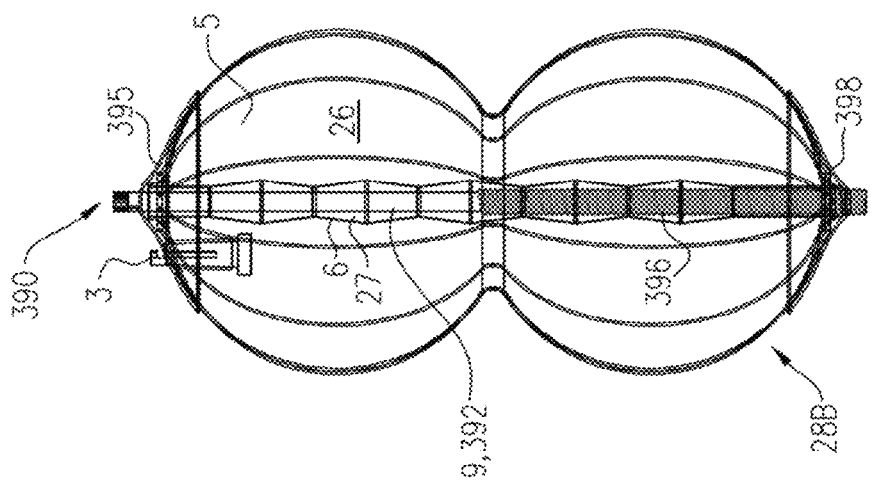
FIG. 6E

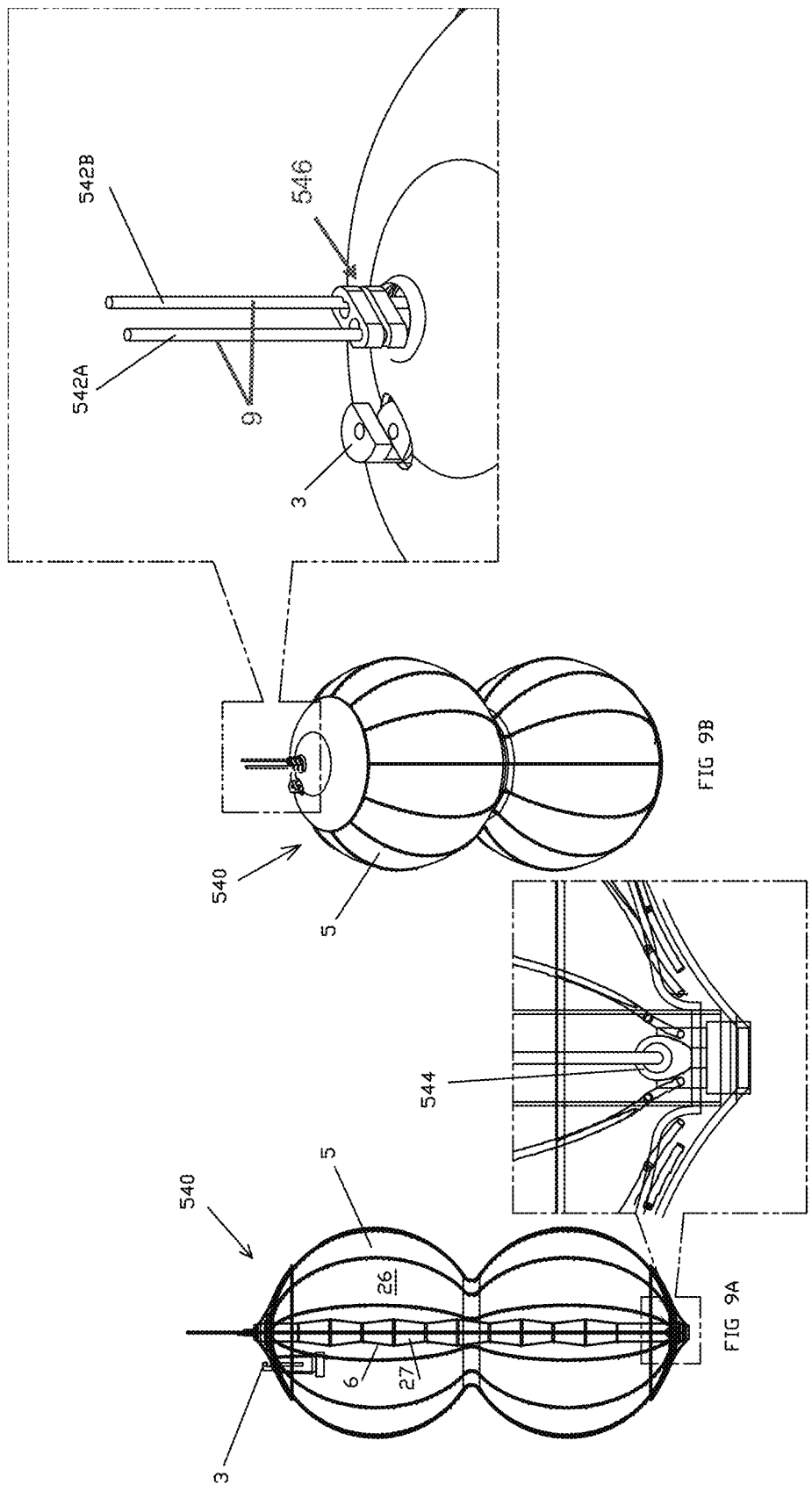

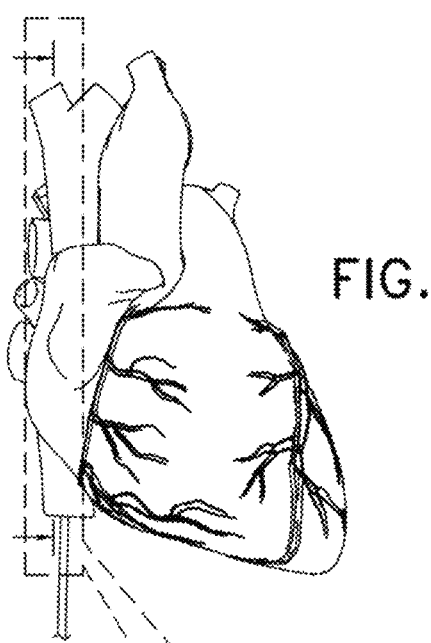
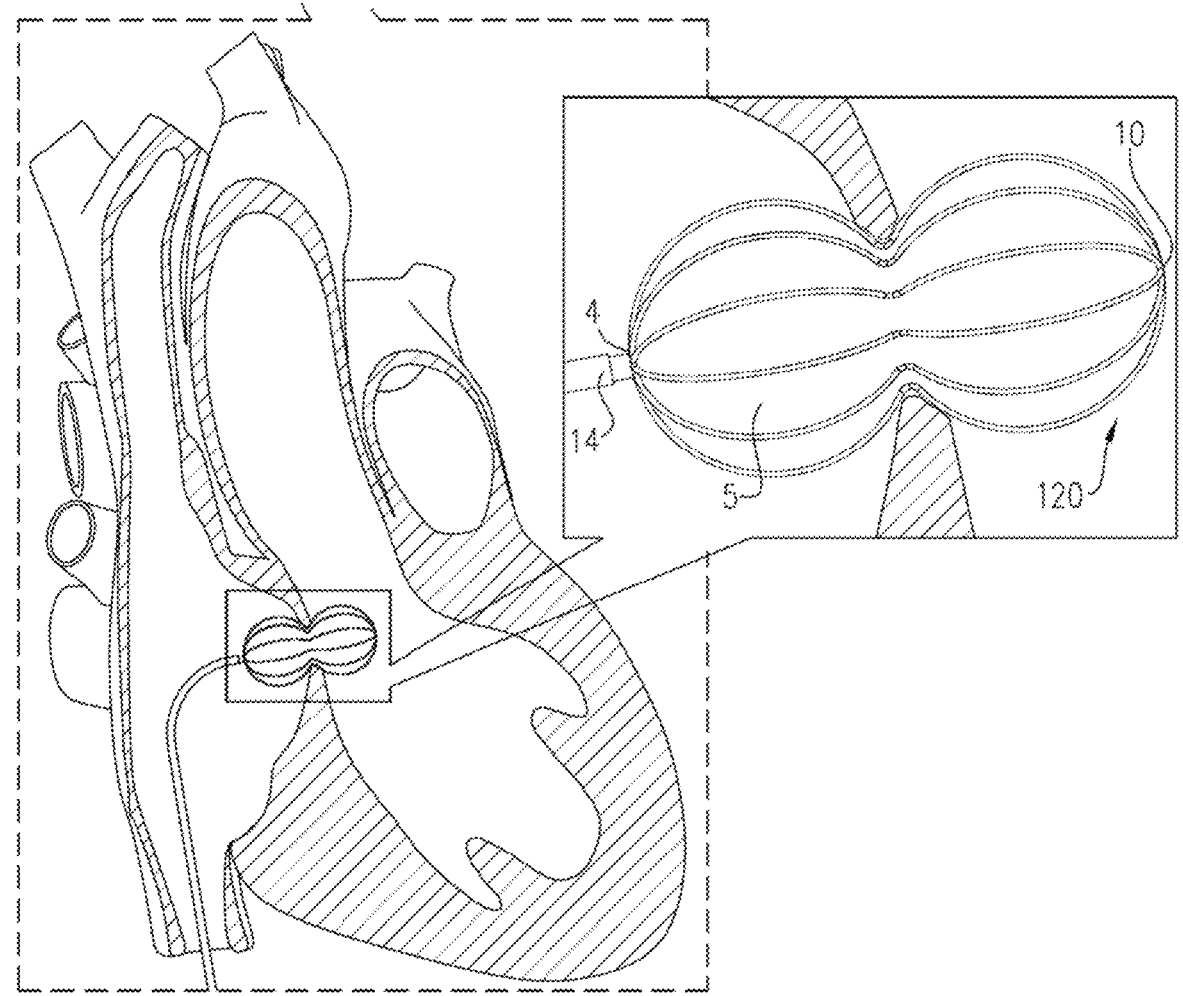
FIG. 11A

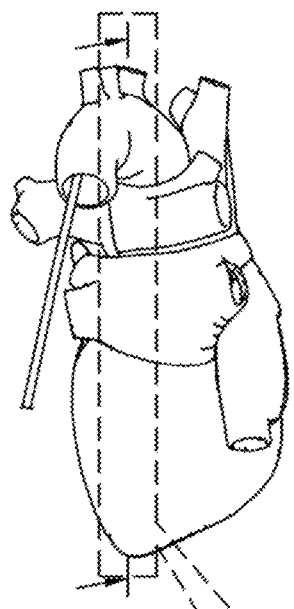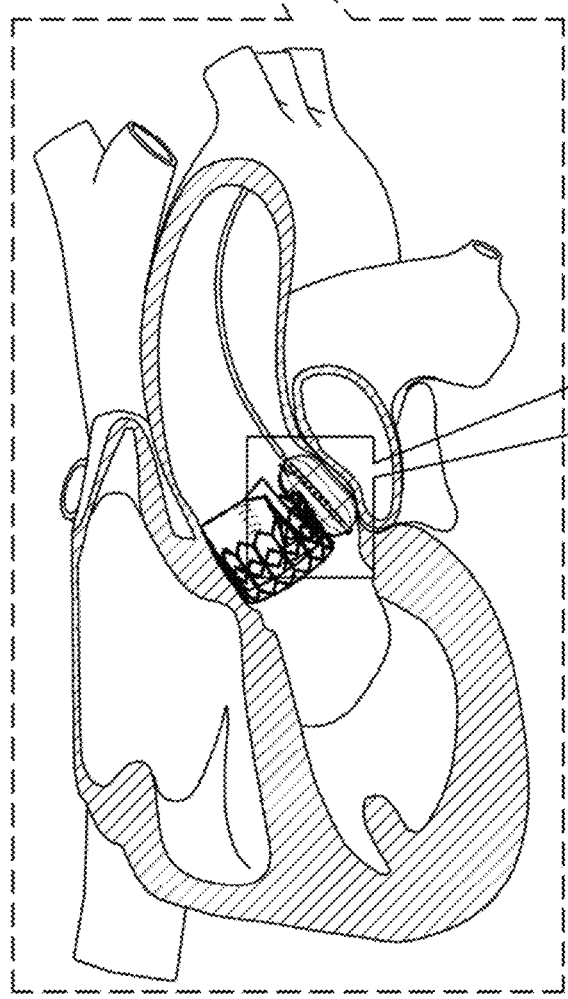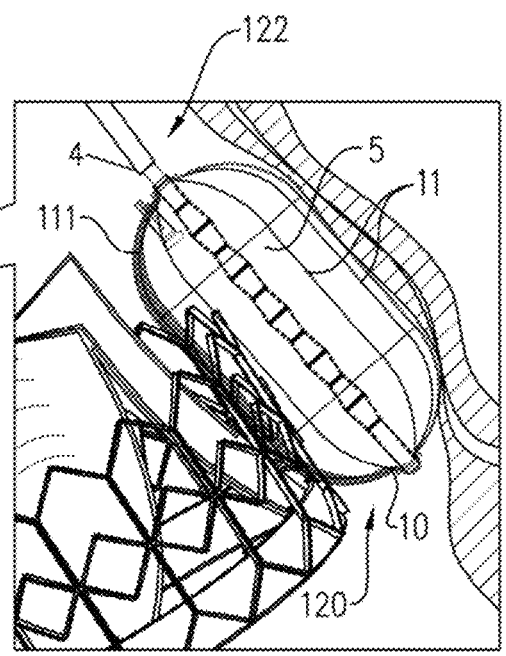
FIG. 13B

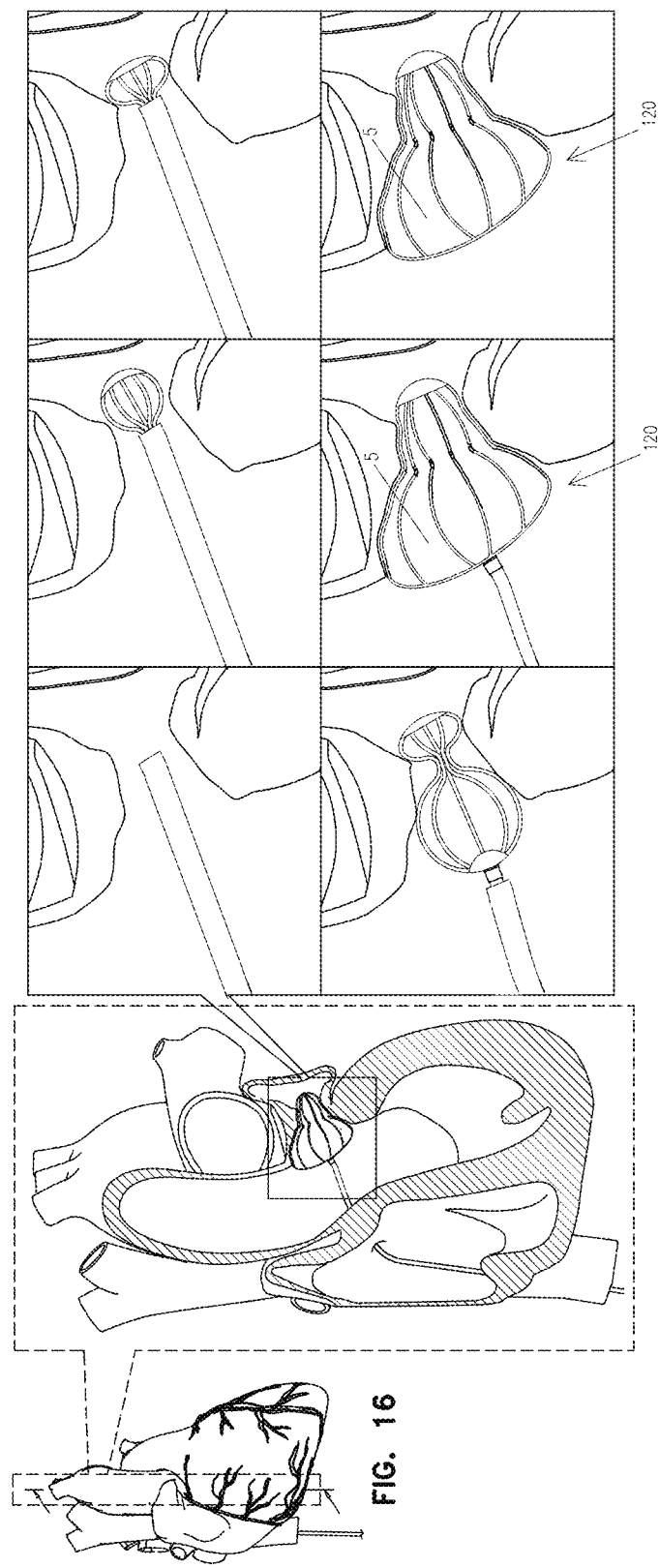

MEDICAL OCCLUSION DEVICE

CROSS-REFERENCE TO RELATED APPLICATIONS

The present patent application is:
(a) a continuation of International Application PCT/US2019/024065, filed Mar. 26, 2019, which published as PCT Publication WO 2020/060587 to Maisano et al., which is a continuation-in-part of International Application PCT/EP2018/075716, filed Sep. 23, 2018, which published as PCI Publication WO 2019/057950 to Maisano et al., and
(b) a continuation-in-part of U.S. application Ser. No. 16/649,777, filed Mar. 23, 2020, which published as US Patent Application Publication 2020/0275935, now U.S. Pat. No. 11,517,319, which is the U.S. national stage of PCT/EP2018/075716, filed Sep. 23, 2018, which claims priority from European Appl. No. 17192792.4, filed Sep. 23, 2017, which published as European Patent Application Publication 3 459 469 A1.

All of the above-mentioned applications are assigned to the assignee of the present application and incorporated herein by reference.

FIELD OF THE APPLICATION

The present invention generally relates to an occlusion device for occluding a cardiovascular defect or a gap between a medical device and adjacent body tissue.

BACKGROUND OF THE APPLICATION

There are several types of unnecessary or even pathologic passageways within the body. If located in blood vessels or in the heart, such passageways can cause a highly undesirable alteration of blood flow or the bypass of blood flow around an organ.

WO 95/32018 describes a method and a device for blocking a body passageway by inserting an expandable frame into the passageway and expanding the frame with an expandable balloon to partially embed the frame in the walls of the passageway. The frame can be provided with a separate sealing membrane, or the balloon can function as the sealing membrane. The balloon can be removed along with the inflation tube after the expansion step if it is not serving as the sealing membrane, or the balloon can be detached from the inflation tube and left in place, either as a sealing membrane or simply to lock the frame in place. The frame can be maintained in its expanded state by being plastically deformed during the expansion step. The expandable frame has substantially cylindrical shape and is described as being suitable, e.g., for closing a patent ductus arteriosus, in which an unwanted passageway or duct connects the aorta to the main pulmonary artery, close to the heart.

U.S. Pat. No. 4,836,204 describes a device for effecting closure of a perforation in the septum of the heart. The device comprises a double-balloon septal defect occlusion catheter which is to be inserted such that the two initially deflated balloons are positioned on opposing sides of the septum. Upon inflating, the balloons snugly engage the respective septum wall sections and thereby prevent leakage through the perforation.

Paravalvular leak is a common complication that occurs in up to 30% of patients undergoing implantation of either surgical or transcatheter prostheses. The option to treat these defects percutaneously may offers safer solution for high-risk patients, without exposing them to risk related to open heart reoperation. However, the currently used devices are suboptimal since they have not been specifically developed with this intended use. Today, paravalvular leak closure is generally accomplished with devices originally designed for occlusion of congenital heart defects. They are usually implanted in a low-flow environment such as patent foramen ovale or atrial septum defect, and in simple geometries. In contrast, paravalvular leaks develop in high pressure and flow environment, and they are characterized by complex geometry. The detect is often crescent or oval shaped, which may include a tubular section with several deformities, and the structure is marginally compliant at best.

The left atrial appendage (LAA) is a cavity that presents in the left atrium of the heart. In patients with atrial fibrillation the passage and steadiness of blood within this cavity can cause thrombus formation, which increase the risk of stroke. Percutaneous LAA occlusion is a therapy for the prevention of stroke in patients with atrial fibrillation. LAA occlusion is used as an alternative to, or in combination with, oral anticoagulant therapy. LAA occlusion has favorable clinical outcomes, but commercially-available devices are typically self-expandable, and not designed to adapt to the anatomy, thus sometimes resulting in complications or suboptimal outcomes. In these environments, some of the currently available occlusion devices are limited by the poor adaptability of the device to the defect (lack of conformability) and by a lack of intra-device sealing (due to the high flow environment).

Nevertheless, there are some concepts and implementations of occlusion devices that were specifically designed for paravalvular leak occlusion or LAA occlusion.

US 2014/0277426 A1 describes various devices for occluding a gap between a medical device and adjacent body tissue. The devices generally comprise a conformable body with a hollow interior and provided with a fluid port intended to supply a pressurizing fluid to inflate the conformable body. Various shapes and constitutions of the conformable body, delivery means and fixing means are described.

U.S. Pat. No. 7,628,805 generally describes a multitude of concepts for locating and for repairing paravalvular leaks. The concepts include sealing stents and also multicomponent and radiation-cured adhesive compounds.

US 2012/078295 describes an occluder device for closing a passage in a circulatory system. The device comprises an expandable fixation unit for fixing the occluder on the passage, which is achieved by switching between a compact form and an expanded form.

In spite of the above, there is still a need for an improved occlusion device which avoids the shortcomings of presently known devices.

SUMMARY OF THE APPLICATION

In some applications of the present invention, an occlusion device is provided for occluding a cardiovascular defect or a gap between a medical device and adjacent body tissue. The occlusion device is for use with a guidewire and a delivery system. The occlusion device comprises:
 a compliant balloon defining a fluid-tight balloon chamber, having a balloon lumen forming a longitudinal passage from a proximal side to a distal side of the balloon, and comprising an inflation port for filling and unfilling a fluid into and from the balloon chamber;

a distal tip element disposed at the distal side of the balloon, and a proximal base element disposed at the proximal side of the balloon;

an elongate actuating element disposed longitudinally slidable in the balloon lumen, connected to the distal tip element, and longitudinally moveable with respect to the proximal base element so as to set a distance between the distal tip element and the proximal base element; typically, the elongate actuating element is selected from the group consisting of: a tube, a wire, a shaft, a cable, a strand, and a fiber;

a locking mechanism for maintaining, between the distal tip element and the proximal base element, the distance set using the elongate actuating element; and a proximal connection element that is disposed at the proximal side of the balloon and is configured to releasably connect the occlusion device to a correspondingly configured distal connection element of the delivery system.

According to another aspect, there is provided an occlusion system comprising an occlusion device as described above and a delivery system (comprising a catheter device) cooperating therewith. The catheter device comprises an implant catheter tube connected to an operating handle. The implant catheter tube comprises a longitudinal passageway for a guidewire, a distal connection element for releasably connecting the catheter device to a correspondingly configured proximal connection element of the occlusion device, and a fluid transfer system releasably connectable to a corresponding inflation port of the occlusion device. The distal connection element and the proximal connection element are generally configured as cooperating members disposed, respectively, at the distal end of the catheter device and at the proximal end of the occlusion device. Examples for such cooperating members comprise cooperating threads, bayonets, or snap connections.

Clinical indications include but are not limited to paravalvular leak (PVL), patent foramen ovale (PFO), atrial septum defect (ASD), ventricular septum defect (VSD), intravalvular leak (IVL), intraleaflet leak, leaflet perforation, type I endovascular leaks after vascular graft implant, left or right heart apex closure after transapical therapeutic access, and left atrial appendage occlusion.

The occlusion device is designed to be delivered into the region to be treated in its longitudinally extended form, either entirely or partially compressed. After delivery, the occlusion device is adapted to the landing zone anatomy by inflating the balloon and subsequently shortening of the longitudinal dimension of the frame formed between the proximal base element and the distal tip element. Under the influence of internal pressure, the balloon will assume a certain volume which, for a given longitudinal frame dimension, results in a certain lateral or radial dimension, which provides a good seal between the balloon and the adjacent anatomy or implanted medical device. Changing the longitudinal frame dimension by selecting a different distance between the distal tip element and the proximal base element will lead to a corresponding change in the radial or lateral extension of the balloon. In other words, shortening the distance between the distal tip element and the proximal base element leads to a corresponding increase in radial or lateral extension under otherwise constant conditions, which improves the seal with the adjacent tissue and/or medical device and seals unwanted blood passage. The lateral extension of the balloon is not necessarily symmetric, either because the balloon is not necessarily symmetric and/or because the anatomy against which the balloon is laterally expanded may cause asymmetric balloon expansion. The radial or lateral expansion together include within their scope one or more directions generally perpendicular to the longitudinal axis of the balloon. (Optionally, the balloon is partially inflated (e.g., to atmospheric pressure) and the longitudinal dimension of the frame is shortened; the balloon may subsequently be further inflated before release, such as if necessary to make the good seal between the balloon and the adjacent anatomy or implanted medical device.)

In the context of the present disclosure, the terms "distal" and "proximal" are used accordingly to their standard meaning in the field of percutaneous cardiovascular devices. The term "proximal" refers to those components of the device assembly which, when following a delivery catheter during percutaneous delivery, are closer to the end of the catheter that is configured for manipulation by the user (e.g., catheter handle manipulated by a physician). The term "distal" is used to refer to those components of the device assembly that are more distant from the end of the catheter that is configured for manipulation by the user and/or that are inserted further into the body of a patient. Accordingly, in an occlusion device for use in a gap between a medical device and the adjacent body tissue, like a paravalvular mitral leak, the proximal end may face towards the left atrium and the distal end may face towards the left ventricle, when the occlusion device is deployed in the defect using a transseptal approach.

The term "compliant" used in relation with balloons or with structural components shall be understood as implying a deformability that substantially follows an applied force. Accordingly, a "compliant balloon" shall be understood as a balloon which progressively expands under the effect of increasing radial pressure as long as a certain burst pressure is not exceeded.

The term "strut" shall be understood as an elongate structural element which can be formed e.g. as a thin wire, rod, thick-walled tube, all of which do not necessarily have a circular cross section.

The compliant balloon of the occlusion device is not necessarily pre-shaped since the balloon, because it is compliant, takes the shape of the defect once inflated within the defect. However, for some applications, the wall of the balloon has a different thickness in a specific area (e.g., centrally, such that the balloon assumes a figure-eight shape upon inflation, or longitudinally on one side, to create a backbone that causes the balloon to inflate less on that side). In addition, pre-shaped balloons can be used to establish a predetermined, non-uniform local resilience against an applied radial pressure.

For some applications, the balloon comprises silicone, polyurethane, polytetrafluoroethylene (PTFE), polymethylmethacrylate, polyether ether ketone (PEEK), polyvinyl chloride, polyethylene terephthalate, nylon, polyamide, polyamide, polyether block amide (PEBA), or another biocompatible material. For some applications, the balloon comprises a compliant, biodegradable material selected from polycaprolactone (PCL), polyglycolic acid (PGA), polylactic acid (PIA), and polydioxanone (PDO or PDS). Optionally, the balloon is treated externally with a hydrophilic coating, hydrophobic coating, an anti-inflammatory coating, anticoagulation coating, or other coating to promote endothelial growth, such as chemically or by modifying the porosity of the external surface of the balloon.

For some applications, the proximal base element and the distal tip element are connected by one or more struts. Depending on the specific application, various configurations of the struts may be contemplated. According to one application, the struts comprise a single connecting strut disposed within the balloon lumen or outside the balloon. For other applications, the struts comprise a plurality of struts, e.g., disposed in a cage-like manner outside the balloon. Applying internal pressure to the balloon will lead to inflation thereof against a resilient force of the compliant balloon material and also against the structural limitation provided by the plurality of external connecting struts. In particular, such a configuration may offer the advantage of an improved stability of the compliant balloon against unwanted local deformation. This will generally result in an improved adaptation of the occlusion device to the geometry of the defect to be occluded.

The locking mechanism for maintaining a predetermined distance between the distal tip element and the proximal base element may also be configured in various manners. For example, the locking mechanism may comprise a rotatable elongate actuating element (e.g., a wire) with a threaded portion formed to cooperate with a corresponding section formed in the proximal base element. For some applications, the locking mechanism is configured as a ratchet mechanism such that the distance between the distal tip element and the proximal base element is selectable from a range of distances. This allows for precise and reliable definition of the radial extension of the occlusion device and accordingly to improved reliability of the occlusion device.

The elongate actuating element is disposed longitudinally slidable in the balloon lumen, connected to the distal tip element and longitudinally slidable with respect to the proximal base element so as to set a distance between the distal tip element and the proximal base element. For this purpose, the elongate actuating element is typically formed as an elongate, flexible member with a smooth surface. For some applications, the elongate actuating element is configured as actuating wire. The use of actuating wires is well established in the field of cardiovascular interventions. In the present context, the use of a wire together with appropriate proximal counterpieces allows for simple, precise and reproducible selection of the distance between the distal tip element and the proximal base element.

Means for filling and unfilling balloons and other inflatable devices are also well known in the field of cardiovascular interventions. For some applications, the balloon has an inflation port configured as a self-closing valve when it is not connected to a corresponding fluid transfer system of the delivery system. In particular, this allows filling the balloon through a longitudinal fluid line which can subsequently be disconnected and retracted and which only needs to be reinserted and reconnected if an additional filling or an unfilling of the balloon is needed.

The aforementioned elements as well as those claimed and described in the following and to be used according to the invention, shall generally be understood with their meaning as established in the field of medicine.

There is therefore provided, in accordance with an Inventive Concept 1 of the present invention, apparatus for occluding a cardiovascular defect or a gap between a medical device and adjacent body tissue, the apparatus for use with a guidewire and a delivery system, the apparatus including:
an occlusion device including:
a compliant balloon (a) defining a fluid-tight balloon chamber, (b) having a balloon lumen forming a longitudinal passage from a proximal side to a distal side of the balloon, and (c) including an inflation port for filling and unfilling a fluid into and from the balloon chamber;
a distal tip element disposed at the distal side of the balloon, and a proximal base element disposed at the proximal side of the balloon;
a locking mechanism; and
a proximal connection element that is disposed at the proximal side of the balloon and is configured to releasably connect the occlusion device to a correspondingly configured distal connection element of the delivery system; and
an elongate actuating element disposed longitudinally slidable in the balloon lumen, connected to the distal tip element, and longitudinally moveable with respect to the proximal base element so as to set a distance between the distal tip element and the proximal base element,
wherein the locking mechanism is configured to maintain, between the distal tip element and the proximal base element, the distance set using the elongate actuating element.

Inventive Concept 2. The apparatus according to Inventive Concept 1, wherein the elongate actuating element is selected from the group consisting of: a tube, a wire, a shaft, a cable, a strand, and a fiber.

Inventive Concept 3. The apparatus according to Inventive Concept 1, wherein the distal tip element and the proximal base element are shaped so as to define respective guidewire openings substantially coaxial to the balloon lumen for slidingly receiving therein the guidewire.

Inventive Concept 4. The apparatus according to Inventive Concept 1, wherein the proximal base element and the distal tip element include a proximal disk and a distal disk, respectively.

Inventive Concept 5. The apparatus according to Inventive Concept 1, wherein the locking mechanism is disposed at the proximal side of the balloon.

Inventive Concept 6. The apparatus according to Inventive Concept 5, wherein the locking mechanism is connected to or integrated into the proximal base element.

Inventive Concept 7. The apparatus according to Inventive Concept 1, wherein the compliant balloon includes a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 8. The apparatus according to any one of Inventive Concepts 1-7, further including at least one connecting strut fixed to the distal tip element and to the proximal base element.

Inventive Concept 9. The apparatus according to Inventive Concept 8, wherein the at least one connecting strut includes a single connecting strut disposed inside or outside the balloon.

Inventive Concept 10. The apparatus according to Inventive Concept 8, wherein the at least one connecting strut includes a plurality of connecting struts disposed inside or outside the balloon.

Inventive Concept 11. The apparatus according to Inventive Concept 10, wherein the plurality of connecting struts are disposed in a cage-like arrangement.

Inventive Concept 12. The apparatus according to Inventive Concept 10, wherein the plurality of connecting struts are arranged as a frame.

Inventive Concept 13. The apparatus according to any one of Inventive Concepts 1-7, wherein the occlusion device includes the elongate actuating element, which is fixedly connected to the distal tip element.

Inventive Concept 14. The apparatus according to Inventive Concept 13, wherein the elongate actuating element is longitudinally slidable with respect to the proximal base element.

Inventive Concept 15. The apparatus according to Inventive Concept 13, wherein the locking mechanism includes one or more pawls and the elongate actuating element includes a plurality of teeth, so as to together provide a ratchet mechanism such that the distance between the distal tip element and the proximal base element is selectable from a range of distances by distally pulling the elongate actuating element through the locking mechanism.

Inventive Concept 16. The apparatus according to Inventive Concept 13, wherein the elongate actuating element includes the wire.

Inventive Concept 17. The apparatus according to Inventive Concept 13,
wherein the elongate actuating element is shaped so as to define a thread,
wherein the locking mechanism includes a threaded opening defined by the proximal base element, wherein the thread of the elongate actuating element is disposed within the threaded opening, and
wherein the occlusion device is configured such that rotation of the elongate actuating element with respect to the proximal base element causes the elongate actuating element to longitudinally move with respect to the proximal base element, thereby setting the distance between the distal tip element and the proximal base element and maintaining the set distance.

Inventive Concept 18. The apparatus according to any one of Inventive Concepts 1-7, wherein the elongate actuating element is releasably connected to the distal tip element.

Inventive Concept 19, The apparatus according to Inventive Concept 18,
wherein the occlusion device further includes a locking elongate element fixed to the distal tip element and longitudinally slidable with respect to the proximal base element, and
wherein the locking mechanism is configured to lock the locking elongate element with respect to the proximal base element in order to maintain the distance set using the elongate actuating element.

Inventive Concept 20. The apparatus according to Inventive Concept 19, wherein the locking elongate element is selected from the group consisting of: a tube, a wire, a shaft, a cable, a strand, and a fiber.

Inventive Concept 21. The apparatus according to Inventive Concept 20, wherein the locking elongate element is the wire.

Inventive Concept 22. The apparatus according to Inventive Concept 18, wherein the elongate actuating element is longitudinally slidable with respect to the proximal base element.

Inventive Concept 23, The apparatus according to Inventive Concept 22,
wherein a distal portion of the elongate actuating element is shaped so as to define a thread, and
wherein the distal tip element is shaped so as to define a threaded opening to which the thread of the distal portion of the elongate actuating element is releasably threadingly connected, such that the elongate actuating element is releasably connected to the distal tip element.

Inventive Concept 24, The apparatus according to Inventive Concept 18,
wherein the elongate actuating element is shaped so as to define a thread,
wherein the proximal base element is shaped so as to define a threaded opening, wherein the thread of the elongate actuating element is disposed within the threaded opening, and
wherein the occlusion device is configured such that rotation of the elongate actuating element with respect to the proximal base element causes the elongate actuating element to longitudinally move with respect to the proximal base element, thereby setting the distance between the distal tip element and the proximal base element and maintaining the set distance.

Inventive Concept 25. The apparatus according to Inventive Concept 24,
wherein a distal portion of the elongate actuating element includes a first positive connection element,
wherein the distal tip element is shaped so as to define a second positive connection element, and
wherein the first positive connection element is releasably connected to the second positive connection element, such that the elongate actuating element is releasably connected to the distal tip element.

Inventive Concept 26. The apparatus according to any one of Inventive Concepts 1-7, wherein the inflation port includes a self-closing valve.

Inventive Concept 27. The apparatus according to Inventive Concept 26, wherein the inflation port is releasably connected to the delivery system, and wherein the self-closing valve is configured to close upon disconnection of the inflation port from the delivery system.

Inventive Concept 28. The apparatus according to any one of Inventive Concepts 1-7, wherein the balloon has an average wall thickness of between 100 and 5000 microns.

29. The apparatus according to any one of Inventive Concepts 1-28, wherein the balloon has, at a thinnest portion of a wall of the balloon, a thinnest wall thickness of between 20 and 500 microns.

Inventive Concept 30. The apparatus according, to any one of inventive Concepts 1-29, wherein the occlusion device further includes a proximal radiopaque marker that is fixed to the proximal base element and includes a material that is more radiopaque than the proximal base element.

Inventive Concept 31. The apparatus according to any one of Inventive Concepts 1-29, wherein the occlusion device further includes a distal radiopaque marker that is fixed to the distal tip element and includes a material that is more radiopaque than the distal tip element.

Inventive Concept 32. The apparatus according to any one of Inventive Concepts 1-29,
wherein the occlusion device further includes a proximal radiopaque marker that is fixed to the proximal base element and includes a material that is more radiopaque than the proximal base element, and
wherein the occlusion device further includes a distal radiopaque marker that is fixed to the distal tip element and includes a material that is more radiopaque than the distal tip element.

Inventive Concept 33. An occlusion system including the apparatus according to any one of Inventive Concepts 1-32, the occlusion system further including an implant catheter, in which the occlusion device is releasably disposed in a compressed form, in which a greatest distance between the proximal base element and the distal tip element is between 8 and 80 mm.

Inventive Concept 34. An occlusion system including the apparatus according to any one of Inventive Concepts 1-33, the occlusion system further including, the delivery system cooperating therewith, the delivery system including an implant catheter connected to an operating handle, the implant catheter including a longitudinal passageway for the guidewire, a distal connection element for releasably connecting the implant catheter to the correspondingly configured proximal connection element of the occlusion device, and an inflation tube channel releasably connectable to the corresponding inflation port of the occlusion device.

There is further provided, in accordance with an Inventive Concept 35 of the present invention, apparatus for occluding a cardiovascular defect or a gap between a medical device and adjacent body tissue, the apparatus for use with a guidewire and a delivery system, the apparatus including an occlusion device, which includes:
  a compliant balloon defining a fluid-tight balloon chamber and including an inflation port for filling and unfilling a fluid into and from the balloon chamber;
  a distal tip element disposed at a distal side of the balloon, and a proximal base element disposed at a proximal side of the balloon;
  an elongate element having a fixed length, and fixed to the distal tip element and the proximal base element so as to set a fixed distance between the distal tip element and the proximal base element; and
  a proximal connection element that is disposed al the proximal side of the balloon and is configured to releasably connect the occlusion device to a correspondingly configured distal connection element of the delivery system.

Inventive Concept 36. The apparatus according to Inventive Concept 35, wherein the elongate element is selected from the group consisting of: a tube, a wire, a shaft, a cable, a strand, and a fiber.

Inventive Concept 37. The apparatus according to Inventive Concept 35, wherein the proximal base element and the distal tip element include a proximal disk and a distal disk, respectively.

Inventive Concept 38. The apparatus according to Inventive Concept 35, wherein the compliant balloon includes a compliant material selected from the group consisting of: polycaprolactone (PCL), polyglycolic acid (PGA), polylactic acid (PLA), polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 39. The apparatus according to any one of Inventive Concepts 35-38, wherein the balloon has a balloon lumen forming a longitudinal passage from the proximal side to the distal side of the balloon.

Inventive Concept 40. The apparatus according to Inventive Concept 39, wherein the elongate element is disposed in the balloon lumen.

Inventive Concept 41. The apparatus according to Inventive Concept 39, wherein the distal tip element and the proximal base element are shaped so as to define respective guidewire openings substantially coaxial to the balloon lumen for slidingly receiving therein the guidewire.

Inventive Concept 42. The apparatus according to any one of Inventive Concepts 35-38, further including at least one connecting strut fixed to the distal tip element and to the proximal base element.

Inventive Concept 43. The apparatus according to Inventive Concept 42, wherein the at least one connecting strut includes a single connecting strut disposed inside or outside the balloon.

Inventive Concept 44. The apparatus according to Inventive Concept 42, wherein the at least one connecting strut includes a plurality of connecting struts disposed inside or outside the balloon.

Inventive Concept 45. The apparatus according to Inventive Concept 44, wherein the plurality of connecting struts are disposed in a cage-like arrangement.

Inventive Concept 46. The apparatus according to Inventive Concept 44, wherein the plurality of connecting struts are arranged as a frame.

Inventive Concept 47. The apparatus according to any one of inventive Concepts 35-38, wherein the inflation port includes a self-closing valve.

Inventive Concept 48. The apparatus according to Inventive Concept 47, wherein the inflation port is releasable connected to the delivery system, and wherein the self-closing valve is configured to close upon disconnection of the inflation port from the delivery system.

Inventive Concept 49. The apparatus according to any one of Inventive Concepts 35-38, wherein the balloon has an average wall thickness of between 100 and 5000 microns.

Inventive Concept 50. The apparatus according to any one of Inventive Concepts 35-49, wherein the balloon has, at a thinnest portion of a wall of the balloon, a thinnest wall thickness of between 20 and 500 microns.

Inventive Concept 51. The apparatus according to any one of Inventive Concepts 35-50, wherein the occlusion device further includes a proximal radiopaque marker that is fixed to the proximal base element and includes a material that is more radiopaque than the proximal base element.

Inventive Concept 52. The apparatus according to any one of Inventive Concepts 35-50, wherein the occlusion device further includes a distal radiopaque marker that is fixed to the distal tip element and includes a material that is more radiopaque than the distal tip element.

Inventive Concept 53. The apparatus according to any one of Inventive Concepts 35-50,
  wherein the occlusion device further includes a proximal radiopaque marker that is fixed to the proximal base element and includes a material that is more radiopaque than the proximal base element, and
  wherein the occlusion device further includes a distal radiopaque marker that is fixed to the distal tip element and includes a material that is more radiopaque than the distal tip element.

Inventive Concept 54. An occlusion system including the apparatus according to any one of Inventive Concepts 35-53, the occlusion system further including an implant catheter, in which the occlusion device is releasably disposed in a compressed form, in which a greatest distance between the proximal base element and the distal tip element is between 8 and 80 mm.

Inventive Concept 55. An occlusion system including the apparatus according to any one of Inventive Concepts 35-54, the occlusion system further including the delivery system cooperating therewith, the delivery system including an implant catheter connected to an operating handle, the implant catheter including a longitudinal passageway for the guidewire, a distal connectional element for releasably connecting the implant catheter to the correspondingly configured proximal connection element of the occlusion device, and an inflation tube channel releasably connectable to the corresponding inflation port of the occlusion device.

There is still further provided, in accordance with an Inventive Concept 56 of the present invention, a method of occluding a cardiovascular defect or a gap between a medical device and adjacent body tissue of a patient, the method including:

advancing a guidewire into a body of the patient using a delivery system;

using the delivery system, positioning a compliant balloon of an occlusion device in a longitudinally extended form thereof in the cardiovascular defect or the gap to be occluded, by advancing the occlusion device over the guidewire;

inflating the compliant balloon by filling, via an inflation port of the balloon, a fluid into a fluid-tight balloon chamber defined by the balloon;

expanding the balloon in a radial or a lateral direction by shortening a distance between a distal tip element and a proximal base element to a desired distance and locking the distance, the distal tip element disposed at the distal side of the balloon, and the proximal base element disposed at the proximal side of the balloon; and releasing the occlusion device from the delivery system.

Inventive Concept 57. The method according to Inventive Concept 56,
wherein the balloon has a balloon lumen forming a longitudinal passage from a proximal side to a distal side of the balloon,
wherein the distal tip element and the proximal base element are shaped so as to define respective guidewire openings substantially coaxial to the balloon lumen for slidingly receiving therein the guidewire, and
wherein advancing the occlusion device over the guidewire includes sliding the guidewire through the guidewire openings.

Inventive Concept 58. The method according to Inventive Concept 56, wherein positioning the compliant balloon in the longitudinally extended form thereof includes positioning the compliant balloon in the longitudinally extended form thereof in the cardiovascular defect.

Inventive Concept 59. The method according to Inventive Concept 56, wherein positioning the compliant balloon in the longitudinally extended form thereof includes positioning the compliant balloon in the longitudinally extended form thereof in the gap between the medical device and the adjacent body tissue.

Inventive Concept 60. The method according to Inventive Concept 59, wherein the medical device is a prosthetic cardiac valve, and wherein the method treats paravalvular leak between the prosthetic cardiac valve and adjacent cardiac tissue of the patient.

Inventive Concept 61. The method according to Inventive Concept 60,
wherein positioning and inflating the compliant balloon include:
positioning the balloon in a ventricle of the patient;
thereafter, partially inflating the balloon;
thereafter, disposing the balloon approximately at a longitudinal center of the paravalvular leak; and
thereafter, further inflating the balloon, and
wherein expanding the balloon includes expanding the balloon after further inflating the balloon.

Inventive Concept 62. The method according to Inventive Concept 61, wherein disposing the balloon approximately at the longitudinal center of the paravalvular leak includes proximally withdrawing the balloon until the balloon is disposed approximately at the longitudinal center of the paravalvular leak.

Inventive Concept 63. The method according to Inventive Concept 56, wherein the method further includes partially inflating the balloon before positioning the balloon in the longitudinally extended form thereof in the cardiovascular detect or the gap to be occluded.

Inventive Concept 64, The method according to Inventive Concept 56, wherein the method further includes, after positioning the balloon in the longitudinally extended form thereof in the cardiovascular defect or the gap to be occluded:
partially inflating the balloon; and
after partially inflating the balloon, repositioning the balloon in the longitudinally extended form thereof in the cardiovascular defect or the gap to be occluded.

Inventive Concept 65. The method according to Inventive Concept 56,
wherein positioning the balloon includes delivering the balloon to the cardiovascular defect or the gap to be occluded while the balloon is disposed within an implant catheter of the delivery system,
wherein the method includes, before inflating the balloon, exposing a portion of the balloon from the implant catheter,
wherein inflating includes inflating the portion of the balloon,
wherein expanding includes expanding the portion of the balloon by shortening the distance between the distal tip element and the proximal base element by moving the distal tip element toward the proximal base element, and
wherein the method further includes, before releasing the occlusion device from the delivery system:
exposing a remainder of the balloon from the implant catheter;
inflating the remainder of the balloon; and
expanding the remainder of the balloon by further shortening the distance between the distal tip element and the proximal base element.

Inventive Concept 66. The method according to Inventive Concept 56, wherein the proximal base element and the distal tip element include a proximal disk and a distal disk, respectively.

Inventive Concept 67. The method according to Inventive Concept 56, wherein the compliant balloon includes a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 68. The method according to Inventive Concept 56, wherein the occlusion device further includes at least one connecting strut fixed to the distal tip element and to the proximal base element.

Inventive Concept 69. The method according to Inventive Concept 68, wherein the at least one connecting strut includes a single connecting strut disposed inside or outside the balloon.

Inventive Concept 70. The method according to Inventive Concept 68, wherein the at least one connecting strut includes a plurality of connecting struts disposed inside or outside the balloon.

Inventive Concept 71. The method according to Inventive Concept 70, wherein the plurality of connecting struts are disposed in a cage-like arrangement.

Inventive Concept 72. The method according to Inventive Concept 70, wherein the plurality of connecting struts are arranged as a frame.

Inventive Concept 73. The method according to Inventive Concept 56,
- wherein the balloon has a balloon lumen forming a longitudinal passage from a proximal side to a distal side of the balloon,
- wherein shortening the distance between the distal tip element and the proximal base element to the desired distance includes distally moving an elongate actuating element disposed longitudinally slidable in the balloon lumen, connected to the distal tip element, and longitudinally moveable with respect to the proximal base element, and
- wherein locking the distance includes using a locking mechanism for maintaining, between the distal tip element and the proximal base element, the distance set using the elongate actuating element.

Inventive Concept 74. The method according to Inventive Concept 73, wherein the elongate actuating element is selected from the group consisting of: a tube, a wire, a shaft, a cable, a strand, and a fiber.

Inventive Concept 75. The method according to Inventive Concept 73, wherein the occlusion device includes the elongate actuating element, which is fixedly connected to the distal tip element.

Inventive Concept 76. The method according to Inventive Concept 75,
- wherein the elongate actuating element is longitudinally slidable with respect to the proximal base element, and
- wherein distally moving the elongate actuating element includes sliding the elongate actuating element through the proximal base element.

Inventive Concept 77. The method according to Inventive Concept 75,
- wherein the locking mechanism includes one or more pawls and the elongate actuating element includes a plurality of teeth, so as to together provide a ratchet mechanism such that the distance between the distal tip element and the proximal base element is selectable from a range of distances by distally pulling the elongate actuating element through the locking mechanism, and
- wherein shortening the distance includes distally pulling the elongate actuating element through the locking mechanism.

Inventive Concept 78. The method according to Inventive Concept 75, wherein the elongate actuating element includes the wire.

Inventive Concept 79. The method according to Inventive Concept 75,
- wherein the elongate actuating element is shaped so as to define a thread,
- wherein the locking mechanism includes a threaded opening defined by the proximal base element, wherein the thread of the elongate actuating element is disposed within the threaded opening, and
- wherein shortening the distance includes rotating the elongate actuating element with respect to the proximal base element such that the elongate actuating element longitudinally moves with respect to the proximal base element, thereby setting the distance between the distal tip element and the proximal base element and maintaining the set distance.

Inventive Concept 80. The method according to Inventive Concept 73, wherein the elongate actuating element is releasably connected to the distal tip element.

Inventive Concept 81, The method according to Inventive Concept 80,
- wherein the occlusion device further includes a locking elongate element fixed to the distal tip element and longitudinally slidable with respect to the proximal base element, and
- wherein locking the distance includes using the locking mechanism to lock the locking elongate element with respect to the proximal base element in order to maintain the distance set using the elongate actuating element.

Inventive Concept 82. The method according to Inventive Concept 81, wherein the locking elongate element is selected from the group consisting of: a tube, a wire, a shaft, a cable, a strand, and a fiber.

Inventive Concept 83. The method according to Inventive Concept 82, wherein the locking elongate element is the wire.

Inventive Concept 84. The method according to Inventive Concept 80,
- wherein the elongate actuating element is longitudinally slidable with respect to the proximal base element, and
- wherein distally moving the elongate actuating element includes sliding the elongate actuating element through the proximal base element.

Inventive Concept 85. The method according to Inventive Concept 84,
- wherein a distal portion of the elongate actuating element is shaped so as to define a thread,
- wherein the distal tip element is shaped so as to define a threaded opening to which the thread of the distal portion of the elongate actuating element is releasably threadingly connected, such that the elongate actuating element is releasably connected to the distal tip element, and
- wherein the method further includes, after distally moving the elongate actuating element, disconnecting the elongate actuating element from the distal tip element.

Inventive Concept 86. The method according to Inventive Concept 80,
- wherein the elongate actuating element is shaped so as to define a thread,
- wherein the proximal base element is shaped so as to define a threaded opening, wherein the thread of the elongate actuating element is disposed within the threaded opening, and
- wherein shortening the distance includes rotating the elongate actuating element with respect to the proximal base element such that the elongate actuating element longitudinally moves with respect to the proximal base element, thereby setting the distance between the distal tip element and the proximal base element and maintaining the set distance.

Inventive Concept 87, The method according to Inventive Concept 86,
- wherein a distal portion of the elongate actuating element includes a first positive connection element,
- wherein the distal tip element is shaped so as to define a second positive connection element, wherein the first positive connection element is releasably connected to the second positive connection element, such that the elongate actuating element is releasably connected to the distal tip element, and wherein the method further includes, after distally moving the elongate actuating element, disconnecting the elongate actuating element from the distal tip element.

Inventive Concept 88. The method according to Inventive Concept 56, wherein the inflation port includes a self-closing valve.

Inventive Concept 89. The method according to Inventive Concept 88, wherein the inflation port is releasably connected to the delivery system, and wherein the self-closing valve is configured to close upon disconnection of the inflation port from the delivery system.

Inventive Concept 90. The method according to Inventive Concept 56, wherein releasing the occlusion device from the delivery system includes releasing a proximal connection element of the occlusion device from a correspondingly configured distal connection element of the delivery system.

Inventive Concept 91. The method according to Inventive Concept 90, wherein the delivery system includes an implant catheter connected to an operating handle, the implant catheter including a longitudinal passageway for the guidewire, and an inflation tube channel releasably connectable to the corresponding inflation port of the occlusion device, and wherein inflating the compliant balloon includes filling, via the inflation tube and the inflation port of the balloon, the fluid into the fluid-tight balloon chamber.

There is additionally provided, in accordance with an Inventive Concept 92 of the present invention, a method of occluding a cardiovascular defect or a gap between a medical device and adjacent body tissue of a patient, the method including:

advancing a guidewire into a body of the patient using a delivery system;

using the delivery system, positioning a compliant balloon of an occlusion device in a compressed form thereof in the cardiovascular defect or the gap to be occluded, by advancing the occlusion device over the guidewire;

inflating the compliant balloon by filling, via an inflation port of the balloon, a fluid into a fluid-tight balloon chamber defined by the balloon, such that an elongate element, which has a fixed length and is fixed to a distal tip element and a proximal base element, sets a fixed distance between the distal tip element and the proximal base element, the distal tip element disposed at a distal side of the balloon, and the proximal base element disposed at a proximal side of the balloon; and releasing the occlusion device from the delivery system.

Inventive Concept 93. The method according to Inventive Concept 92, wherein the balloon has a balloon lumen forming a longitudinal passage from the proximal side to the distal side of the balloon.

Inventive Concept 94. The method according to Inventive Concept 93, wherein the elongate element is disposed in the balloon lumen.

Inventive Concept 95, The method according to Inventive Concept 93, wherein the distal tip element and the proximal base element are shaped so as to define respective guidewire openings substantially coaxial to the balloon lumen for slidingly receiving therein the guidewire, and wherein advancing the occlusion device over the guidewire includes sliding the guidewire through the guidewire openings.

Inventive Concept 96. The method according to Inventive Concept 92, wherein the elongate element is selected from the group consisting of a tube, a wire, a shaft, a cable, a strand, and a fiber.

Inventive Concept 97. The method according to Inventive Concept 92, wherein the proximal base element and the distal tip element include a proximal disk and a distal disk, respectively.

Inventive Concept 98. The method according to Inventive Concept 92, wherein the compliant balloon includes a compliant material selected from the group consisting of polycaprolactone (PCL), polyglycolic acid (PGA), polylactic acid (PLA), polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

Inventive Concept 99. The method according to Inventive Concept 92, wherein the occlusion device further includes at least one connecting strut fixed to the distal tip element and to the proximal base element.

Inventive Concept 100. The method according to Inventive Concept 99, wherein the at least one connecting strut includes a single connecting strut disposed inside or outside the balloon.

Inventive Concept 101. The method according to Inventive Concept 99, wherein the at least one connecting strut includes a plurality of connecting struts disposed inside or outside the balloon.

Inventive Concept 102. The method according to Inventive Concept 101, wherein the plurality of connecting struts are disposed in a cage-like arrangement.

Inventive Concept 103. The method according to Inventive Concept 101, wherein the plurality of connecting struts are arranged as a frame.

Inventive Concept 104. The method according to Inventive Concept 92, wherein the inflation port includes a self-closing valve.

Inventive Concept 105. The method according to Inventive Concept 104, wherein the inflation port is releasably connected to the delivery system, and wherein the self-closing valve is configured to close upon disconnection of the inflation port from the delivery system.

Inventive Concept 106. The method according to Inventive Concept 92, wherein releasing the occlusion device from the delivery system includes releasing a proximal connection element of the occlusion device from a correspondingly configured distal connection element of the delivery system.

Inventive Concept 107. The method according to Inventive Concept 106, wherein the delivery system includes an implant catheter connected to an operating handle, the implant catheter including a longitudinal passageway for the guidewire, and an inflation tube channel releasably connectable to the corresponding inflation port of the occlusion device, and wherein inflating the compliant balloon includes filling, via the inflation tube and the inflation port of the balloon, the fluid into the fluid-tight balloon chamber.

The above mentioned and other features and objects of this invention and the manner of achieving them will become more apparent and this invention itself will be better understood by reference to the following description of various embodiments of this invention taken in conjunction with the accompanying drawings, in which:

The present invention will be more fully understood from the following detailed description of embodiments thereof, taken together with the drawings, in which:

BRIEF DESCRIPTION OF THE DRAWINGS

FIG. 1a shows a cross-sectional view of an expanded occlusion device according to an application of the present invention;

FIGS. 1b and 1c show side elevational views of the occlusion device illustrated in FIG. 1a, in accordance with an application of the present invention;

FIG. 6a shows a cross-sectional view of an expanded occlusion device according to an application of the invention, in accordance with an application of the present invention;

FIG. 6b shows a side elevational view of the occlusion device illustrated in FIG. 6a, in accordance with an application of the present invention;

FIG. 6c shows a cross-sectional view of an expanded occlusion device according to an application of the invention, in accordance with an application of the present invention;

FIG. 6d shows a side elevational view of the occlusion device illustrated in FIG. 6c, in accordance with an application of the present invention;

FIG. 6e shows a cross-sectional view of an expanded occlusion device according to an application of the invention, in accordance with an application of the present invention;

FIG. 6f shows a side devotional view of the occlusion device illustrated in FIG. 6e, in accordance with an application of the present invention;

FIG. 9a shows a cross-sectional view of an expanded occlusion device according to an application of the invention, in accordance with an application of the present invention;

FIG. 9b shows a side elevational view of the occlusion device illustrated in FIG. 9a, in accordance with an application of the present invention;

FIGS. 11a and 11b show side views of the occlusion device illustrated in FIG. 2a at different respective stages of expansion within a congenital defect, in accordance with an application of the present invention;

FIGS. 13a and 13b show side views of the occlusion device illustrated in FIG. 2a when expanded within a gap between a medical device and the adjacent body tissue, in accordance with an application of the present invention.

FIG. 16 shows a method of deploying the occlusion device illustrated in FIG. 2a, in accordance with an application of the present invention;

Figure 2A:
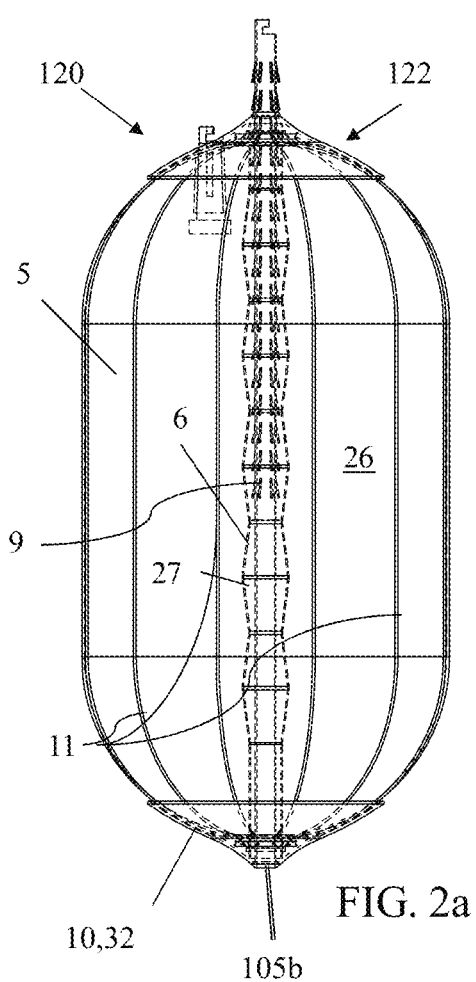
FIG. 2a shows a cross-sectional view of an expanded occlusion device according to an application of the invention.

It will be understood that the figures are not necessarily drawn to scale. In some instances, relative dimensions may be substantially distorted for ease of visualization.

DETAILED DESCRIPTION OF APPLICATIONS

FIG. 1a shows a cross-sectional view of an expanded occlusion device 20 according to an application of the present invention. FIGS. 1b and 1c show side elevational views of the occlusion device 20 illustrated in FIG. 1a, in accordance with an application of the present invention. Occlusion device is for use with a guidewire 106 and a delivery system 107 (shown in FIGS. 10a-c). As shown, the occlusion device 20 comprises a compliant balloon 5 having a central balloon lumen 6 forming a longitudinal passage 27 through an interior of the balloon 5 from a proximal side 28A to a distal side 28B of the balloon 5. The balloon 5 defines a fluid-tight balloon chamber 26. The balloon 5 is typically compliant, as defined above. Optionally, the balloon lumen 6 is foldable, such that the balloon lumen 6 closes on itself after the guidewire 106 (shown in FIGS. 10a-c) is removed, so not to leave an open passage within the occlusion device 20. For example, the foldability of the balloon lumen 6 may be provided by providing proximal and distal valves on the entrances of the balloon lumen 6, or by configuring the balloon lumen 6 to collapse and fold longitudinally.

The occlusion device 20 further comprises a frame 22 comprising a proximal base element 4 and a distal tip element 10, disposed at the proximal and distal sides 28A and 28B of the balloon 5, respectively, and connected by an elongate actuating element 9 passing and longitudinally slidable within the central lumen 6 of the balloon 5. The elongate actuating element 9 is longitudinally moveable with respect to the proximal base element 4 so as to set a distance between the distal tip element 10 and the proximal base element 4. Typically, the elongate actuating element 9 is selected from the group consisting of: a tube, a wire, a shaft, a cable, a strand, and a fiber. Reduction of the distance may cause the distal tip element 10 to move toward the proximal base element 4, the proximal base element 4 to move toward the distal tip element 10, or both movements.

For some applications, the proximal base element 4 and the distal tip element 10 comprise a proximal disk 30 and a distal disk 32, respectively. The frame 22 provides structural support to the balloon 5. The frame 22 may be formed from a cut structure so that each component of the frame 22 is integrally connected with each other. The elongate actuating element 9 may have a linear or nonlinear section and may have plastic or metallic deformable characteristics.

The occlusion device 20 further comprises a locking mechanism 2 for maintaining, between the distal tip element 10 and the proximal base element 4, the distance set using the elongate actuating element 9. For example, the locking mechanism 2 may comprise a crimping element, a threaded element, a locking element, an inflatable balloon, a locking wire, or a ratchet element. For some applications, the locking mechanism 2 is disposed at the proximal side 28A of the balloon 5, for example, connected to or integrated into the proximal base element 4.

The occlusion device 20 is shaped so as to form a closed three-dimensional shape. The occlusion device 20 comprises a proximal connection element 1 that is configured to attach the occlusion device 20 to and release the occlusion device 20 from delivery system 107, e.g., from an implant catheter 14 of delivery system 107. It is noted that the longitudinal passage 27 is still defined through the interior of the balloon 5 after release of the occlusion device 20 from the implant catheter 14. Typically, when the occlusion device 20 is connected to the implant catheter 14, no portion of the implant catheter 14 is disposed within the interior of the balloon 5.

Typically, the proximal base element 4 and the distal tip element 10 (e.g., the proximal and distal disks 30 and 32) are shaped so as to define respective guidewire openings 105a and 105b substantially coaxial to the balloon lumen 6 for slidingly receiving therein guidewire 106 (shown in FIGS. 10a-c) for delivering the occlusion device 20.

For some applications, the proximal base element 4 and the distal tip element 10 (e.g., the proximal and distal disks 30 and 32) are deformable, such as to allow the elements to automatically adjust their shapes upon inflation of the balloon 5. Alternatively, the proximal base element 4 and the distal tip element 10 (e.g., the proximal and distal disks 30 and 32) are not deformable.

For some applications, the proximal base element 4 and the distal tip element 10 (e.g., the proximal and distal disks 30 and 32) comprise a plastic or a metal, e.g., Nitinol.

Although the proximal and distal disks 30 and 32 are shown as circular in the figures, the disks may have other shapes, such as the shape of a flower, a cross, a star, an ellipse, or any other shape as necessary or appropriate for proper cardiovascular defects occlusion and device stabilization. The proximal and distal disks 30 and 32 are typically radially symmetric, but may also be asymmetric.

The occlusion device 20 further comprises an inflation port 3 entering into the balloon 5 along a central axis of the balloon 5 or elsewhere, such as in close vicinity of the central axis. The inflation port 3 is releasably connected to an inflation tube channel of the implant catheter 14 and allows inflation and deflation of the balloon 5 while connected before release of the occlusion device 20 from the implant catheter 14. Within the central lumen 6 of the balloon 5, the balloon 5 may define a guidewire lumen 7 allowing guidewire 106 (shown in FIGS. 10a-c) to freely move axially through the occlusion device 20. Typically, in configurations in which the proximal opening of the guidewire lumen 7 is centered around the central axis of the balloon 5, the inflation port 3 is off-center, and vice versa.

According to an application of the present invention, the compliant balloon 5 may be inflated by filling the balloon chamber 26 with any fluid, including but not limited to saline solution (optionally comprising a contrast medium), blood (e.g., autologous blood), foam, and a glue (e.g., a gel, a liquid polymer that can change its proprieties to become rigid, or a hydrogel that remains a gel or self-cures at body temperature). For applications in which the fluid includes autologous blood, the autologous blood may be drawn from the patient during the deployment of the occlusion device 20, e.g., at a location proximal to the balloon 5 within the patient's body, or drawn from the patient outside the patient's body and filled into the balloon chamber 26 via the deployment system. For applications in which the fluid includes blood, an anti-coagulation agent may be mixed with the blood in order to delay coagulation for a while in case the balloon 5 must be retrieved; eventually the blood coagulates.

The above-mentioned fluid provides the long-term shape setting, sealing and occluding properties of the expanded occlusion device 20. The balloon 5 provides the acute, i.e., immediate shape setting, sealing, and occluding properties of the expanded occlusion device 20. Therefore, for applications in which occlusion device 20 is radiopaque and is implanted in a beating heart under echocardiographic, fluoroscopic, and/or x-ray guidance, upon inflation of the balloon 5, the surgeon can immediately observe whether the defect has been occluded (by observing cessation of blood flow through the defect). The immediate closure of the defect upon inflation of the balloon 5 contrasts with known closure devices comprising a braided wire mesh, which generally do not provide immediate closure of the defect, but instead only provide good closure upon sufficient blood clotting in the mesh after several days or weeks. Thus the effectiveness of these known closure devices can generally only be evaluated at least several days after implantation.

The implant catheter 14 and the inflation port 3 may contain specific channels, valves and membranes designed to be compatible with the fluid used, including filter membranes that can be permeable to blood in the case blood is used as filling fluid of the balloon chamber 26.

Moreover, the frame 22 allows longitudinal adjustment of the balloon 5 to enhance the stability of the occlusion device 20 and to enhance occlusion of the defect.

In some applications, the frame 22 may be designed to have a limited conformability (for example, because of the thickness of the frame 22 or a material property of the frame 22), such as in order to create a tapered shape to provide asymmetrical confinement to the balloon 5, for example, tapered at the distal end, such that the balloon 5 has a pear shape when constrained by anatomy or otherwise constrained. The frame 22 may have a generally conical, or frustoconical shape, cylindrical shape, or any other shape as necessary or appropriate. In some application, the balloon 5 is configured to have limited conformability in some sections of the balloon, such as in order to create a figure-eight shape or a tapered shape, or an asymmetrical shape when expanded under inflation.

In some applications, frame 22 further comprises a single strut 21 passing inside and tapering the balloon 5 component. The strut 21 may or may not be fixed to the inner surface of the balloon 5 or embedded in the balloon 5, as described hereinbelow with reference to FIG. 2a. Optionally, the strut 21 passes through the central lumen 6 of the balloon 5 (configuration not shown).

FIGS. 2a to 9b illustrate further optional features that may be provided in conjunction with the occlusion device 20 as presented in the application of FIGS. 1a to 1c. In order to avoid repetitions, only those features differing from the occlusion device described above will be addressed. Like reference numbers denominate the same or corresponding features.

Figure 2B:
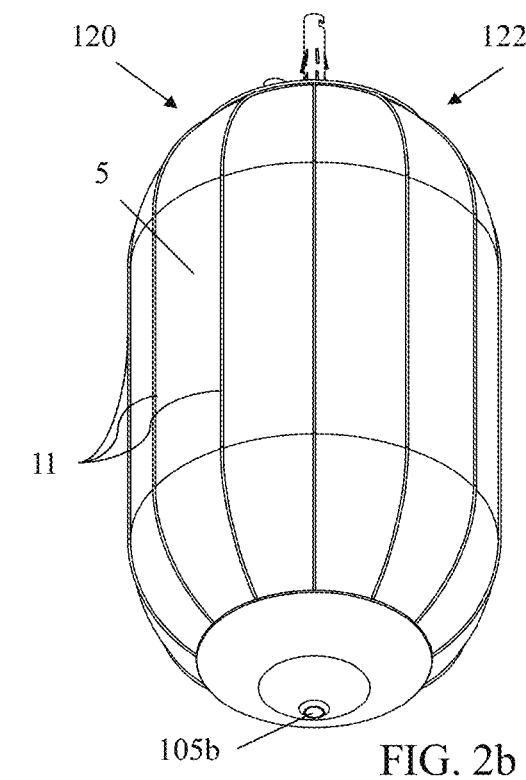
FIGS. 2b and 2c show side elevational views of the occlusion device illustrated in FIG. 2a, in accordance with an application of the present invention.
Figure 2C:
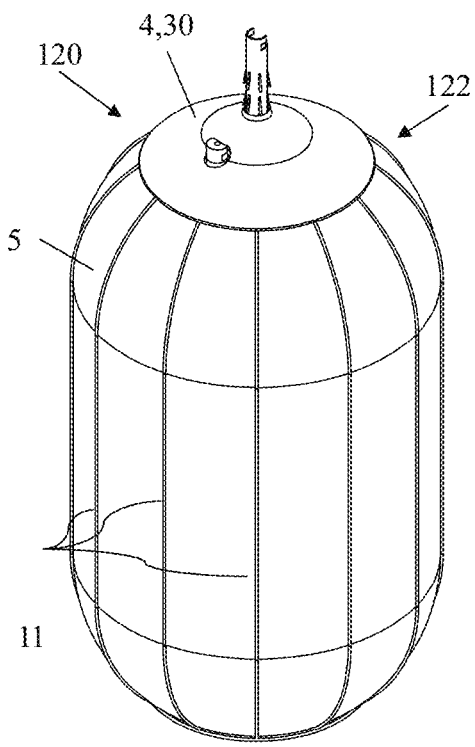

FIG. 2a shows a cross-sectional view of an expanded occlusion device 120, in accordance with an application of the present invention. FIGS. 2b and 2c show side elevational views of the occlusion device 120 illustrated in FIG. 2a, in accordance with an application of the present invention. Occlusion device 120 comprises a frame 122, which may comprise the proximal base element 4 and the distal tip element 10 (e.g., the proximal and distal disks 30 and 32), connected by a plurality of struts 11, which may have any suitable form, passing inside (not shown) or outside (as shown) and tapering the balloon 5 component. Such an application may allow a cage-like structural confinement of the balloon 5 within its assembly, to avoid unnecessary interference of the occlusion device 20 with the body tissue or with implanted prostheses and to provide anchoring support of the occlusion device 20 within the defect, e.g., the cardiovascular defect. In this application, the frame 122 may comprise 2, 4, 6, 8, 10, 12 or any other suitable even or odd number of struts 11. The struts 11 may be disposed inside or outside the balloon 5. For some applications, the struts 11 are not fixed to any surfaces of the balloon 5. For other applications, the struts 11 are (a) fixed to a surface (inner or outer) of the balloon 5, (b) embedded in the wall of the balloon 5 during manufacture (such as by being cast within the wall). Alternatively, the balloon 5 may be molded over the struts 11, which remain internally fixed to the balloon 5.

In some applications, the struts 11 forming the frame 122 may differ in wall thickness and/or width along their entire length or a section thereof. As such, a strut 11 may have a first section that is wider than a second section. In other applications, a middle or a distal end section of a strut 11 may be provided with a larger or smaller wall thickness and/or strut width. Varying the wall thickness and/or the strut 11 width may determine the frame 122 radial stability.

Figure 3A:
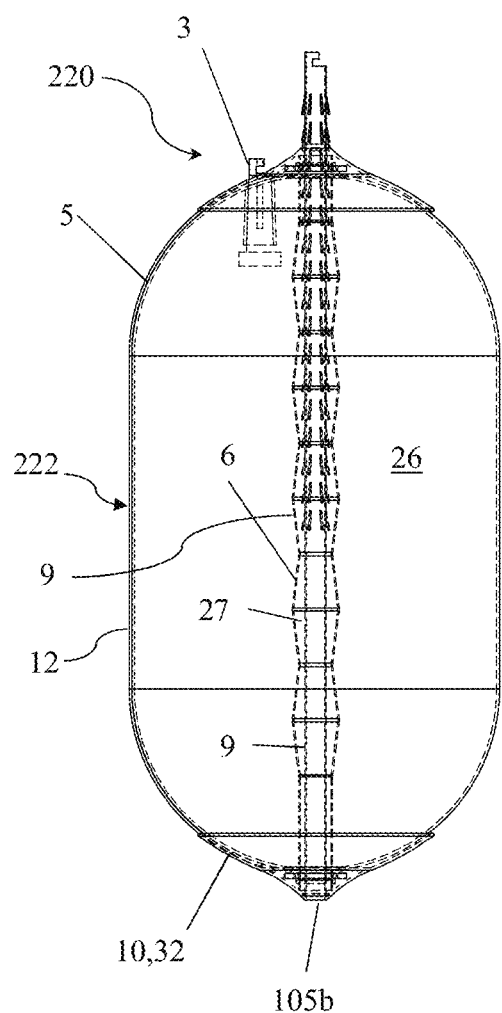
FIG. 3a shows a cross-sectional view of an expanded occlusion device according to an application of the invention.
Figure 3B:
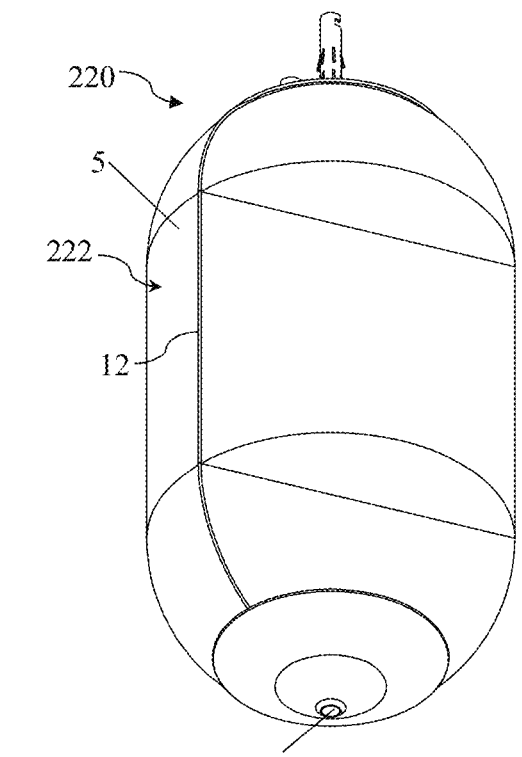
FIGS. 3b and 3c show side elevational views of the occlusion device illustrated in FIG. 3a, in accordance with an application of the present invention.
Figure 3C:
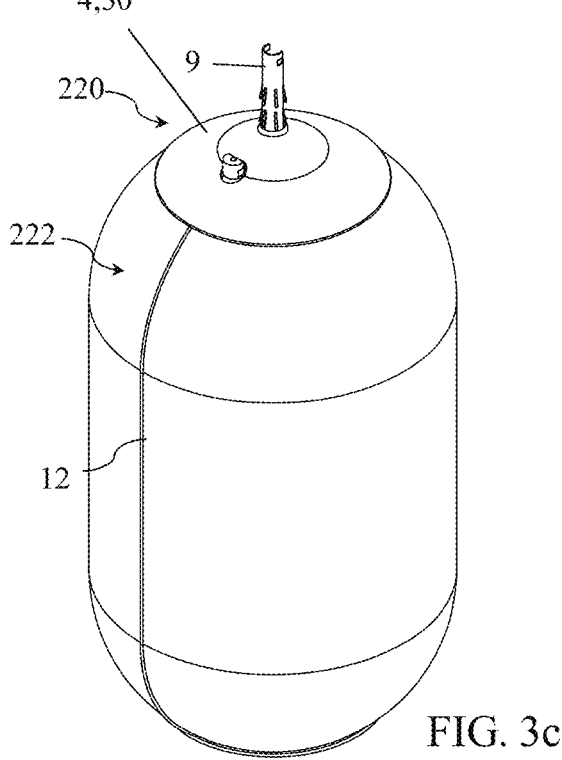

FIG. 3a shows a cross-sectional view of an expanded occlusion device 220, in accordance with an application of the present invention. FIGS. 3b and 3c show side elevational views of the occlusion device 220 illustrated in FIG. 3a, in accordance with an application of the present invention. Occlusion device 220 comprises a frame 222 may comprise the proximal base element 4 and the distal tip element 10 (e.g., the proximal and distal disks 30 and 32), connected by one strut 12 passing outside and tapering the balloon 5 component. The strut 12 may or may not be fixed to the inner surface (not shown) or the outer surface (as shown) of the balloon 5 or embedded in the balloon 5, as described hereinabove with reference to FIG. 2a.

Figure 4A:
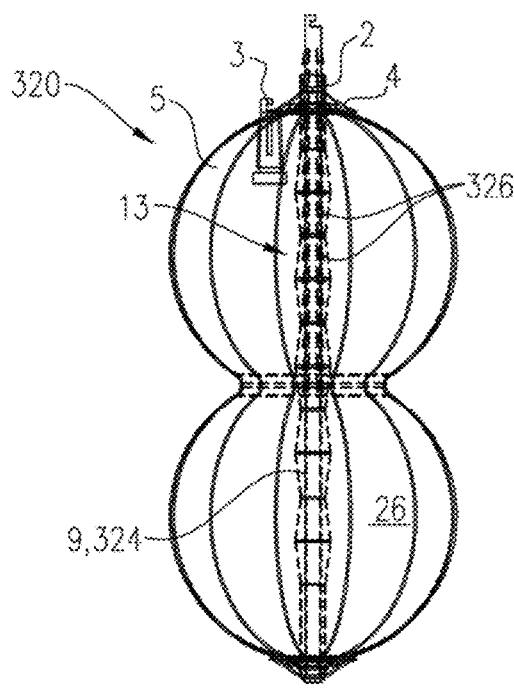
FIG. 4a shows a cross-sectional view of an expanded occlusion device according to an application of the invention, in accordance with an application of the present invention.
Figure 4B:
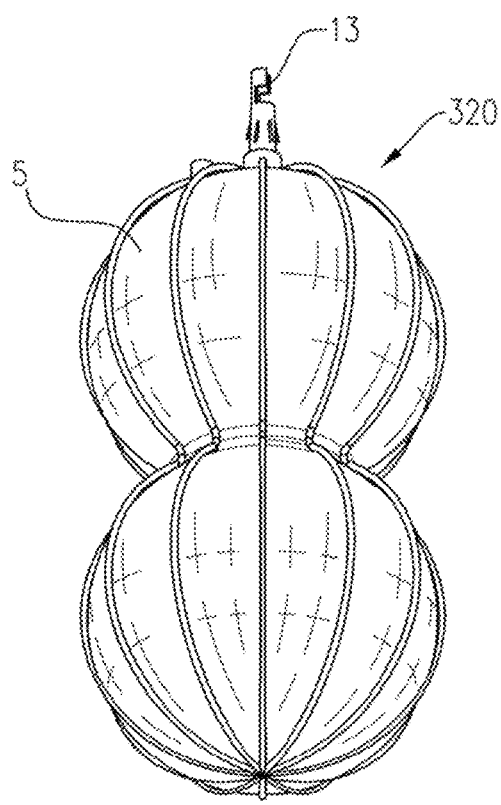
FIGS. 4b and 4c show side elevational views of the occlusion device illustrated in FIG. 4a, in accordance with an application of the present invention.
Figure 4C:
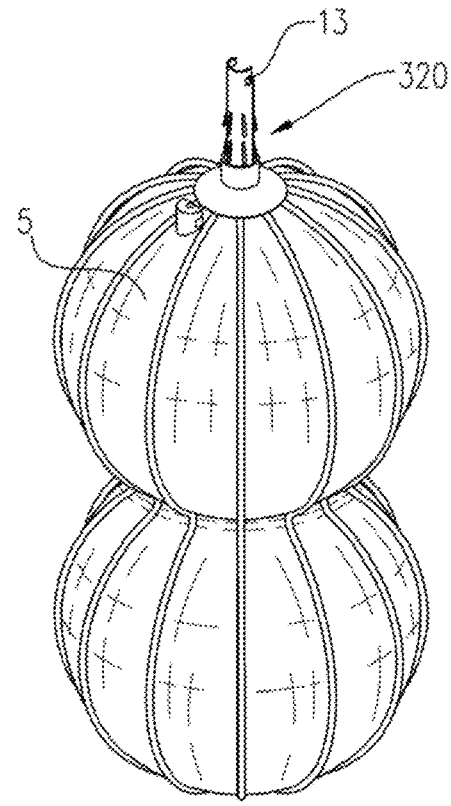

Reference is now made to FIG. 4a, which shows a cross-sectional view of an expanded occlusion device 320 according to an application of the present invention. Reference is also made to FIGS. 4b and 4c, which show side elevational views of the occlusion device 320 illustrated in FIG. 4a, in accordance with an application of the present invention.

Figure 5A:
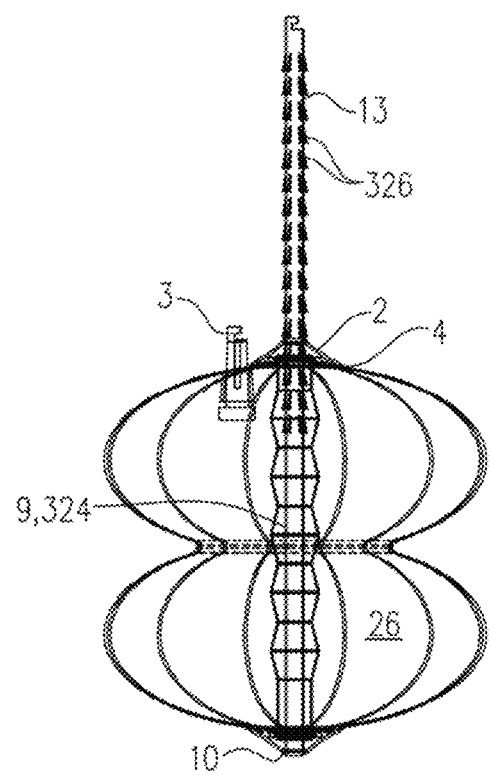
FIG. 5a shows a cross-sectional view of the occlusion device illustrated in FIG. 4a after the ratchet component actuation and longitudinal shortening, in accordance with an application of the present invention.
Figure 5B:
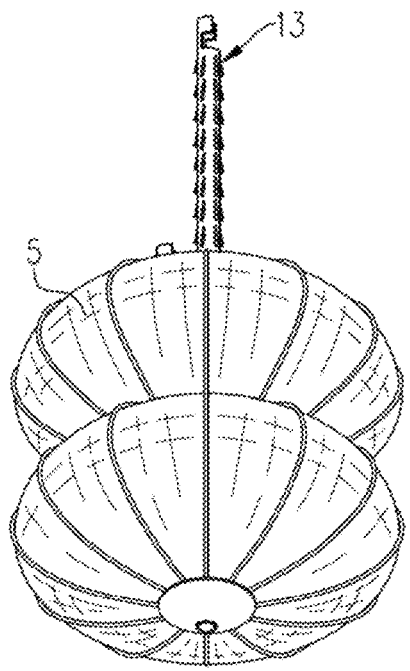
FIGS. 5b and 5c show side elevational views of the occlusion device illustrated in FIG. 5a, in accordance with an application of the present invention.
Figure 5C:
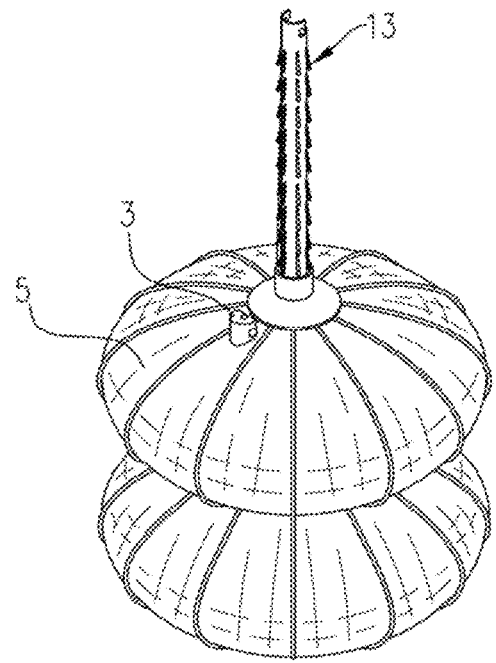

Reference is also made to FIG. 5a, which is a cross-sectional view of the occlusion device 320 illustrated in FIGS. 4a-c after actuation of the ratchet mechanism 13 described below and longitudinal shortening, in accordance with an application of the present invention. Reference is also made to FIGS. 5b and 5c, which show side elevational views of the occlusion device 320 illustrated in FIG. 5a, in accordance with an application of the present invention.

As shown in FIGS. 4a-c, in this configuration the elongate actuating element 9 comprises an elongate actuating element 324 that is fixedly connected to the distal tip element 10. The elongate actuating element 324 comprises a plurality of teeth 326, and the locking mechanism 2 comprises one or more pawls. The elongate actuating element 324 and the pawls of the locking mechanism together provide a ratchet mechanism 13, such that the distance between the distal tip element 10 and the proximal base element 4 is selectable from a range of distances by distally pulling the elongate actuating element 324 through the locking mechanism 2. This ratchet mechanism 13 allows longitudinal adjustment of the occlusion device 320 in one direction, while inhibiting movement in the other direction, so that the proximal base element 4 and the distal tip element 10 can only come closer to each other, before device 320 is released from the implant catheter 14, as shown in FIGS. 5a-c. Optionally, any excess proximal portion of the elongate actuating element 324 that extends through the proximal base element 4 to outside the occlusion device 320 is cut and removed from the body; to this end, the elongate actuating element 324 may be perforated or have weaker (e.g., thinner) axial portions that are configured to break upon application of a breaking force.

Also as shown in FIGS. 4a-c and 5a-c, occlusion device 320 optionally is configured to assume a figure-eight shape upon inflation. For example, the figure-eight shape may be achieved by the thickness of an axial central portion of the struts 11, or by a limiting band that connect the struts 11 at that axial position of the narrower central portion of the figure eight, or by the thickness of the balloon 5 that results in less inflation in the narrower central portion of the figure eight.

Reference is now made to FIG. 6a, which shows a cross-sectional view of an expanded occlusion device 370 according to an application of the present invention. Reference is also made to FIG. 6b, which shows a side elevational view of the occlusion device 370 illustrated in FIG. 6*a*, in accordance with an application of the present invention. Except as described below, occlusion device 370 is identical to occlusion device 320, described hereinabove with reference to FIGS. 4*a-c* and 5*a-c*.

As shown in FIGS. 6*a-b*, in this configuration the elongate actuating element 9 comprises an elongate actuating element 374 that is fixedly connected to the distal tip element 10. The elongate actuating element 374 is shaped so as to define a thread 376, and the locking mechanism 2 comprises a threaded opening defined by the proximal base element 4. The thread 376 of the elongate actuating element 374 is disposed within the threaded opening. The occlusion device 370 is configured such that rotation of the elongate actuating element 374 with respect to the proximal base element 4 causes the elongate actuating element 374 to longitudinally move with respect to the proximal base element 4, thereby setting the distance between the distal tip element 10 and the proximal base element 4 and maintaining the set distance. This arrangement allows both shortening of the distance and subsequent lengthening if necessary. For some applications, the locking mechanism 2 is disposed at the proximal side 28A of the balloon 5, for example, connected to or integrated into the proximal base element 4. Optionally, any excess proximal portion of the elongate actuating element 374 that extends through the proximal base element 4 to outside the occlusion device 370 is cut and removed from the body.

Reference is still made to FIGS. 6*a-b*. Alternatively, the elongate actuating element 374 is not shaped so as to define the thread 376, and the locking mechanism 2 comprises a non-threaded opening defined by the proximal base element 4. Proximally pulling the elongate actuating element 374 sets the distance between the distal tip element 10 and the proximal base element 4. Once the desired distance has been set, the locking mechanism 2 is locked to fix the elongate actuating element 374 with respect to the proximal base element 4. For some applications, the locking mechanism 2 is disposed at the proximal side 28A of the balloon 5, for example, connected to or integrated into the proximal base element 4.

Reference is now made to FIG. 6*c*, which shows a cross-sectional view of an expanded occlusion device 380 according to an application of the present invention. Reference is also made to FIG. 6*d*, which shows a side elevational view of the occlusion device 380 illustrated in FIG. 6*c*, in accordance with an application of the present invention. Except as described below, occlusion device 380 is identical to occlusion device 370, described hereinabove with reference to FIGS. 6*a-b*.

As shown in FIGS. 6*c-d*, in this configuration the elongate actuating element 9 comprises an elongate actuating element 384 that is fixedly connected to the distal tip element 10. The locking mechanism 2 comprises a spool assembly 382, comprising a spool and, typically, a housing enclosing the spool. A proximal portion of the elongate actuating element 384 is wound around the spool. The occlusion device 380 is configured such that rotation of the spool causes the elongate actuating element 384 to longitudinally move with respect to the proximal base element 4, thereby setting the distance between the distal tip element 10 and the proximal base element 4 and maintaining the set distance. This arrangement allows both shortening of the distance and subsequent lengthening if necessary. For some applications, the locking mechanism 2 is disposed at the proximal side 28A of the balloon 5, for example, connected to or integrated into the proximal base element 4.

Reference is now made to FIG. 6*e*, which shows a cross-sectional view of an expanded occlusion device 390 according to an application of the present invention. Reference is also made to FIG. 6*f*, which shows a side elevational view of the occlusion device 390 illustrated in FIG. 6*e*, in accordance with an application of the present invention. Except as described below, occlusion device 390 is similar to occlusion device 370, described hereinabove with reference to FIGS. 6*a-b*.

As shown in FIGS. 6*e-f*, in this configuration the elongate actuating element 9 comprises an elongate actuating element 392 that is axially fixedly connected to a proximal base element 395. The elongate actuating element 392 is shaped so as to define a thread 396, and the locking mechanism 2, which is disposed at the distal side 28B of the balloon 5, comprises a threaded opening defined by a distal tip element 398. The thread 396 of the elongate actuating element 392 is disposed within the threaded opening. The occlusion device 390 is configured such that rotation of the elongate actuating element 392 with respect to the distal tip element 398 causes the elongate actuating element 392 to longitudinally move with respect to the distal tip element 398, thereby setting the distance between the distal tip element 398 and the proximal base element 395 and maintaining the set distance. This arrangement allows both shortening of the distance and subsequent lengthening if necessary. This configuration is appropriate for implantation locations in which the excess distal portion of the elongate actuating element 392 that protrudes from the distal side 28B of the occlusion device 390 upon shortening of the device does not interfere with the anatomy, such as in the LAA, as described hereinbelow with reference to FIGS. 12*a-b*.

Optionally, the proximal base element and a proximal portion of the elongate actuating element 392 together comprise a rotational ratchet mechanism 394, which is configured to allow rotation of the elongate actuating element 392 in only one rotational direction.

Figure 7:
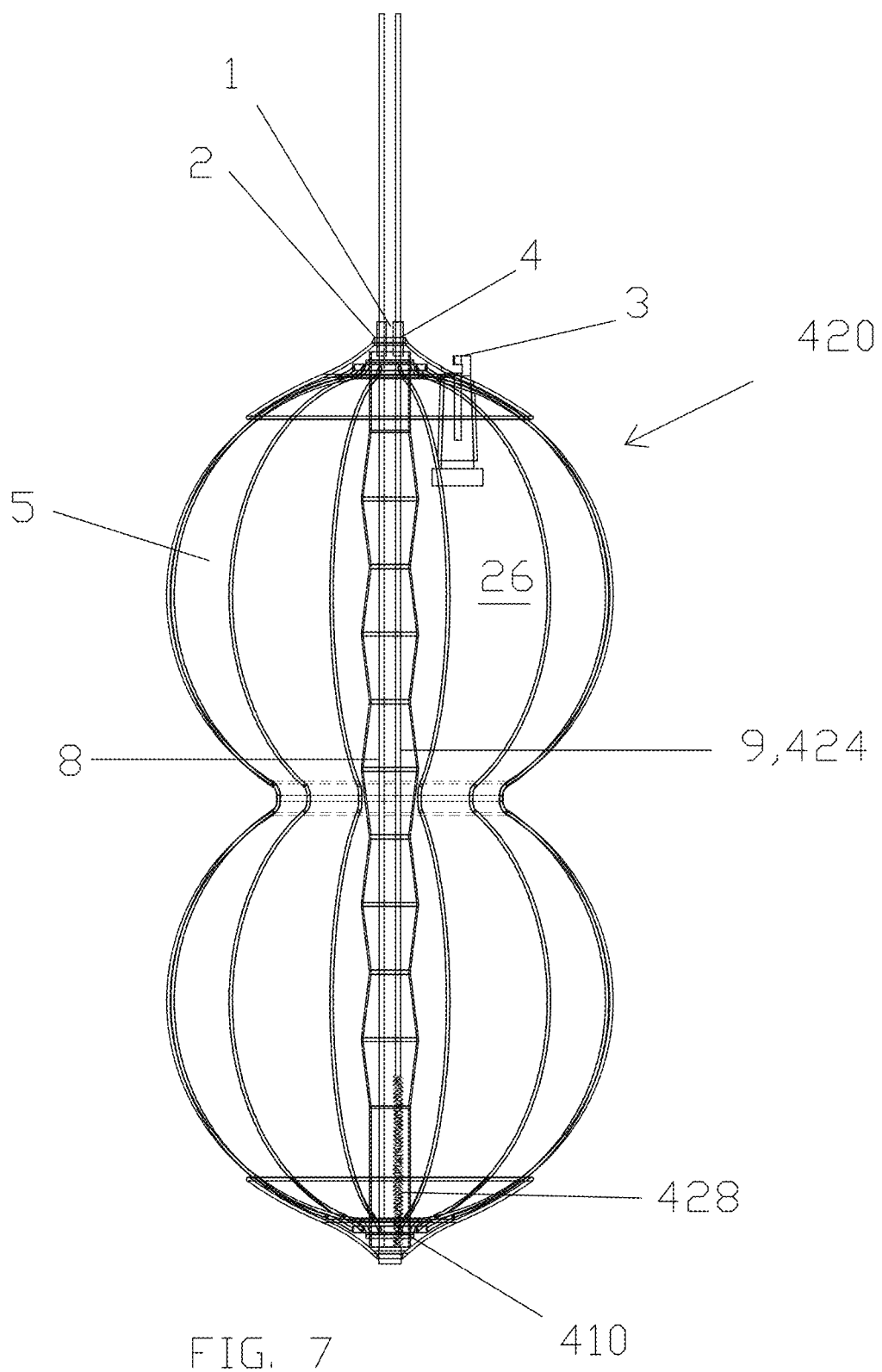
FIG. 7 shows a cross-sectional view of an expanded occlusion device according to an application of the invention, in accordance with an application of the present invention.

Reference is now made to FIG. 7, which shows a cross-sectional view of an expanded occlusion device 420 according to an application of the present invention. Occlusion device 420 comprises a locking elongate element 8 that (a) passes through the locking mechanism 2 within the central lumen 6 and (b) is fixed to a distal tip element 410. The locking elongate element 8 is longitudinally slidable with respect to the proximal base element 4. Typically, the locking elongate element 8 is selected from the group consisting of: a tube, a wire, a shaft, a cable, a strand, and a fiber.

In this configuration, elongate actuating element 9 comprises an elongate actuating element 424 that is disposed within the central lumen 6, is releasably connected to the distal tip element 410, and is longitudinally slidable with respect to the proximal base element 4. Typically, the elongate actuating element 424 is selected from the group consisting of: a tube, a wire, a shaft, a cable, a strand, and a fiber. After longitudinal adjustment of the length of the occlusion device 20 by adjusting the distance between the proximal base element 4 and the distal tip element 410 by pulling and/or pushing the elongate actuating element 424, the locking mechanism 2 is activated, thereby securing the locking elongate element 8 within the locking mechanism 2 in the proximal base element 4 through which the locking wire 24 passes, in order to maintain fixed the distance between the proximal base element 4 and the distal tip element 410 set using the elongate actuating element 424. For some applications, the locking mechanism 2 is disposed at the proximal side 28A of the balloon 5, for example, connected to or integrated into the proximal base element 4.

The elongate actuating element 424 may be pulled and/or pushed directly by the user, in which case the axial movement of the elongate actuating element 424 pulls or pushes the distal tip element 410 in the direction of the proximal base element 4. Pulling or pushing the elongate actuating element 424 also causes corresponding motion of the locking elongate element 8 through the proximal base element 4, typically as a result of sufficient axial stiffness of the locking elongate element 8.

After the desired distance has been set and the locking mechanism 2 has locked the locking elongate element 8, the elongate actuating element 424 is released from the distal tip element 410, and removed from the occlusion device 420 and the patient's body. For example, a distal portion 426 of the elongate actuating element 424 may be shaped so as to define a thread 428, and the distal tip element 410 may be shaped so as to define a threaded opening to which the thread 428 of the distal portion 426 of the elongate actuating element 424 is releasably threadingly connected, such that the elongate actuating element 424 is releasably connected to the distal tip element 410. The elongate actuating element 424 is released from the distal tip element 410 by rotating the elongate actuating element 424, thereby unscrewing it from the distal tip element 410. Alternatively, for example, the elongate actuating element 424 may be releasably connected to the distal tip element 410 using first and second positive connection elements, such as described hereinbelow with reference to FIG. 8.

It is noted that in this configuration, and in other configurations in which the elongate actuating element 9 is releasably connected to the distal tip element 410, the elongate actuating element 9 is not an element of the occlusion device 20, and indeed is disconnected from the occlusion device 20 during the implantation procedure and removed from the body.

Optionally, any excess proximal portion of the locking elongate element 8 that extends through the proximal base element 4 to outside the occlusion device 420 is cut and removed from the body.

Figure 8:
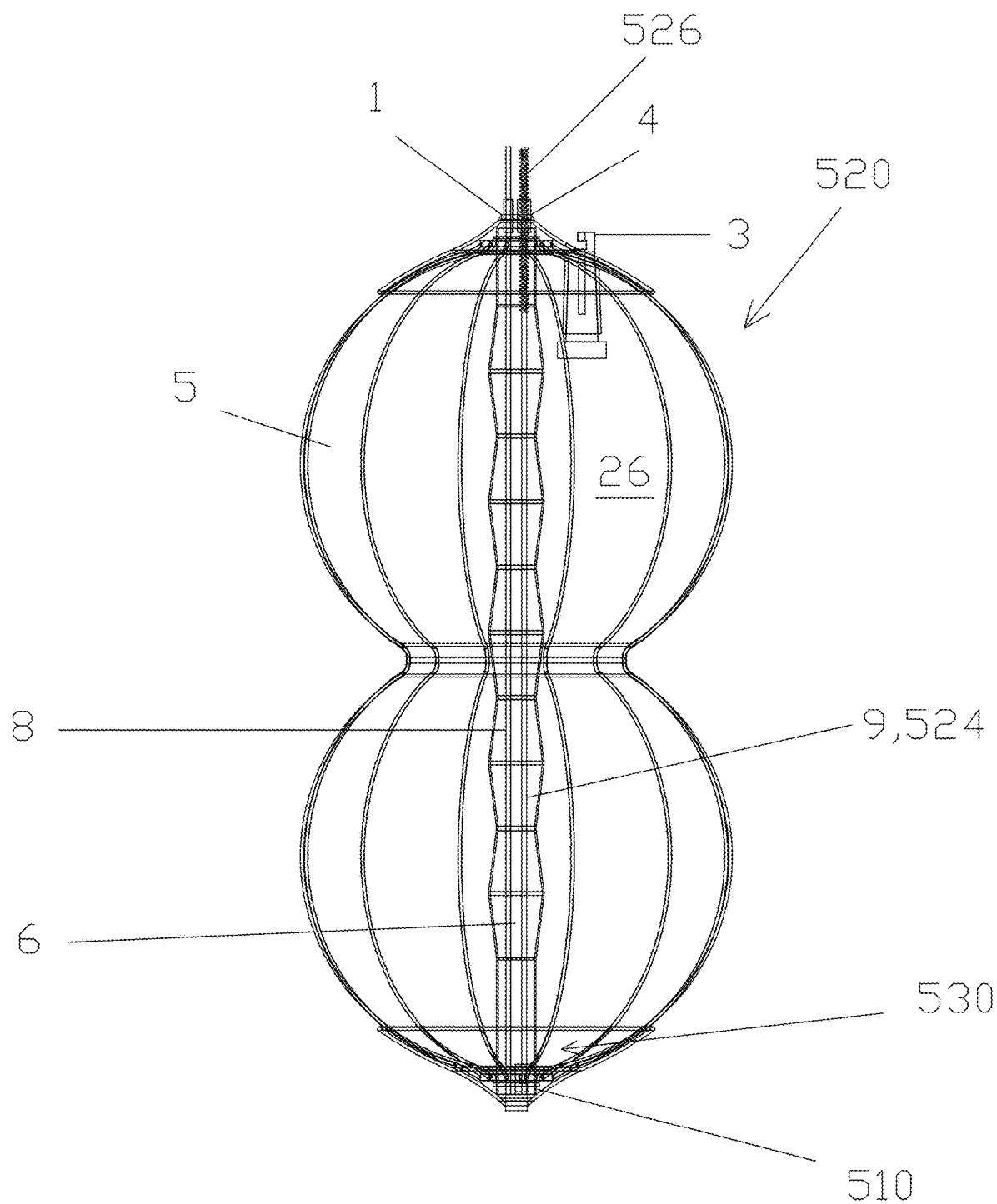
FIG. 8 shows a cross-sectional view of an expanded occlusion device according to an application of the invention, in accordance with an application of the present invention.

Reference is now made to FIG. 8, which shows a cross-sectional view of an expanded occlusion device 520 according to an application of the present invention. Other than as described below, occlusion device 520 is identical to occlusion device 420, described hereinabove with reference to FIG. 7.

In this configuration, elongate actuating element 9 comprises an elongate actuating element 524, which, other than as described below, is similar to elongate actuating element 424, described hereinabove with reference to FIG. 7. The elongate actuating element 524 is shaped so as to define a thread 526. The proximal base element 4 is shaped so as to define a threaded opening, and the thread 526 of the elongate actuating element 524 is disposed within the threaded opening. Typically, the elongate actuating element 524 is selected from the group consisting of: a tube, a wire (e.g., a plurality of wires woven together), a shaft, a cable, a strand, and a fiber.

The elongate actuating element 524 may be rotated by the user, in which case the elongate actuating element 524 engages the threaded opening, such that rotation of the elongate actuating element 524 pulls a distal tip element 510 in the direction of the proximal base element 4 and causes shortening of the occlusion device 20, thereby setting the distance between the distal tip element 510 and the proximal base element 4 and maintaining the set distance.

For some applications, the locking mechanism 2 is disposed at the proximal side 28A of the balloon 5, for example, connected to or integrated into the proximal base element 4.

After the desired distance has been set and the locking mechanism 2 has locked the locking elongate element 8, the elongate actuating element 524 is released from the distal tip element 510, and removed from the occlusion device 520 and the patient's body. For example, a distal portion 530 of the elongate actuating element 524 may comprise a first positive connection element, and the distal tip element 510 may be shaped so as to define a second positive connection element. The first positive connection element is releasably connected to the second positive connection element, such that the elongate actuating element 524 is releasably connected to the distal tip element 510. The elongate actuating element 524 is released from the distal tip element 510 by decoupling the first positive connection element from the second positive connection element, such as by removing a retaining wire from within respective channels of the positive connection elements, as is known in the art.

Reference is now made to FIG. 9a, which shows a cross-sectional view of an expanded occlusion device 540 according to an application of the present invention. Reference is also made to FIG. 9b, which shows a side elevational view of the occlusion device 540 illustrated in FIG. 9a, in accordance with an application of the present invention. Except as described below, occlusion device 380 is identical to occlusion device 370, described hereinabove with reference to FIGS. 6a-b.

As shown in FIGS. 9a-b, in this configuration the elongate actuating element 9 is connected to the distal tip element 10 by being looped through a distal pulley system 544 such that first and second portions 542A and 542B of the elongate actuating element 9 extend distally through the proximal base element. Proximal pulling of one or both of the portions 542A and 542B sets the distance between the distal tip element 10 and the proximal base element 4. The locking mechanism 2 comprises a locking mechanism 546, e.g., which uses compression and/or friction to hold the elongate actuating element 9, such as in a smaller channel of the locking mechanism 546. Optionally, the locking mechanism 546 can be released after locking, in order to readjust the distance between the distal tip element 10 and the proximal base element 4, and then locked again. Locking the locking mechanism 546 maintains the distance set between the distal tip element 10 and the proximal base element 4. This arrangement allows both shortening of the distance and subsequent lengthening if necessary. The locking mechanism 546 is typically disposed at the proximal side 28A of the balloon 5, for example, connected to or integrated into the proximal base element 4.

Figure 10A:
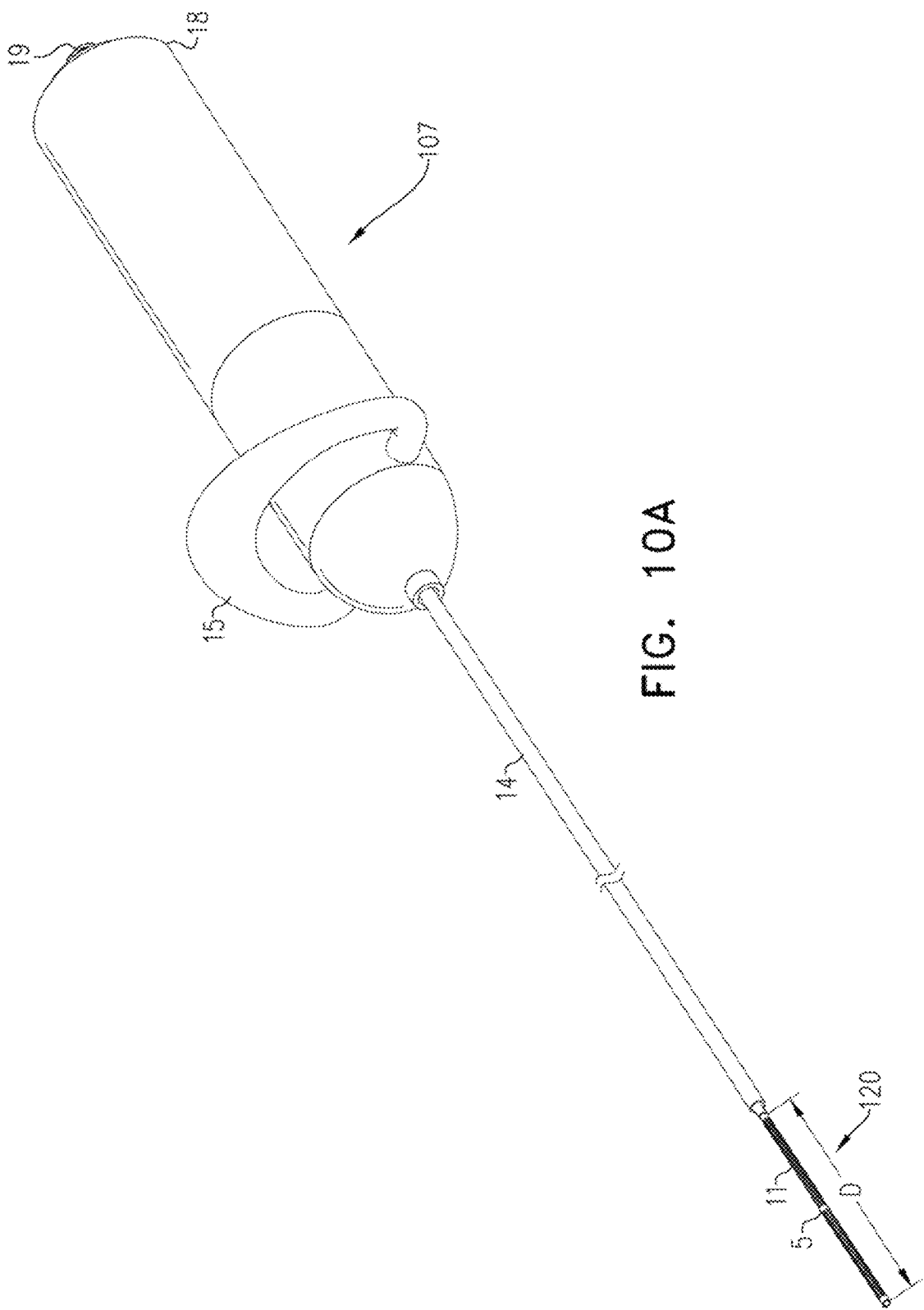
FIG. 10a shows a cross-sectional view of the occlusion device illustrated in FIG. 2a in a compressed form thereof within an implant catheter of a delivery system, in accordance with an application of the present invention.
Figure 10B:
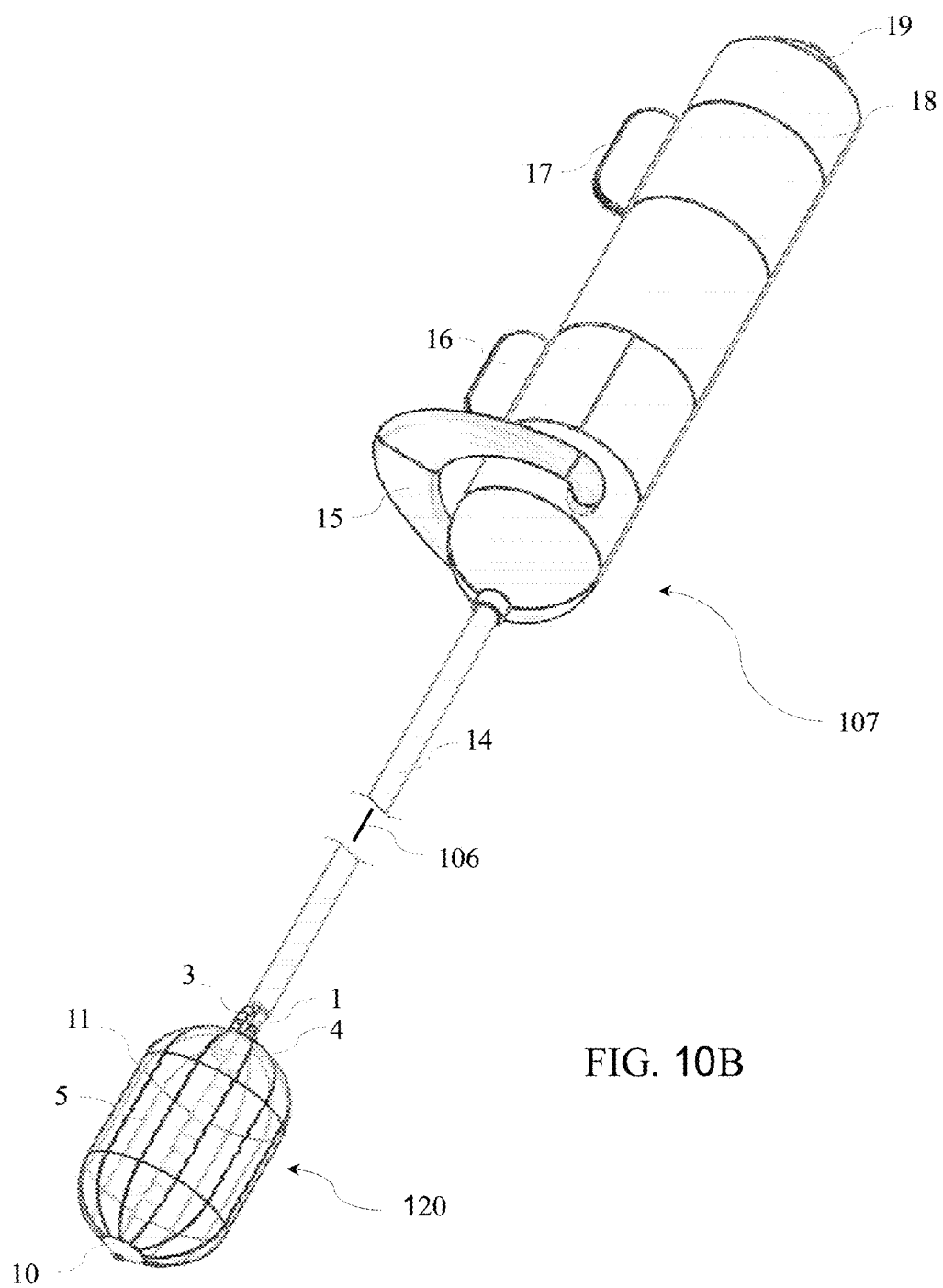
FIGS. 10b and 10c show a side view and a cross-sectional view, respectively, of the occlusion device illustrated in FIG. 2a when released from the implant catheter but still connected to the implant delivery system, in accordance with an application of the present invention.
Figure 10C:
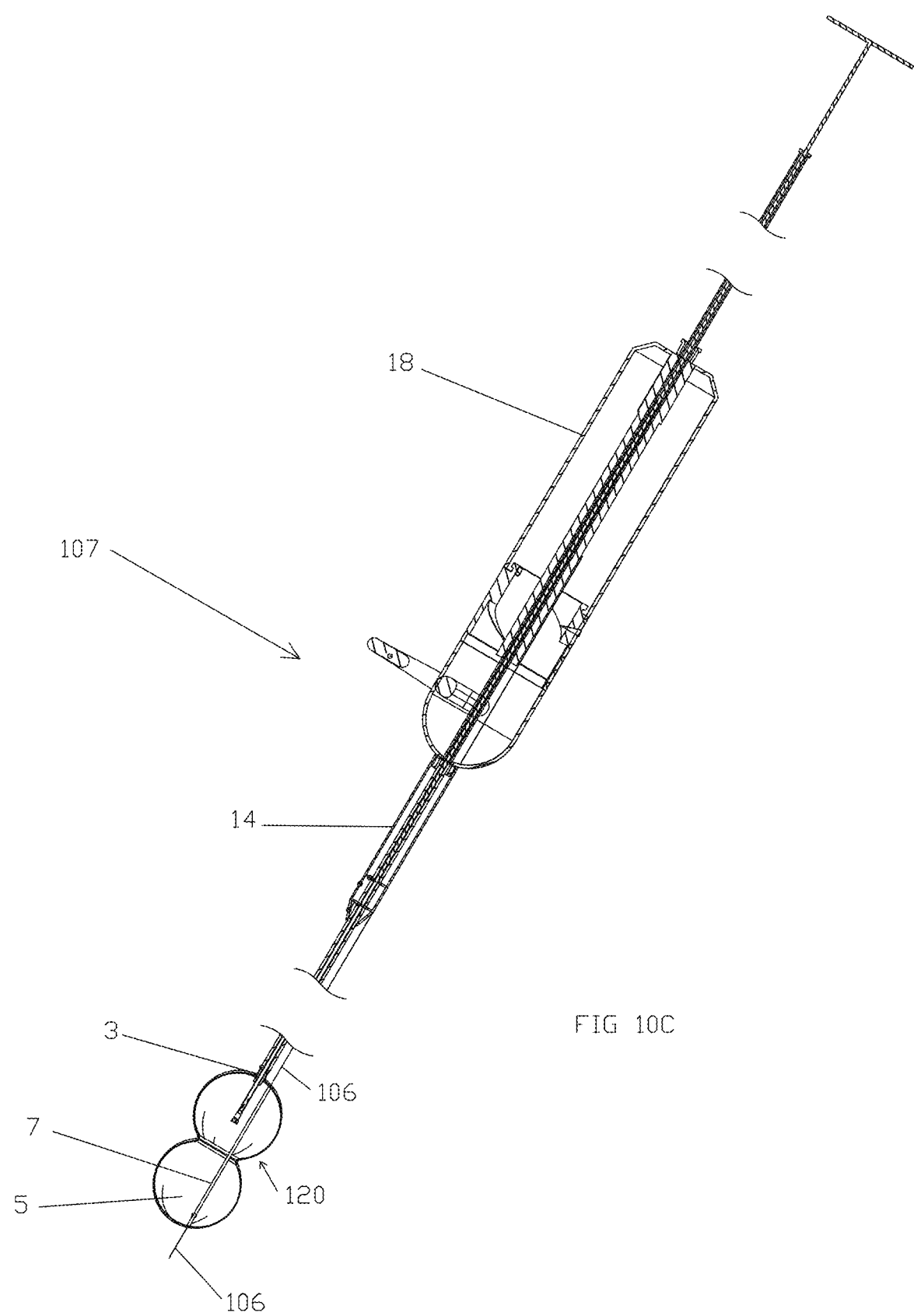

Reference is now made to FIG. 10a, which shows a cross-sectional view of the occlusion device 120 illustrated in FIG. 2a in a compressed form thereof within the implant catheter 14 of the delivery system 107, in accordance with an application of the present invention. Reference is also made to FIGS. 10b and 10c, which show a perspective view and a cross-sectional view, respectively, of the occlusion device 120 illustrated in FIG. 2a, and of its main components, when released from the implant catheter 14 but still connected to the delivery system 107, in accordance with an application of the present invention. FIGS. 10a-c show the occlusion device 120 by way of example; the delivery system 107 may also be used to deliver the other occlusion devices described herein, mutatis mutandis.

The implant catheter 14 allows the introduction of the occlusion device 120 through the cardiovascular system to a defect in the cardiovascular apparatus, to deploy the occlusion device 120 to seal the defect and maintain the occlusion, or the introduction of the occlusion device 120 to another location in the patient's body. Typically, the delivery system 107 further comprises a multiple-knobs delivery system handle 18.

The implant catheter 14 is connected to the occlusion device 120 by a proximal connection element 1. The implant catheter 14 contains the occlusion device 120 in its compressed form, i.e., its deflated and not expanded configuration. For some applications, when the occlusion device 120 is disposed in the implant catheter 14 in the compressed form, a greatest distance D between the proximal base element 4 and the distal tip element 10 is between 8 and 80 mm, such as between 10 and 60 mm. (The "greatest distance" is the distance between respective points of the proximal base element 4 and the distal tip element 10, which points are farthest from each other.) As mentioned above, FIG. 10*a* shows the occlusion device 120 by way of example; the delivery system 107 may also be used to deliver the other occlusion devices described herein, mutatis mutandis, in which case these other occlusion devices may optionally have the greatest distance D described immediately above.

The delivery system 107 comprises all the components and passages to allow controllable occlusion device 120 exposure, inflation, deflation, longitudinal adjustment, retrievability, and release at the end of the implantation. The implant catheter 14 is typically steerable, as is known in the catheter art. In another configuration, the implant catheter 14 is flexible instead of steerable.

Exposure of occlusion device 120 is controlled by an implant knob 16 in the delivery system handle 18. For example, advancement of occlusion device 120 may be achieved by exposing and retrieving a connecting hypotube that is connected to the proximal base element 4. Retrieval may be achieved by pulling a securing wire that is placed within the hypotube, so as to hold the securing wire in position within a positive connection. Proximal withdrawal of the securing wire frees the positive connection, thereby releasing the occlusion device 120. For some applications, the handle 18 comprises a disk actuating knob 17, which is arranged to move the elongate actuating element, to change the distance between the distal tip element 10 and the proximal base element 4, such as by rotating and/or pulling/pushing the elongate actuating element, depending on the specific configuration of the elongate actuating element, as described hereinabove.

The delivery system 107 allows the course of the guidewire 106, used to guide the occlusion device 120 to the targeted defect, and of the elongate actuating element, used to adjust the length of the occlusion device 120, within the structure of the occlusion device and within the central lumen 6 of the occlusion device 120.

Typically, the delivery system 107 includes mechanisms to inflate and deflate of the balloon 5 via an inflation port 19 in the handle 18.

The delivery system 107 is configured to provide steering functionality in order to achieve good positioning of the occlusion device 120 in the targeted defect, for example controlled by a steering knob 15, including a steering limiter, within the delivery system handle 18. For cardiac applications, the steering functionality enables either an antero-grade approach from the venous groin to the inferior vena cava, to the right atrium, to the left atrium, or a retrograde approach from the arterial groin to the left ventricle, and allows the occlusion device 120 implanted using any of the techniques known in the art.

Reference is made to FIGS. 1*c*-9*b*. For some applications, the frame 22, 122, or 222, comprising the proximal base element 4 and the distal tip element 10 (e.g., the proximal and distal disks 30 and 32) and the elongate actuating element 9, struts 11, or strut 12, respectively, has plastic or metallic deformable characteristics, and may comprise any suitable biocompatible material including stainless steel, titanium, nitinol, tantalum, gold, platinum iridium, tungsten, alloys of any of the above-mentioned metals, including platinum-iridium alloys, cobalt-chromium alloys, nickel-titanium alloys and nickel-titanium-platinum alloys. Alternatively, the frame 22, 122, or 222 may comprise a polymer, including a polyester or polycarbonate copolymers, or any metal or polymer or combination of polymer(s) and metal(s) able to provide soft plastic deformation. Suitable materials include biodegradable materials that are also biocompatible, intending a material that undergoes breakdown or decomposition into non-significant compounds as part of a normal biological process. Suitable biodegradable materials include polylactic acid, polyglycolic acid (PGA), collagen or other connective proteins or natural materials, polycaprolactone, hyaluronic acid, adhesive proteins, co-polymers of these materials as well as composites and combinations thereof and combinations of other biodegradable polymers.

Reference is still made to FIGS. 1*c*-9*b*. The frame 22, 122, or 222 and the balloon 5 of the occlusion device 20, 120, or 220, respectively, according to some applications of the invention may be fabricated in different sizes, as necessary or appropriate for use in different sizes of cardiovascular defects or other suitable areas of the body.

Figure 11B:
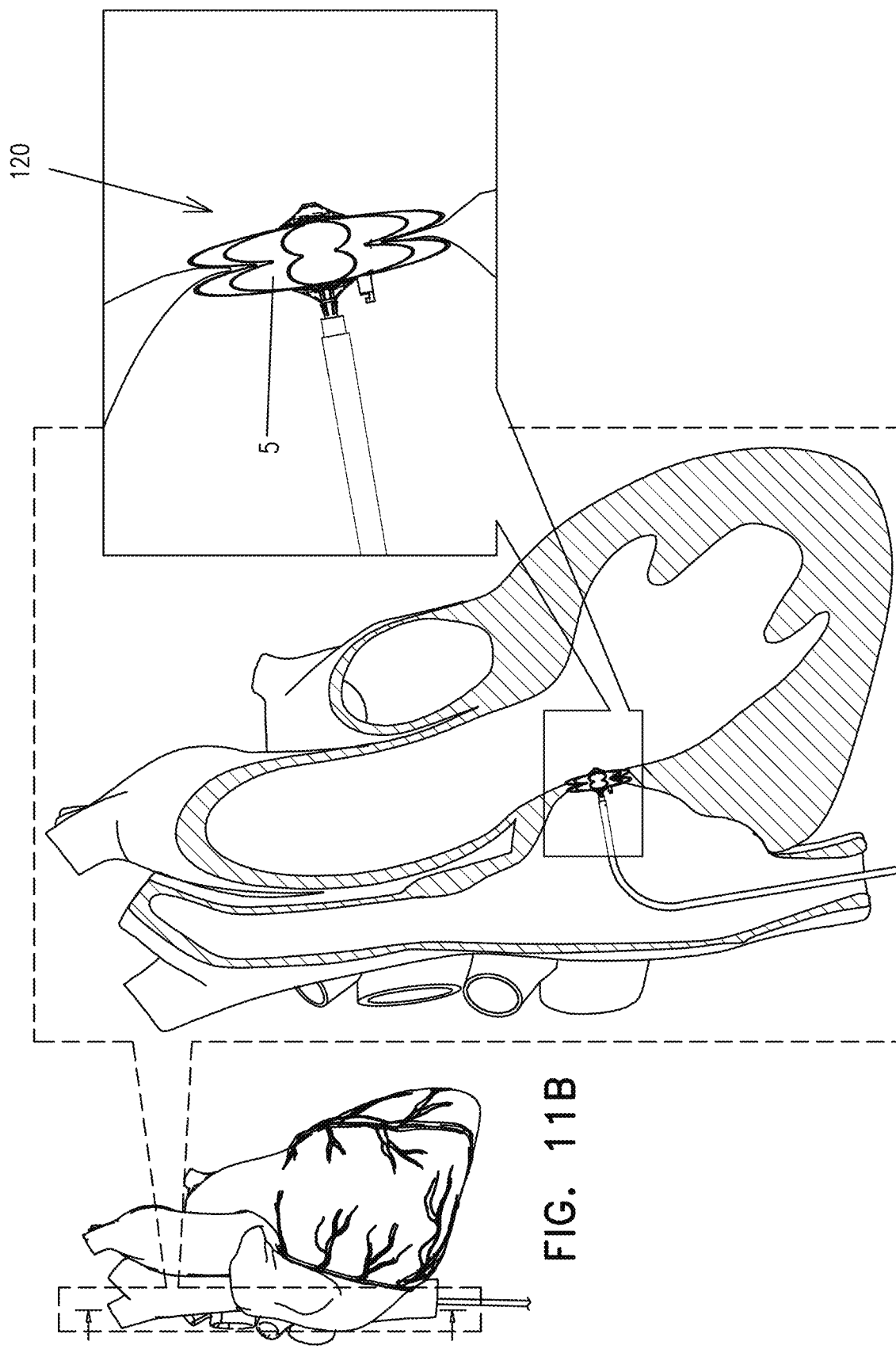

Reference is made to FIGS. 10*a-c* and to FIGS. 11*a-b*, which show side views of the occlusion device 120 illustrated in FIG. 2*a* at different respective stages of expansion within a congenital defect (e.g., patent foramen ovale (PFO)), in accordance with an application of the present invention. FIGS. 11*a-b* show the occlusion device 120 by way of example; these techniques may also be used with the other occlusion devices described herein, mutatis mutandis.

In some applications of the present invention, a method of occluding a cardiovascular defect of a patient is provided. Alternatively, the method may be used to seal a gap between a medical device and adjacent body tissue of a patient; for example, the medical device may be a prosthetic cardiac valve, and the method may treat paravalvular leak between the prosthetic cardiac valve and adjacent cardiac tissue of the patient.

The guidewire 106 is advanced into a body of the patient using delivery system 107, such as shown in FIG. 10*a*. Using the delivery system 107, compliant balloon 5 of the occlusion device 120 is positioned in a longitudinally extended form thereof (either partially or entirely compressed) in the cardiovascular defect, by advancing the occlusion device 120 over the guidewire 106. Optionally, the balloon 5 is partially inflated before it is positioned in the longitudinally extended form thereof in the cardiovascular defect or the gap to be occluded. Alternatively, optionally, after the balloon 5 is positioned in the longitudinally extended form thereof in the cardiovascular defect or the gap to be occluded, the balloon 5 is partially inflated, and, thereafter, is repositioned in the longitudinally extended form thereof in the cardiovascular defect or the gap to be occluded.

The compliant balloon 5 is inflated by filling, via the inflation port 3 of the balloon 5, a fluid into the fluid-tight balloon chamber 26 defined by the balloon 5. FIG. 11*a* shows the occlusion device 20 after the balloon 5 has been inflated. The figure-eight shape shown in FIG. 11*a* may be achieved either because the defect constrains the balloon 5 to have the shape, and/or because the balloon 5 is configured to assume the shape even in the absence of the anatomy.

Thereafter, the balloon 5 is expanded in a radial or a lateral direction by shortening the distance between the distal tip element 10 and the proximal base element 4 to a desired distance and locking the distance. The radial or lateral expansion provides a good seal between the balloon and the adjacent anatomy. FIG. 11*b* shows the occlusion device 20 after the balloon 5 has been radially or laterally expanded.

Thereafter, the occlusion device 120 is released from the delivery system 107.

For some applications, the proximal base element 4 and the distal tip element 10 are shaped so as to define the above-mentioned respective guidewire openings 105*a* and 105*b* substantially coaxial to the balloon lumen 6 for slidingly receiving therein the guidewire 106, and advancing the occlusion device 120 over the guidewire 106 comprises sliding the guidewire 106 through the guidewire openings 105*a* and 105*b* described hereinabove.

For some applications, the balloon 5 has the above-mentioned balloon lumen 6 forming the above-mentioned longitudinal passage 27 from the proximal side 28A to the distal side 28B of the balloon 5. The distance between the distal tip element 10 and the proximal base element 4 is shortened to the desired distance by pulling the elongate actuating element 9 disposed longitudinally slidable in the balloon lumen 6, connected to the distal tip element 10, and longitudinally moveable with respect to the proximal base element 4. The distance is locked using locking mechanism 2 for maintaining, between the distal tip element 10 and the proximal base element 4, the distance set using the elongate actuating element 9.

For some applications, the occlusion device 120 is released from the delivery system 107 by releasing the above-mentioned proximal connection element 1 of the occlusion device 120 from the correspondingly configured distal connection element of the delivery system 107.

Optionally, the balloon 5 is partially exposed, in its compressed form, from the implant catheter 14 of the delivery system 107 into the area to be treated (e.g., exposed for half of the length of the balloon 5), and only the exposed portion of the balloon 5 is inflated. The balloon 5 is then repositioned for better occlusion targeting, and the balloon 5 is subsequently fully exposed from the delivery system 107, and the remaining portion of the balloon 5 is inflated. Subsequently, the longitudinal distance is shortened.

Optionally, a portion of the balloon 5 is exposed, in its compressed form, from the implant catheter 14 of the delivery system 107 into the area to be treated (e.g., exposed for half of the length of the balloon 5), and only the exposed portion of the balloon 5 is inflated. The exposed portion of the balloon 5 is expanded by shortening the distance between the distal tip element 10 and the proximal base element 4 by moving the distal tip element 10 toward the proximal base element 4. Before the occlusion device 120 is released from the delivery system 107, the remainder of the balloon 5 is exposed from the implant catheter, inflated, and expanded by further shortening the distance between the distal tip element 10 and the proximal base element 4.

For some applications in which the method is used to treat paravalvular leak between a prosthetic cardiac valve and adjacent cardiac tissue of the patient, positioning and inflating the compliant balloon comprise positioning the balloon 5 in a ventricle of the patient; thereafter, partially inflating the balloon 5; thereafter, disposing the balloon 5 approximately at a longitudinal center of the paravalvular leak; and thereafter, further inflating the balloon 5. The balloon 5 is expanded after further inflating the balloon 5. For some applications, the balloon 5 is disposed approximately at the longitudinal center of the paravalvular leak by proximally withdrawing the balloon 5 until the balloon 5 is disposed approximately at the longitudinal center of the paravalvular leak.

Figure 12A:
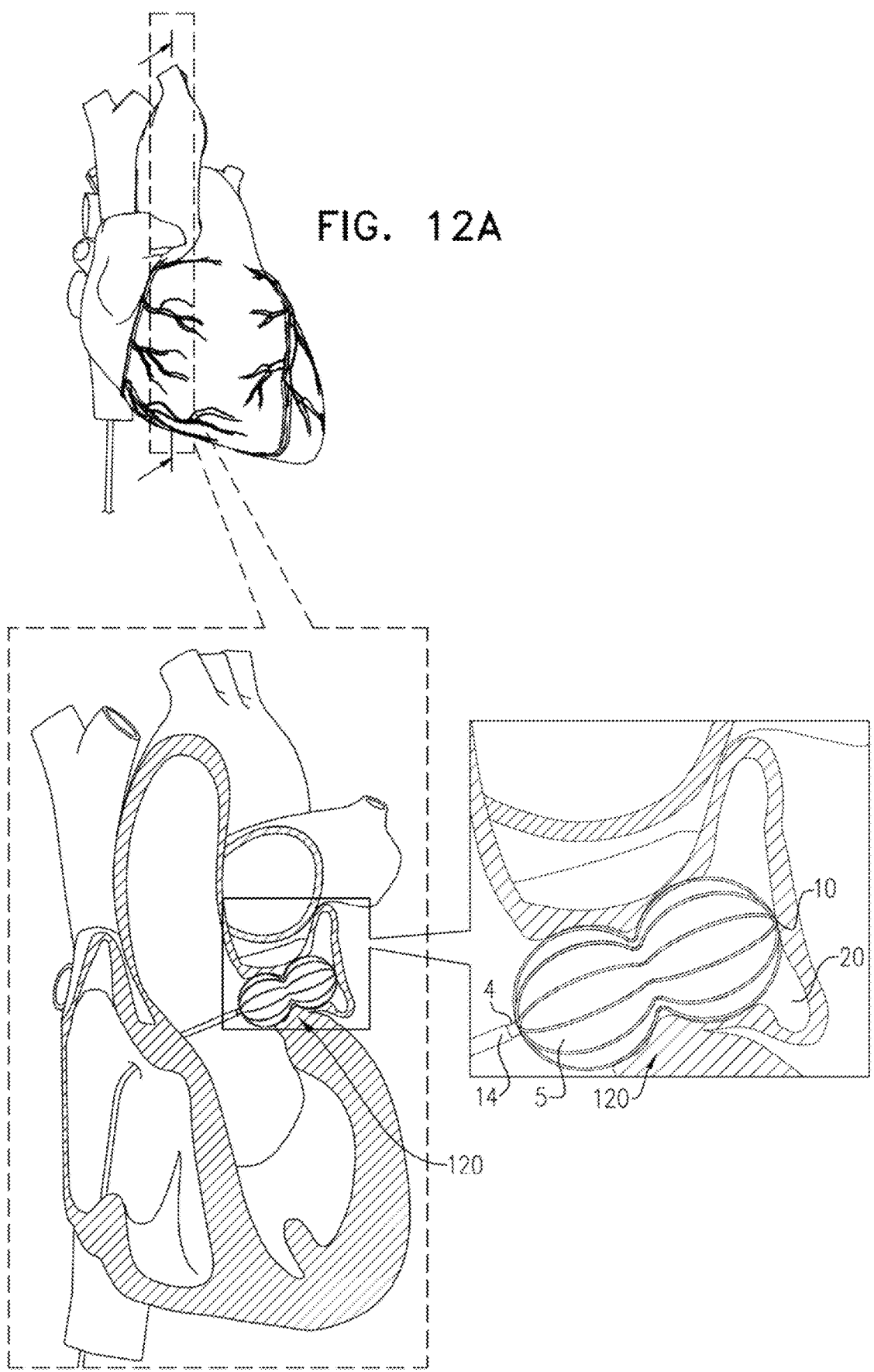
FIGS. 12a and 12b show side views of the occlusion device illustrated in FIG. 2a when expanded within a cardiovascular defect intended as cavity or discontinuity of the body tissue, in accordance with respective applications of the present invention.
Figure 12B:
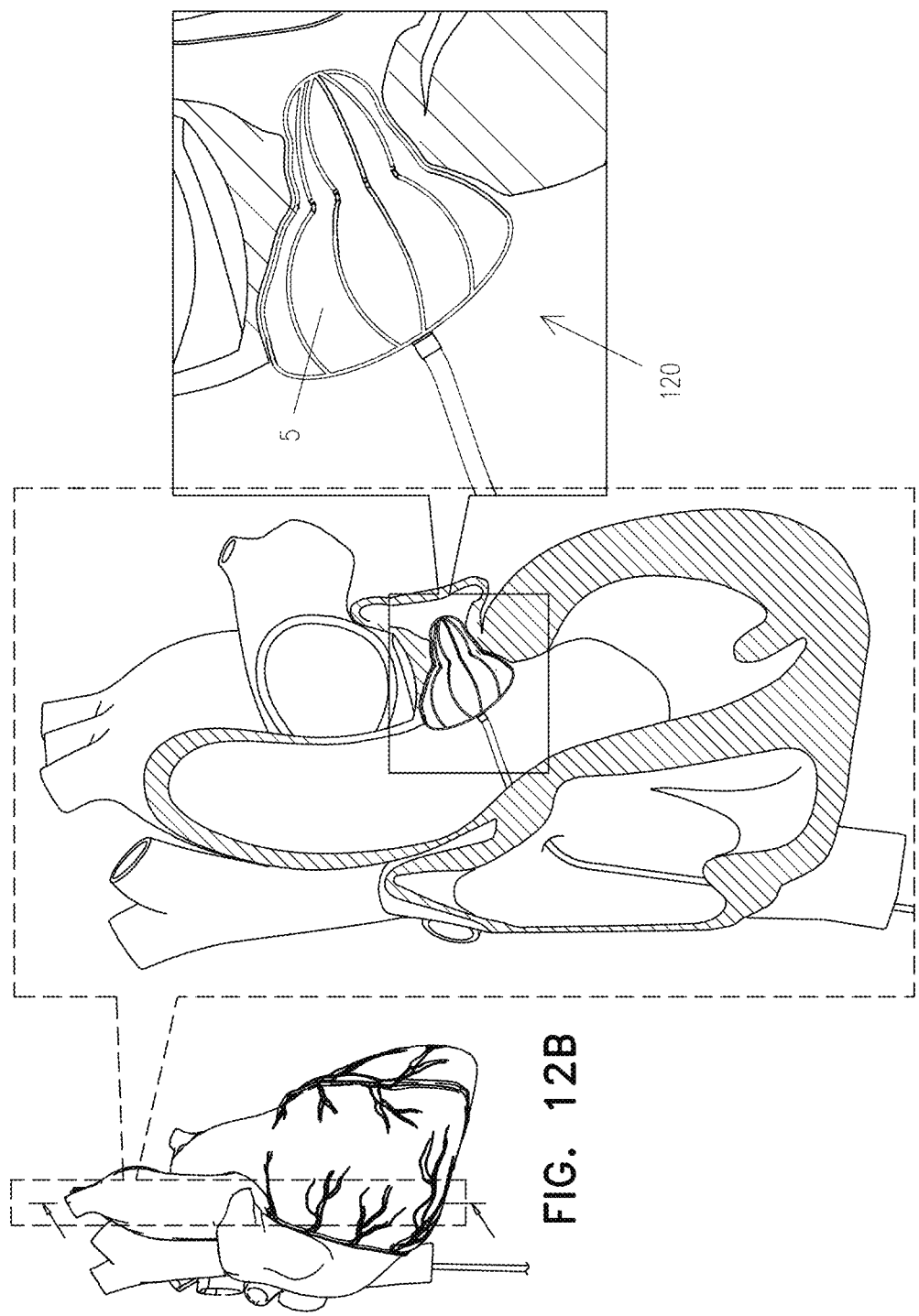

FIGS. 12*a-b* show side views of the occlusion device 120 illustrated in FIG. 2*a* when expanded within a cavity or discontinuity of the body tissue, in accordance with respective applications of the present invention. For example, the cavity or discontinuity may be a cardiovascular defect, such as a left atrial appendage (LAA). FIGS. 12*a-b* show the occlusion device 120 by way of example; these techniques may also be used with the other occlusion devices described herein, mutatis mutandis. The deployment method described hereinabove with reference to FIGS. 10*a-c* and 11*a-b* may be used to achieve the implantations shown in FIGS. 12*a-b*, mutatis mutandis.

For some applications, the balloon 5 is configured to have a figure-eight shape (as shown in FIG. 12*a*), a pear shape (as shown in FIG. 12*b*, or a multilobed shape.

Figure 13A:
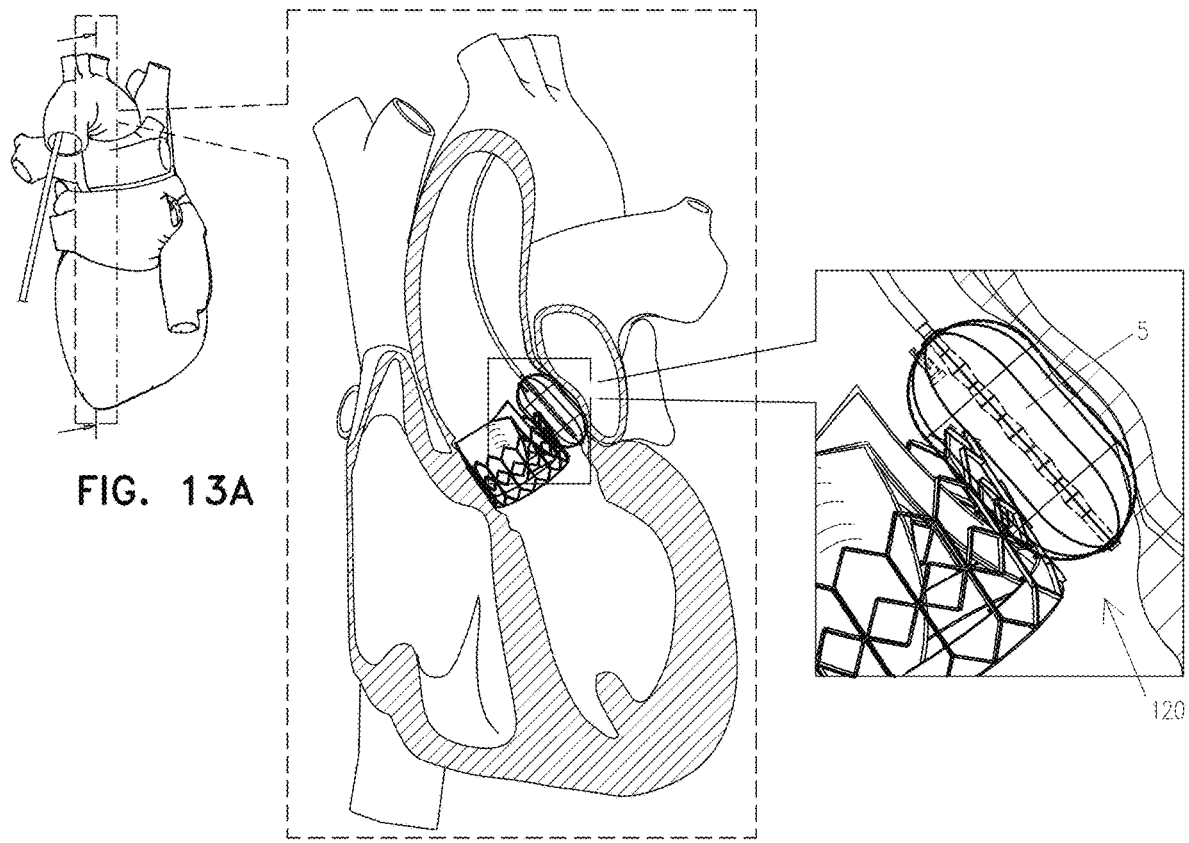

FIGS. 13*a-b* show side views of the occlusion device 120 illustrated in FIG. 2*a* when expanded within a gap between a medical device and the adjacent body tissue, in accordance with an application of the present invention. For example, the medical device may comprise a stent, such as a stent of a prosthetic valve. FIGS. 13*a-b* shows occlusion device 120 by way of example; these techniques may also be used with the other occlusion devices described herein, mutatis mutandis. The deployment method described hereinabove with reference to FIGS. 10*a-c* and 11*a-b* may be used to achieve the implantation shown in FIGS. 13*a-b*, mutatis mutandis.

In the configuration shown in FIG. 13*b*, the frame 122 of the occlusion device 120 comprises a backbone strut 111 that connects the proximal base element 4 and the distal tip element 10, and is thicker than the other struts 11, if provided. The backbone strut 111 is configured to reduce relative inflation on its lateral side of the balloon 5 compared to inflation of the balloon elsewhere, thereby providing a balloon shape that is appropriate for the anatomy of the gap to be filled. Alternatively or additionally, the wall of the balloon 5 on one lateral side may be thicker longitudinally on one lateral side, to create the backbone that causes the balloon to inflate less on that side.

Figures 14A, 14B, 14C:
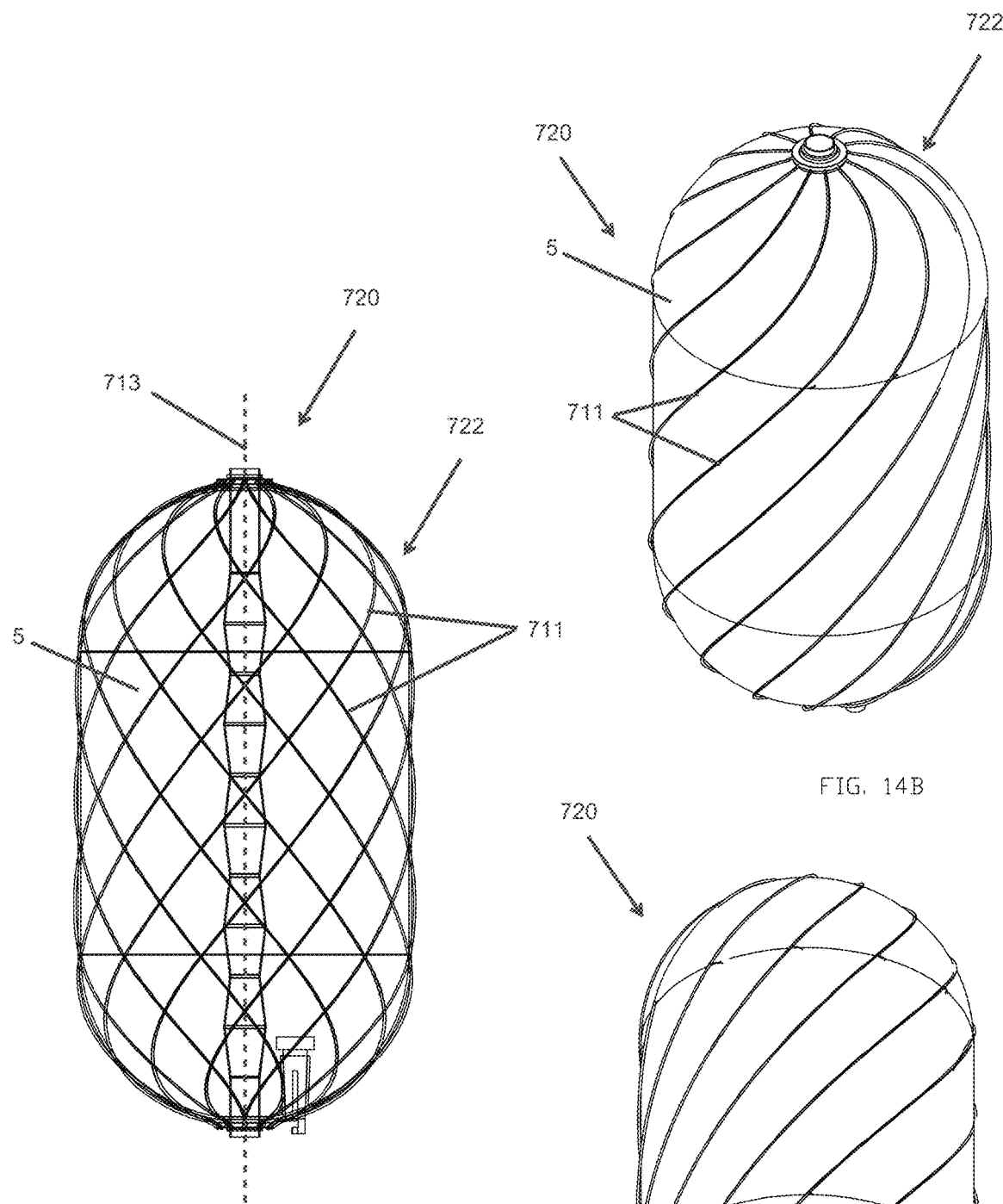
FIG. 14a shows a cross-sectional view of an expanded occlusion device according to an application of the present invention.
FIGS. 14b and 14c show side elevational views of the occlusion device illustrated in FIG. 14a, in accordance with an application of the present invention.

Reference is now made to FIG. 14*a*, which shows a cross-sectional view of an expanded occlusion device 720 according to an application of the present invention. Reference is also made to FIGS. 14*b* and 14*c*, which show side elevational views of the occlusion device 720 illustrated in FIG. 14*a*, in accordance with an application of the present invention. Except as described below, occlusion device 720 may implement any of the features of the other occlusion devices described hereinabove (including, but not limited to occlusion devices 20, 120, 220, 320, 370, 380, 390, 420, 520, and 540) or hereinbelow (including, but not limited to occlusion device 620).

As shown in FIGS. 14*a-c*, in this configuration the occlusion device 720 comprises a frame 722 that comprises a plurality of struts 711, which may have any suitable form, passing inside (not shown) or outside (as shown) and tapering the balloon 5 component. Such an application may allow a cage-like structural confinement of the balloon 5 within its assembly, to avoid unnecessary interference of the occlusion device 720 with the body tissue or with implanted prostheses and to provide anchoring support of the occlusion device 720 within the defect, e.g., the cardiovascular defect. In this application, the frame 722 may comprise 2, 4, 6, 8, 10, 12 or any other suitable even or odd number of struts 711. The struts 711 may be disposed inside or outside the balloon 5. For some applications, the struts 711 are not fixed to any surfaces of the balloon 5. For other applications, the struts 711 are (a) fixed to a surface (inner or outer) of the balloon 5, (b) embedded in the wall of the balloon 5 during manufacture (such as by being cast within the wall). Alternatively, the balloon 5 may be molded over the struts 711, which remain internally fixed to the balloon 5.

In this configuration, the struts 711 are not arranged parallel with a central longitudinal axis 713 of the occlusion device 720. For example, the struts 711 may be arranged in a generally helical configuration around the balloon 5, such as shown.

Figures 15A, 15B, 15C:
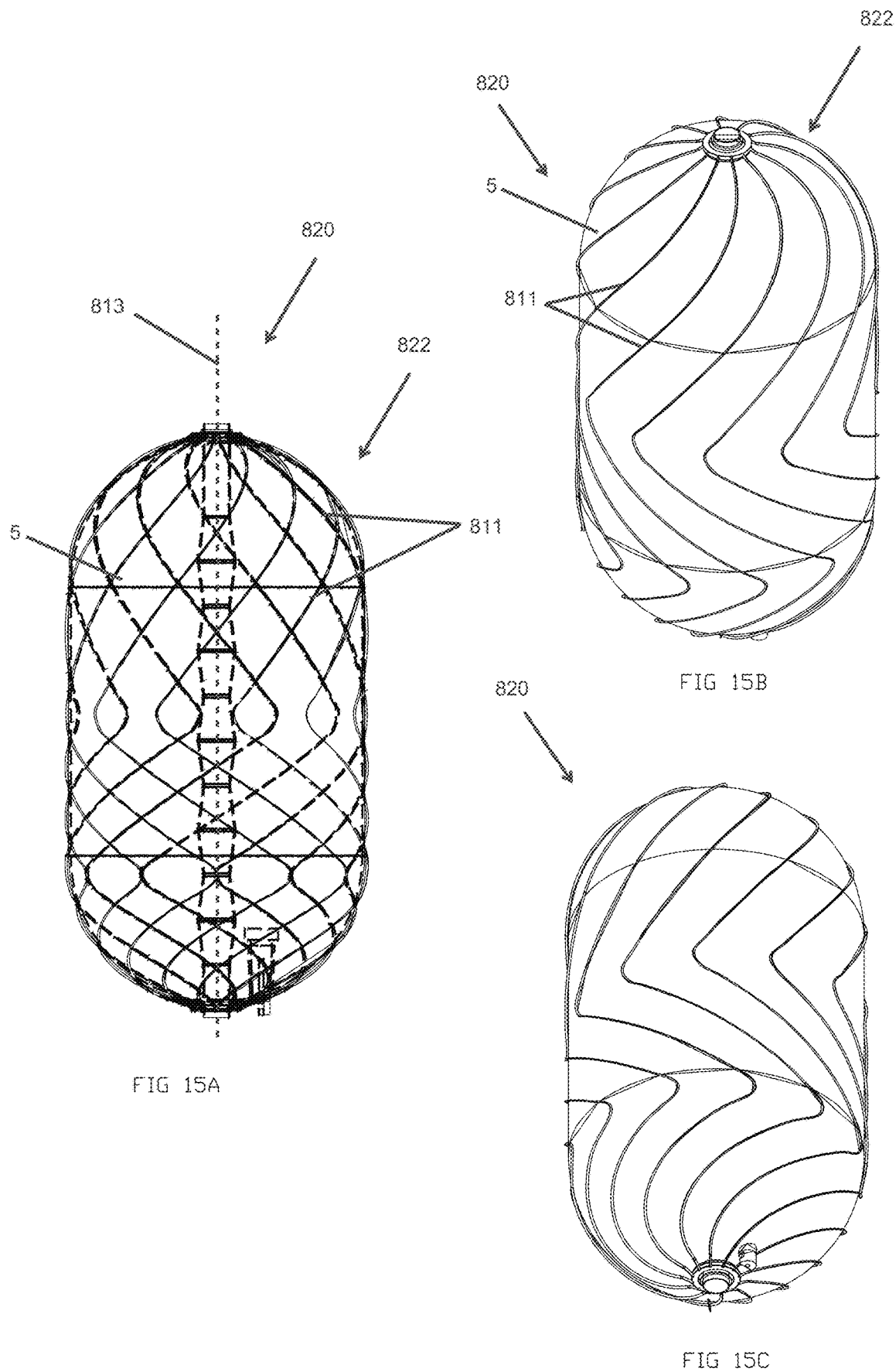
FIG. 15a shows a cross-sectional view of an expanded occlusion device according to an application of the present invention.
FIGS. 15b and 15c show side elevational views of the occlusion device illustrated in FIG. 15a, in accordance with an application of the present invention.

Reference is now made to FIG. 15*a*, which shows a cross-sectional view of an expanded occlusion device 820 according to an application of the present invention. Reference is also made to FIGS. 15*b* and 15*c*, which show side elevational views of the occlusion device 820 illustrated in FIG. 15*a*, in accordance with an application of the present invention. Except as described below, occlusion device 820 is identical to occlusion device 720, described hereinabove with reference to FIGS. 14*a-c* and may implement any of the features thereof or of the other occlusion devices described hereinabove (including, but not limited to occlusion devices 20, 120, 220, 320, 370, 380, 390, 420, 520, and 540) or hereinbelow (including, but not limited to occlusion device 620).

As shown in FIGS. 15*a-c*, in this configuration the occlusion device 820 comprises a frame 822 that comprises a plurality of struts 811, which may have any of the features of the frame 722 and/or the struts 711 described hereinabove with reference to FIGS. 14*a-c*.

In this configuration, the struts 811 are not arranged parallel with a central longitudinal axis 813 of the occlusion device 820. For example, the struts 811 may be arranged in a zig-zag configuration around the balloon 5, optionally including partially helical portions, such as shown.

Reference is now made to FIG. 16, which shows a method of deploying the occlusion device 120, in accordance with an application of the present invention. FIG. 16 shows the occlusion device 120 by way of example; these techniques may also be used with the other occlusion devices described herein, mutatis mutandis. The first frame of FIG. 16 shows the delivery system 107 approaching the left atrial appendage defect. The second frame shows half of the occlusion device 120 exposed and pre-inflated. The third frame shows half of the occlusion device 120 adjusted. The fourth frame shows the other half of the occlusion device 120 exposed and pre-inflated. The fifth frame shows full inflation of the entire occlusion device 120, and further adjustment that shortens the distance between the proximal base element 4 and the distal tip element 10. The sixth (last) frame shows release of the occlusion device 120 at the target location.

Figure 17A:
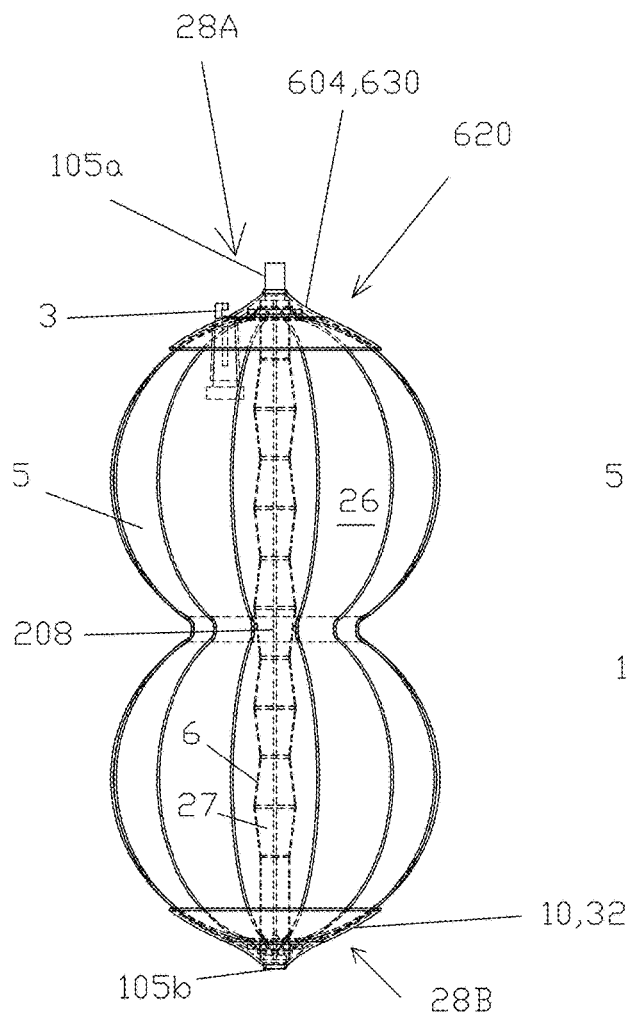
FIG. 17a shows a cross-sectional view of an expanded occlusion device according to an application of the invention, in accordance with an application of the present invention.
Figure 17B:
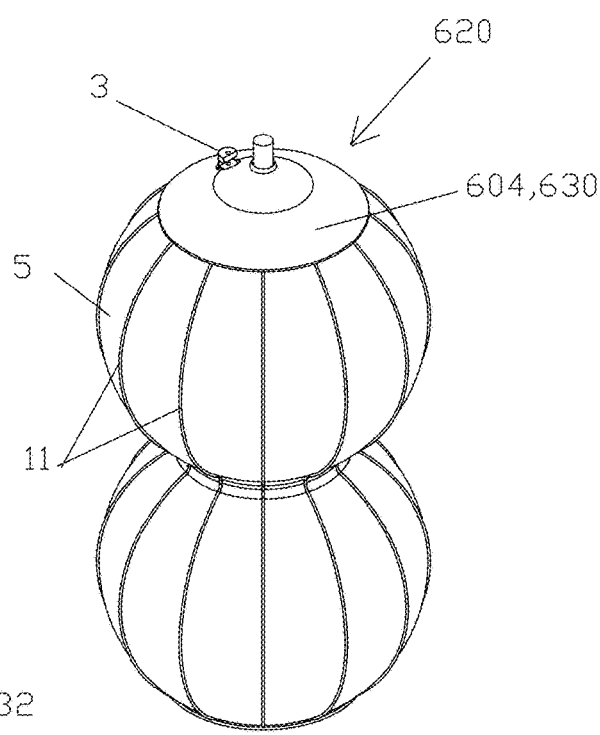
FIG. 17b shows a side elevational view of the occlusion device illustrated in 17a, in accordance with an application of the present invention.

Reference is now made to FIG. 17*a*, which shows a cross-sectional view of an expanded occlusion device 620 according to an application of the present invention. Reference is also made to FIG. 17*b*, which shows a side elevational view of the occlusion device 620 illustrated in FIG. 17*a*, in accordance with an application of the present invention. Except as described below, the occlusion device 620 may implement any of the features of the other occlusion devices described herein, mutatis mutandis, including, but not limited to, the struts of the frames described herein and the materials of the components of the occlusion devices. Like reference numerals refer to like parts.

The occlusion device 620 comprises:
the compliant balloon 5 defining the fluid-tight balloon chamber 26, and comprising the inflation port 3 for filling and unfilling a fluid into and from the balloon chamber 26;
the distal tip element 10 disposed at the distal side 28B of the balloon 5, and a proximal base element 604 disposed at the proximal side 28A of the balloon 5;
an elongate element 608 having a fixed length, and fixed to the distal tip element 10 and the proximal base element 604 so as to set a fixed distance between the distal tip element 10 and the proximal base element 604; typically, the elongate element 608 is selected from the group consisting of: a tube, a wire, a shaft, a cable, a strand, and a fiber; and
the proximal connection element 1 that is disposed at the proximal side 28A of the balloon 5 and is configured to releasably connect the occlusion device 620 to a correspondingly configured distal connection element of the delivery system 107.

Typically, the balloon 5 has the balloon lumen 6 forming the longitudinal passage 27 from the proximal side 28A to the distal side 28B of the balloon 5. For some applications, the elongate element 608 is disposed in the balloon lumen 6. Typically, the proximal base element 604 and the distal tip element 10 are shaped so as to define respective guidewire openings 605*a* and 605*b* substantially coaxial to the balloon lumen 6 for slidingly receiving therein the guidewire 106.

For some applications, the proximal base element 604 and the distal tip element 10 comprise a proximal disk 630 and the distal disk 32, respectively.

For some applications, the occlusion device 620 further comprises at least one connecting strut fixed to the distal tip element and to the proximal base element, such as the single connecting strut 21 described hereinabove with reference to FIGS. 1*a-c*, the single connecting strut 12 described hereinabove with reference to FIGS. 3*a-c*, or the plurality of struts 11 described hereinabove with reference to FIGS. 2*a-c*. The strut or struts may be disposed inside and/or outside the balloon 5, and be arranged as described hereinabove.

In an application of the present invention, a method of occluding a cardiovascular defect or a gap between a medical device and adjacent body tissue of a patient is provided. The method comprises:
advancing the guidewire 106 into a body of the patient using a delivery system;
positioning the compliant balloon 5 of the occlusion device 620 in a compressed form thereof in the cardiovascular defect or the gap to be occluded, by advancing the occlusion device 620 over the guidewire 106;
inflating the compliant balloon 5 by filling, via the inflation port 3 of the balloon 5, a fluid into the fluid-tight balloon chamber 26 defined by the balloon 5, such that the elongate element 608, which has a fixed length and is fixed to the distal tip element 10 and the proximal base element 604, sets a fixed distance between the distal tip element 10 and the proximal base element 604, the distal tip element 10 disposed at the distal side 28B of the balloon 5, and the proximal base element 604 disposed at the proximal side 28A of the balloon 5; and releasing the occlusion device 620 from the delivery system.

In some applications of the present invention, two or more occlusion devices are implanted to occlude a defect, either in series and/or alongside one another. For some applications, frames of the two or more occlusion devices are configured to connect the two or more occlusion devices together, typically in situ during an implantation procedure. For some applications, a portion of the surface of one of the balloons is bare of any of the frame, and the frame of another balloon is brought into contact with the bare portion of the other balloon, such as in order to avoid para-balloon leakage.

In some applications of the present invention, the occlusion devices described herein are packaged in sterile packaging.

In any of the configurations described herein, the balloon 5 may optionally have an average wall thickness of between 100 and 5000 microns, such as between 200 and 1000 microns. Alternatively, the balloon 5 does not have this average wall thickness.

In any of the configurations described herein, the balloon 5 may optionally have, at a thinnest portion of a wall of the balloon 5, a thinnest wall thickness of between 20 and 500 microns, such as between 40 and 100 microns. Alternatively, the balloon 5 does not have this thinnest wall thickness.

In any of the configurations described herein, the occlusion device may comprise a proximal radiopaque marker 23 that is fixed to the proximal base element and comprises a material that is more radiopaque than the proximal base element. Alternatively or additionally, in any of the configurations described herein, the occlusion device may comprise a distal radiopaque marker 25 that is fixed to the distal tip element and comprises a material that is more radiopaque than the distal tip element. These radiopaque markers enable the accurate positioning of the occlusion device echocardiographic, fluoroscopic, and/or x-ray guidance.

The proximal and distal radiopaque markers 23 and 25 are shown by way of example in FIGS. 1*b* and 1*c*; these markers may also be provided in the other occlusion devices described herein. Alternatively, the occlusion devices described herein do not comprise proximal radiopaque marker 23 or distal radiopaque marker 25. For example, each of the proximal radiopaque marker 23 and/or the distal radiopaque marker 25 may be shaped as a ring, such as shown in FIGS. 1*b* and 1*c*; alternatively, the markers may have other shapes and/or different shapes or sizes from each other.

For example, the material of the proximal radiopaque marker 23 and/or the distal radiopaque marker 25 may comprise Au, PtIr, or Ta.

For example, the proximal radiopaque marker 23 and/or the distal radiopaque marker 25 may be fixed to the proximal base element and the distal tip element, respectively, by gluing, soldering, crimping, or welding.

In any of the configurations described herein, when the occlusion device is in a compressed, uninflated form, a greatest distance between the proximal base element 4 and the distal tip element 10 is between 8 and 80 mm, such as between 10 and 60 mm. (The "greatest distance" is the distance between respective points of the proximal base element 4 and the distal tip element 10, which points are farthest from each other.) Optionally, the occlusion device is in the above-mentioned compressed, uninflated form when the proximal connection element 1 is attached to the delivery system 107 and the occlusion device is not disposed in the implant catheter 14.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for occluding a cardiovascular defect or a gap between a medical device and adjacent body tissue, the apparatus for use with a guidewire and a delivery system, the apparatus comprising:
   an occlusion device, which has a longitudinally extended form from which the occlusion device is shortenable, the occlusion device comprising:
      a compliant balloon (a) defining a fluid-tight balloon chamber, and (b) comprising an inflation port for filling and unfilling a fluid into and from the balloon chamber;
      a tube, which (a) is disposed within the fluid-tight balloon chamber, and (b) when the occlusion device is in the longitudinally extended form, forms a longitudinal passage from a proximal side to a distal side of the balloon such that the fluid-tight balloon chamber radially surrounds the tube;
      a distal tip element disposed at the distal side of the balloon, and a proximal base element disposed at the proximal side of the balloon;
      a locking mechanism; and
      a proximal connection element that is disposed at the proximal side of the balloon and is configured to releasably connect the occlusion device to a correspondingly configured distal connection element of the delivery system; and
   an elongate actuating element disposed longitudinally slidable in the tube, connected to the distal tip element, and longitudinally moveable with respect to the proximal base element so as to set a distance between the distal tip element and the proximal base element,
   wherein the locking mechanism is configured to maintain, between the distal tip element and the proximal base element, the distance set using the elongate actuating element.

2. The apparatus according to claim 1, wherein the elongate actuating element is selected from the group consisting of: a wire, a cable, a strand, and a fiber.

3. The apparatus according to claim 1, wherein the distal tip element and the proximal base element are shaped so as to define respective guidewire openings substantially coaxial to the tube for slidingly receiving therein the guidewire.

4. The apparatus according to claim 1, wherein the proximal base element and the distal tip element comprise a proximal disk and a distal disk, respectively.

5. The apparatus according to claim 1, wherein the locking mechanism is disposed at the proximal side of the balloon.

6. The apparatus according to claim 5, wherein the locking mechanism is connected to or integrated into the proximal base element.

7. The apparatus according to claim 1, further comprising at least one connecting metal strut fixed to the distal tip element and to the proximal base element.

8. The apparatus according to claim 7, wherein the at least one connecting metal strut comprises a single connecting metal strut disposed inside or outside the balloon.

9. The apparatus according to claim 7, wherein the at least one connecting metal strut comprises a plurality of connecting metal struts disposed inside or outside the balloon.

10. The apparatus according to claim 9, wherein the plurality of connecting metal struts are disposed in a cage-like arrangement.

11. The apparatus according to claim 9, wherein the plurality of connecting metal struts are arranged as a frame.

12. The apparatus according to claim 1, wherein the occlusion device comprises the elongate actuating element, which is fixedly connected to the distal tip element.

13. The apparatus according to claim 12, wherein the elongate actuating element is longitudinally slidable with respect to the proximal base element.

14. The apparatus according to claim 12, wherein the locking mechanism comprises one or more pawls and the elongate actuating element comprises a plurality of teeth, so as to together provide a ratchet mechanism such that the distance between the distal tip element and the proximal base element is selectable from a range of distances by distally pulling the elongate actuating element through the locking mechanism.

15. The apparatus according to claim 12, wherein the elongate actuating element is selected from the group consisting of: a wire, a cable, a strand, and a fiber.

16. The apparatus according to claim 12,
wherein the elongate actuating element is shaped so as to define a thread,
wherein the locking mechanism comprises a threaded opening defined by the proximal base element, wherein the thread of the elongate actuating element is disposed within the threaded opening, and
wherein the occlusion device is configured such that rotation of the elongate actuating element with respect to the proximal base element causes the elongate actuating element to longitudinally move with respect to the proximal base element, thereby setting the distance between the distal tip element and the proximal base element and maintaining the set distance.

17. The apparatus according to claim 1, wherein the elongate actuating element is releasably connected to the distal tip element.

18. The apparatus according to claim 17,
wherein the occlusion device further comprises a locking elongate element fixed to the distal tip element and longitudinally slidable with respect to the proximal base element, and
wherein the locking mechanism is configured to lock the locking elongate element with respect to the proximal base element in order to maintain the distance set using the elongate actuating element.

19. The apparatus according to claim 18, wherein the locking elongate element is selected from the group consisting of: a tube, a wire, a shaft, a cable, a strand, and a fiber.

20. The apparatus according to claim 19, wherein the locking elongate element is the wire.

21. The apparatus according to claim 17, wherein the elongate actuating element is longitudinally slidable with respect to the proximal base element.

22. The apparatus according to claim 21,
wherein a distal portion of the elongate actuating element is shaped so as to define a thread, and
wherein the distal tip element is shaped so as to define a threaded opening to which the thread of the distal portion of the elongate actuating element is releasably threadingly connected, such that the elongate actuating element is releasably connected to the distal tip element.

23. The apparatus according to claim 17,
wherein the elongate actuating element is shaped so as to define a thread,
wherein the proximal base element is shaped so as to define a threaded opening, wherein the thread of the elongate actuating element is disposed within the threaded opening, and
wherein the occlusion device is configured such that rotation of the elongate actuating element with respect to the proximal base element causes the elongate actuating element to longitudinally move with respect to the proximal base element, thereby setting the distance between the distal tip element and the proximal base element and maintaining the set distance.

24. The apparatus according to claim 23,
wherein a distal portion of the elongate actuating element comprises a first positive connection element,
wherein the distal tip element is shaped so as to define a second positive connection element, and
wherein the first positive connection element is releasably connected to the second positive connection element, such that the elongate actuating element is releasably connected to the distal tip element.

25. The apparatus according to claim 1, wherein the inflation port comprises a self-closing valve.

26. The apparatus according to claim 25, wherein the inflation port is releasably connected to the delivery system, and wherein the self-closing valve is configured to close upon disconnection of the inflation port from the delivery system.

27. The apparatus according to claim 1, wherein the balloon has an average wall thickness of between 100 and 5000 microns.

28. The apparatus according to claim 1, wherein the balloon has, at a thinnest portion of a wall of the balloon, a thinnest wall thickness of between 20 and 500 microns.

29. An occlusion system comprising the apparatus according to claim 1, the occlusion system further comprising an implant catheter, in which the occlusion device is releasably disposed in a compressed form, in which the tube extends from the proximal side to the distal side of the balloon.

30. An occlusion system comprising the apparatus according to claim 1, the occlusion system further comprising the delivery system cooperating therewith, the delivery system comprising an implant catheter connected to an operating handle, the implant catheter comprising a longitudinal passageway for the guidewire, a distal connection element for releasably connecting the implant catheter to the correspondingly configured proximal connection element of the occlusion device, and an inflation tube channel releasably connectable to the corresponding inflation port of the occlusion device.

31. The apparatus according to claim 1, wherein the distance set by longitudinal movement of the elongate actuating element is selectable from a range of distances.

32. Apparatus for occluding a cardiovascular defect or a gap between a medical device and adjacent body tissue, the apparatus for use with a guidewire and a delivery system, the apparatus comprising an occlusion device, which comprises:
a compliant balloon defining a fluid-tight balloon chamber and comprising an inflation port for filling and unfilling a fluid into and from the balloon chamber;

a distal tip element disposed at a distal side of the balloon, and a proximal base element disposed at a proximal side of the balloon;

an elongate element having a fixed length, and fixed to the distal tip element and the proximal base element so as to set a fixed distance between the distal tip element and the proximal base element; and a proximal connection element that is disposed at the proximal side of the balloon and is configured to releasably connect the occlusion device to a correspondingly configured distal connection element of the delivery system.

33. The apparatus according to claim 32, wherein the elongate element is selected from the group consisting of: a wire, a cable, a strand, and a fiber.

34. The apparatus according to claim 32, wherein the occlusion device comprises a tube, which (a) is disposed within the fluid-tight balloon chamber, and (b) when the occlusion device is in the longitudinally extended form, forms a longitudinal passage from a proximal side to a distal side of the balloon such that the fluid-tight balloon chamber radially surrounds the tube, and wherein the elongate element is disposed in the tube.

35. An occlusion system comprising the apparatus according to claim 32, the occlusion system further comprising an implant catheter, in which the occlusion device is releasably disposed in a compressed form, with the elongate element fixed to the distal tip element and the proximal base element.

* * * * *